(12) United States Patent  (10) Patent No.: US 8,131,332 B2
Maynard et al.  (45) Date of Patent: *Mar. 6, 2012

(54) DETERMINATION OF A MEASURE OF A GLYCATION END-PRODUCT OR DISEASE STATE USING TISSUE FLUORESCENCE OF VARIOUS SITES

(75) Inventors: John D Maynard, Albuquerque, NM (US); Marwood Neal Ediger, Albuquerque, NM (US); Robert D Johnson, Federal Way, WA (US); Mark Ries Robinson, Albuquerque, NM (US)

(73) Assignee: VeraLight, Inc., Albuquerque, NM (US)

( * ) Notice: Subject to any disclaimer, the term of this patent is extended or adjusted under 35 U.S.C. 154(b) by 1323 days.

This patent is subject to a terminal disclaimer.

(21) Appl. No.: 11/675,524

(22) Filed: Feb. 15, 2007

(65) Prior Publication Data

US 2007/0197880 A1  Aug. 23, 2007

Related U.S. Application Data

(63) Continuation-in-part of application No. 11/624,214, filed on Jan. 17, 2007, which is a continuation-in-part of application No. 11/350,916, filed on Feb. 9, 2006, now abandoned, said application No. 11/624,214 is a continuation-in-part of application No. 11/561,380, filed on Nov. 17, 2006, which is a continuation of application No. 10/972,173, filed on Oct. 22, 2004, now Pat. No. 7,139,598, which is a continuation-in-part of application No. 10/117,272, filed on Apr. 4, 2002, now Pat. No. 7,043,288.

(60) Provisional application No. 60/781,638, filed on Mar. 10, 2006, provisional application No. 60/651,679, filed on Feb. 9, 2005, provisional application No. 60/517,418, filed on Nov. 4, 2003, provisional application No. 60/515,343, filed on Oct. 28, 2003.

(51) Int. Cl.
*A61B 5/1455* (2006.01)
(52) U.S. Cl. .......................... 600/310; 600/476
(58) Field of Classification Search .................. 600/310, 600/317, 322, 473, 476
See application file for complete search history.

(56) References Cited

U.S. PATENT DOCUMENTS 4,094,609 A  6/1978  Fujii et al.
(Continued)

OTHER PUBLICATIONS

Ediger MN, Fleming CM, Rohrscheib M, Way JF, Nguyen CM and Maynard JD: Noninvasive Fluorescence Spectroscopy for Diabetes Screening: A Clinical Case-Control Study (Abstract). Diabetes Technology Meeting, San Francisco, CA, Nov. 11, 2005.

(Continued)

*Primary Examiner* — Eric Winakur
(74) *Attorney, Agent, or Firm* — V. Gerald Grafe

(57) ABSTRACT

Embodiments of the present invention provide an apparatus suitable for determining properties of in vivo tissue from spectral information collected from various tissue sites. An illumination system provides light at a plurality of broadband ranges, which are communicated to an optical probe. The optical probe can be a flexible probe in some embodiments, allowing ease of application. Light homogenizers and mode scramblers can be employed to improve the performance in some embodiments. The optical probe in some embodiments physically contacts the tissue, and in some embodiments does not physically contact the tissue. The optical probe receives light from the illumination system and transmits it to tissue, and receives light diffusely reflected in response to the broadband light, emitted from the in vivo tissue by fluorescence thereof in response to the broadband light, or a combination thereof. The optical probe can communicate the light to a spectrograph which produces a signal representative of the spectral properties of the light. An analysis system determines a property of the in vivo tissue from the spectral properties.

25 Claims, 48 Drawing Sheets

U.S. PATENT DOCUMENTS

| | | | |
|---|---|---|---|
| 4,653,880 | A | 3/1987 | Sting et al. |
| 4,655,225 | A | 4/1987 | Dahne et al. |
| 4,661,706 | A | 4/1987 | Messerschmidt et al. |
| 4,684,255 | A | 8/1987 | Ford |
| 4,712,912 | A | 12/1987 | Messerschmidt |
| 4,730,882 | A | 3/1988 | Messerschmidt |
| 4,853,542 | A | 8/1989 | Milosevic et al. |
| 4,857,735 | A | 8/1989 | Noller |
| 4,859,064 | A | 8/1989 | Messerschmidt et al. |
| 4,867,557 | A | 9/1989 | Takatani et al. |
| 4,882,492 | A | 11/1989 | Schlager |
| 4,883,351 | A | 11/1989 | Weiss |
| 4,883,953 | A | 11/1989 | Koashi et al. |
| 4,895,159 | A | 1/1990 | Weiss |
| 4,975,581 | A | 12/1990 | Robinson et al. |
| 5,007,423 | A | 4/1991 | Branstetter et al. |
| 5,419,323 | A | 5/1995 | Kittrell et al. |
| 5,582,168 | A | 12/1996 | Samuels et al. |
| 5,601,079 | A | 2/1997 | Wong et al. |
| 5,754,716 | A | 5/1998 | Kim et al. |
| 5,935,062 | A | 8/1999 | Messerschmidt et al. |
| 6,070,093 | A | 5/2000 | Oosta et al. |
| 6,088,606 | A | 7/2000 | Ignotz et al. |
| 6,124,597 | A | 9/2000 | Shehada et al. |
| 6,201,989 | B1 | 3/2001 | Whitehead et al. |
| 6,230,034 | B1 | 5/2001 | Messerschmidt et al. |
| 6,332,092 | B1 | 12/2001 | Deckert et al. |
| 6,505,059 | B1 | 1/2003 | Kollias |
| 6,537,211 | B1 | 3/2003 | Wang et al. |
| 6,571,118 | B1 | 5/2003 | Utzinger et al. |
| 6,574,490 | B2 | 6/2003 | Abbink et al. |
| 6,622,033 | B2 | 9/2003 | Messerschmidt et al. |
| 6,684,099 | B2 | 1/2004 | Ridder et al. |
| 6,862,091 | B2 | 3/2005 | Johnson |
| 6,865,408 | B1 | 3/2005 | Abbink et al. |
| 7,039,446 | B2 | 5/2006 | Ruchti et al. |
| 7,139,598 | B2 | 11/2006 | Hull et al. |
| 2001/0039483 | A1 | 11/2001 | Brand et al. |
| 2001/0046045 | A1 | 11/2001 | Dong et al. |
| 2002/0010401 | A1 | 1/2002 | Bushmakin et al. |
| 2002/0016534 | A1 | 2/2002 | Trepagnier et al. |
| 2002/0082487 | A1 | 6/2002 | Kollias et al. |
| 2002/0091324 | A1 | 7/2002 | Kollias et al. |
| 2003/0013973 | A1 | 1/2003 | Georgakoudi et al. |
| 2003/0195401 | A1 | 10/2003 | Tian et al. |
| 2004/0068193 | A1 | 4/2004 | Barnes et al. |
| 2004/0092822 | A1 | 5/2004 | Messerschmidt et al. |
| 2004/0114211 | A1 | 6/2004 | Trepagnier et al. |
| 2005/0131304 | A1 | 6/2005 | Stamatas et al. |
| 2005/0203355 | A1 | 9/2005 | Stamatas et al. |
| 2006/0089556 | A1 | 4/2006 | Bambot et al. |
| 2006/0094942 | A1 | 5/2006 | Winther |
| 2006/0149143 | A1 | 7/2006 | Colvin |
| 2006/0195022 | A1 | 8/2006 | Trepagnier et al. |

OTHER PUBLICATIONS

Hull EL, Ediger MN, Unione Aht, Deemer EK, Stroman ML and Baynes JW: Noninvasive, optical detection of diabetes: model studies with porcine skin. Optics Express 12:4496-4510, 2004.

Engelgau MM, Narayan KM, Herman WH: Screening for Type 2 diabetes. Diabetes Care 23:1563-1580, 2000.

http://www.diagnoptics.com/index.php?cat=products&page=publications, visited Feb. 26, 2007.

R. Meerwaldt; R. Graaff; P. H. N. Oomen; T. P. Links; J. J. Jager; N. L. Alderson; S. R. Thorpe; J. W. Baynes; R. O. B. Gans; A. J. Smit. Simple non-invasive assessment of advanced glycation endproduct accumulation. Diabetologia (2004) 47:1324-1330.

Helen L. Lutgers, MD; Reindert Graaff, MSC, PHD; Thera P. Links, MD, PHD; Lielith J. Ubink-Veltmaat, MD, PHD; Henk J. Bilo, MD, PHD; Rijk O. Gans, MD, PHD; Andries J. Smit, MD, PHD. Skin Autofluorescence as a Noninvasive Marker of Vascular Damage in Patients With Type 2 Diabetes. Diabetes Care, vol. 29, No. 12, December 2006.

Douwe J. Mulder, M.D.; Tara Van De Water, M.Sc.; Helen L. Lutgers, M.D.; Reindert Graaff, M.Sc., Ph.D.; Rijk O. Gans, M.D., Ph.D.; Felix Zijlstra, M.D., Ph.D.; and Andries J. Smit, M.D., Ph.D. Skin Autofluorescence, a Novel Marker for Glycemic and Oxidative Stress-Derived Advanced Glycation Endproducts: An Overview of Current Clinical Studies, Evidence, and Limitations. Diabetes Technology & Therapeutics vol. 8, No. 5, 2006.

Robbert Meerwaldt, MD, PHD; Helen L. Lutgers, MD; Thera P. Links, MD, PHD; Reindert Graaff, MSC, PHD; John W. Baynes, PHD; Rijk O.B. Gans, MD, PHD; Andries J. Smit, MD, PHD. Skin Autofluorescence Is a Strong Predictor of Cardiac Mortality in Diabetes. Diabetes Care, vol. 30, No. 1, Jan. 2007.

Ediger et al. Detecting Type 2 Diabetes with Noninvasive Skin Fluorescence Spectroscopy. Fifth Annual Diabetes Technology Meeting. Nov. 11, 2005.

Ediger MN, Fleming CM, Rohrscheib M, Way JF, Nguyen CM and Maynard JD: Noninvasive Fluorescence Spectroscopy for Diabetes Screening: a Clinical Case-Control Study (poster). Diabetes Technology Meeting, San Francisco, CA, Nov. 11, 2005.

C.D. Brown, Ph.D., H.T. Davis, Ph.D., M.N. Ediger, Ph.D.,,* C.M. Fleming, Ph.D., E.L. Hull, Ph.D., and M. Rohrscheib, M.D. Clinical Assessment of Near-Infrared Spectroscopy for Noninvasive Diabetes Screening. Diabetes Technology & Therapeutics. vol. 7, No. 3, 2005.

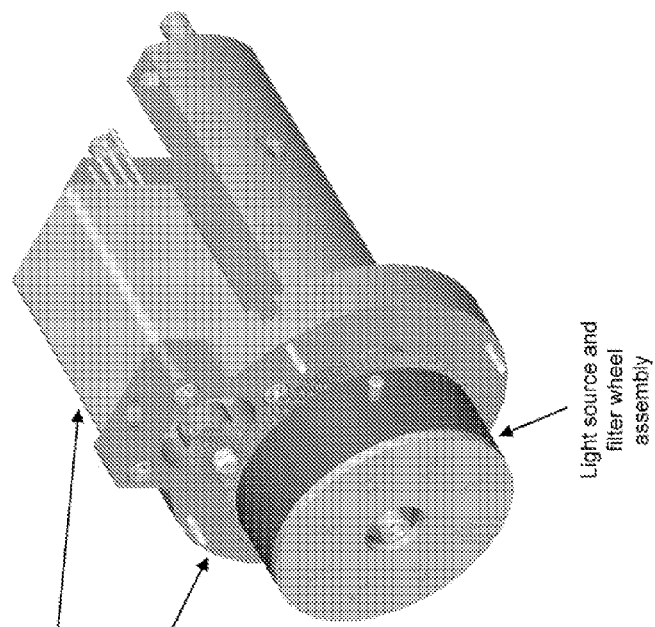
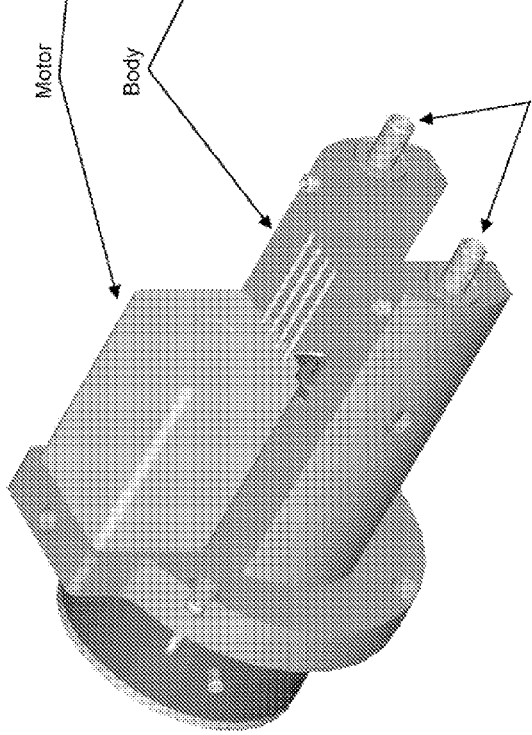
Fig. 11a
Fig. 11b

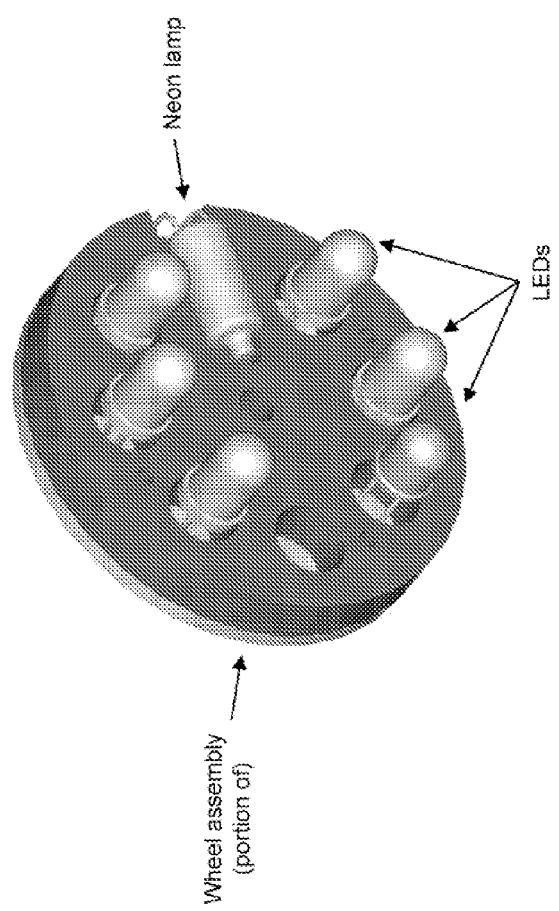

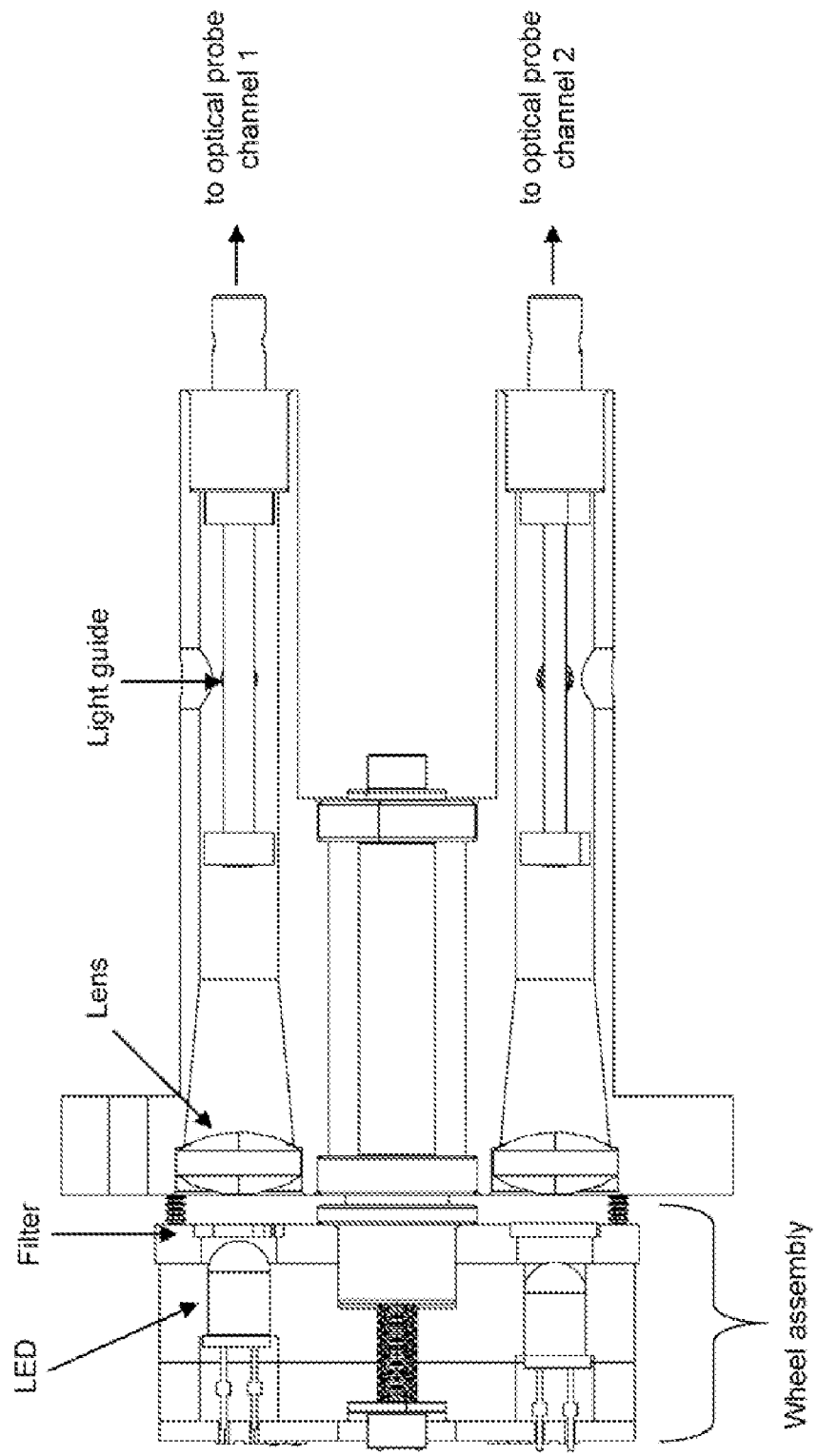

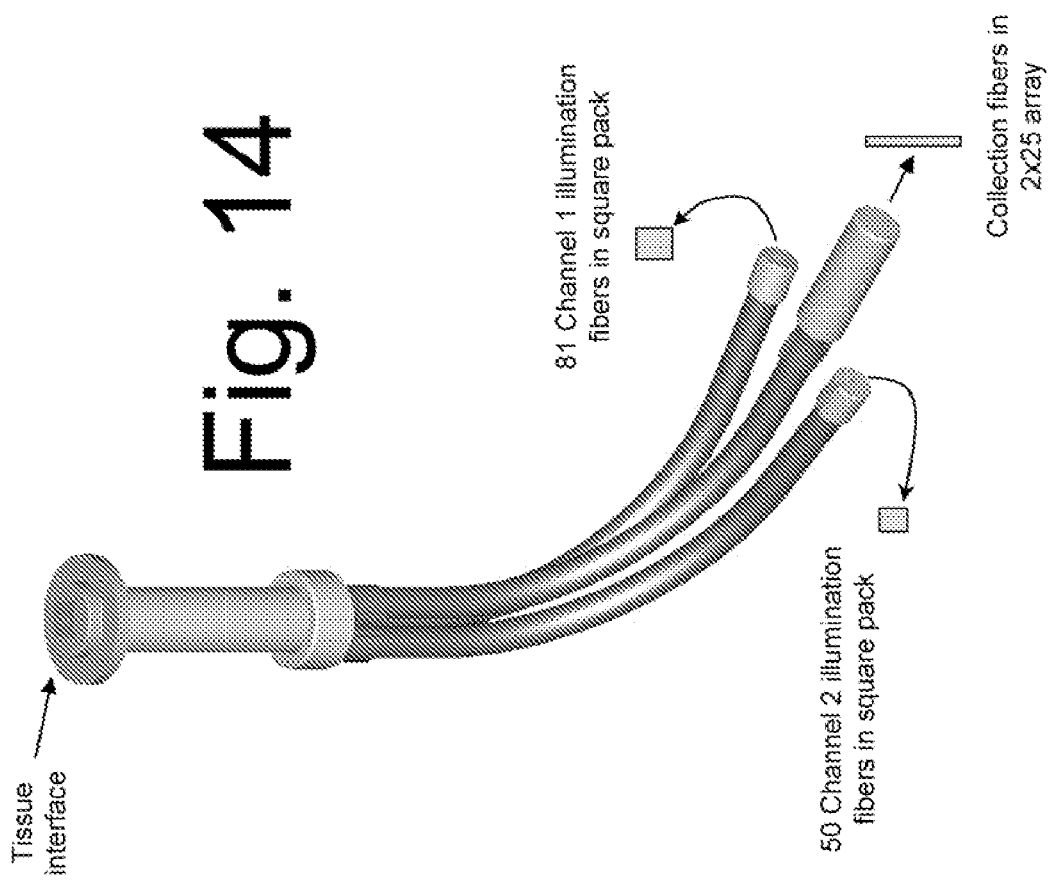

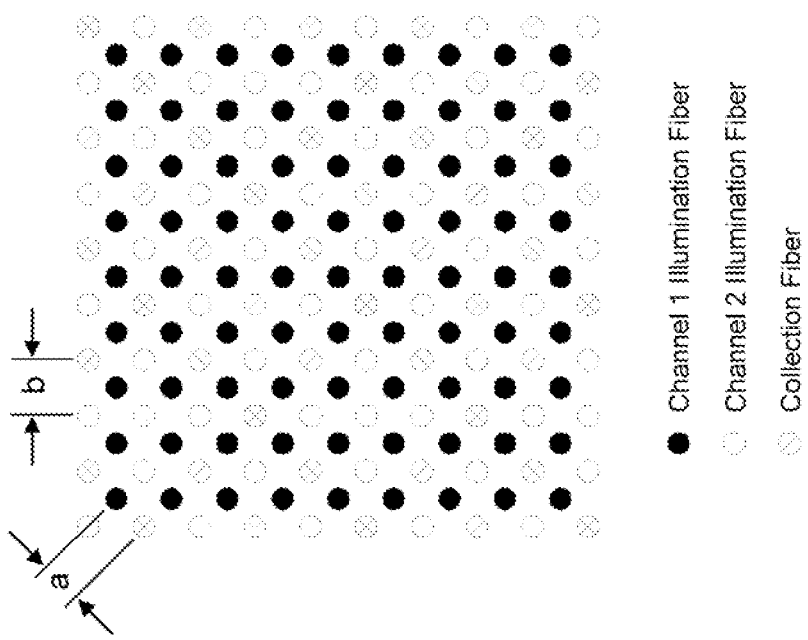

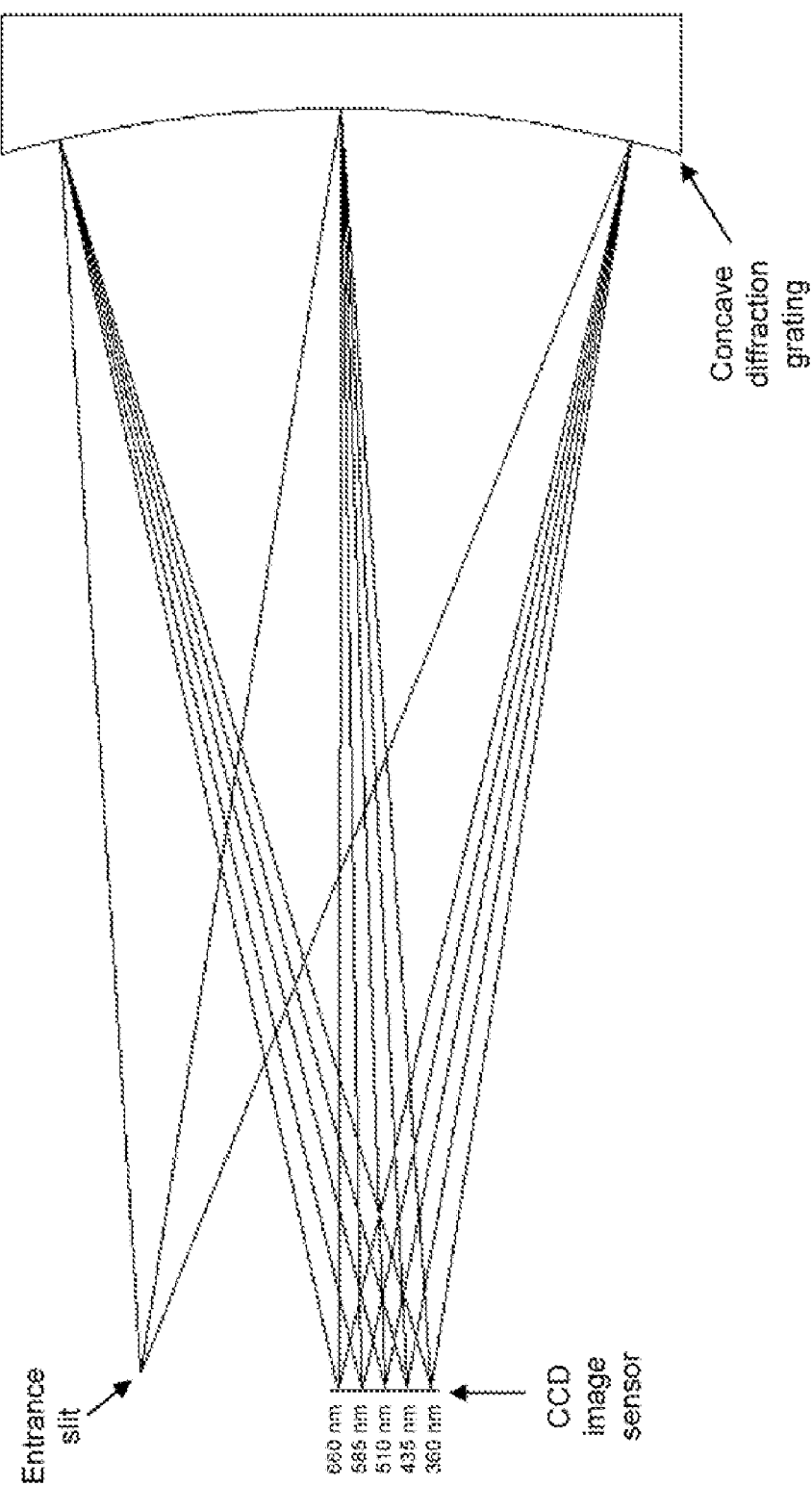

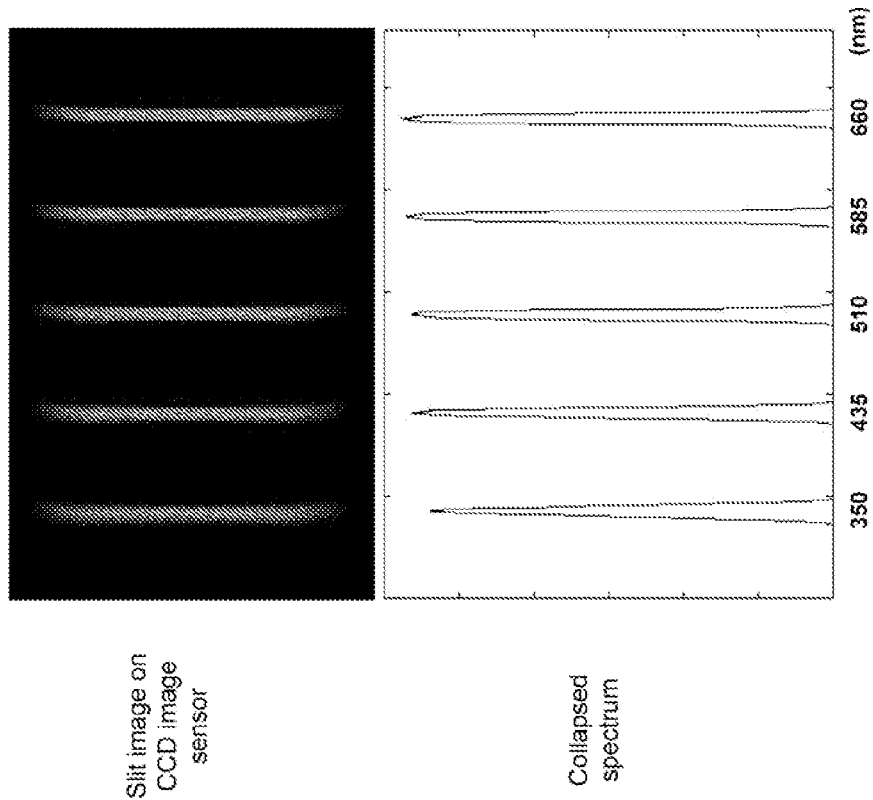

DETERMINATION OF A MEASURE OF A GLYCATION END-PRODUCT OR DISEASE STATE USING TISSUE FLUORESCENCE OF VARIOUS SITES

CROSS REFERENCES TO RELATED APPLICATIONS

This application (1) claims priority to U.S. provisional application 60/781,638, filed Mar. 10, 2006, titled "Methods and apparatuses for noninvasive detection of disease," incorporated herein by reference; and (2) claims priority as a continuation in part of U.S. application Ser. No. 11/350,916, filed Feb. 9, 2006, titled "Methods and apparatuses for non-invasive determination of analytes", which application claimed priority to U.S. provisional application 60/651,679, filed Feb. 09, 2005, each of which is incorporated herein by reference, and (3) claims priority as a continuation in part of U.S. application Ser No. 11/624214, filed Jan. 17, 2007, titled "Determination of a Measure of a Glycation End-Product or Disease State Using Tissue Fluorescence," which application claims priority under 35 U.S.C §120 as a continuation-in-part of U.S. patent application Ser. No. 11/561,380, entitled "Determination of a Measure of a Glycation End-Product or Disease State Using Tissue Fluorescence," filed Nov. 17, 2006, which was a continuation of U.S. patent application Ser. No. 10/972,173, entitled "Determination of a Measure of a Glycation End-Product or Disease State Using Tissue Fluorescence," filed Oct. 22, 2004, which was a continuation in part of U.S. patent application Ser. No. 10/116,272, entitled "Apparatus And Method For Spectroscopic Analysis Of Tissue To Detect Diabetes In An Individual," filed Apr. 4, 2002, incorporated herein by reference, and claimed the benefit of U.S. provisional application 60/515,343, "Determination of a Measure of a Glycation End-Product or Disease State Using Tissue Fluorescence," filed Oct. 28, 2003, incorporated herein by reference; and claimed the benefit of U.S. provisional application 60/517,418, "Apparatus And Method For Spectroscopic Analysis Of Tissue To Determine Glycation End-products," filed Nov. 4, 2003, each of which is incorporated herein by reference.

FIELD OF THE INVENTION

The present invention generally relates to determination of a tissue state from the response of tissue to incident light. More specifically, the present invention relates to methods and apparatuses suitable for determining the presence, likelihood, or progression of diabetes in human tissue from fluorescence properties of the tissue.

BACKGROUND OF THE INVENTION

The U.S. is facing a dangerous epidemic in type 2 diabetes. Of the estimated 20.6 million individuals with diabetes, approximately thirty percent of them are undiagnosed. See, e.g., National diabetes fact sheet. Atlanta, Ga., Centers for Disease Control and Prevention, U.S. Department of Health and Human Services, 2005. Another 54 million people have some form of pre-diabetes and many will progress to frank diabetes within three years. See, e.g., National diabetes fact sheet. Atlanta, Ga., Centers for Disease Control and Prevention, U.S. Department of Health and Human Services, 2005; Cowie C C, Rust K F, Byrd-Holt D D, Eberhardt M S, Flegal K M, Engelgau M M, Saydah S H, Williams D E, Geiss L S, Gregg E W: Prevalence of diabetes and impaired fasting glucose in adults in the U.S. population: National Heath And Nutrition Examination Survey 1999-2002. Diabetes Care 29:1263-8, 2006; Knowler W C, Barrett-Connor E, Fowler S E, Hamman R F, Lachin J M, Walker E A, Nathan D M; Diabetes Prevention Program Research Group: Reduction in the incidence of type 2 diabetes with lifestyle intervention or metformin. N Engl J Med 346: 393-403, 2002. Numerous studies have shown that with early detection and effective intervention, diabetes can be prevented or delayed. See, e.g., Cowie C C, Rust K F, Byrd-Holt D D, Eberhardt M S, Flegal K M, Engelgau M M, Saydah S H, Williams D E, Geiss L S, Gregg E W: Prevalence of diabetes and impaired fasting glucose in adults in the U.S. population: National Health And Nutrition Examination Survey 1999-2002. Diabetes Care 29:1263-8, 2006; Knowler W C, Barrett-Connor E, Fowler S E, Hamman R F, Lachin J M, Walker E A, Nathan D M; Diabetes Prevention Program Research Group: Reduction in the incidence of type 2 diabetes with lifestyle intervention or metformin. N Engl J Med 346: 393-403, 2002; Tuomilehto J, Lindstrom J, Eriksson J G, Valle T T, Hamalainen H, Ilanne-Parikka P, Keinanen-Kiukaanniemi S, Laakso M, Louheranta A, Rastas M, Salminen V, Uusitupa M; Finnish Diabetes Prevention Study Group: Prevention of type 2 diabetes mellitus by changes in lifestyle among subjects with impaired glucose tolerance. N Engl J Med 344:1343-50, 2001; DREAM (Diabetes REduction Assessment with ramipril and rosiglitazone Medication) Trial investigators: Gerstein H C, Yusuf S, Bosch J, Pogue J, Sheridan P, Dinccag N, Hanefeld M, Hoogwerf B, Laakso M, Mohan V, Shaw J, Zinman B, Holman R R: Effect of rosiglitazone on the frequency of diabetes in patients with impaired glucose tolerance or impaired fasting glucose: a randomized controlled trial. Lancet 368: 1096-1105, 2006; Pan X R, Li G W, Hu Y H, Wang J X, Yang W Y, An Z X, Hu Z X, Lin J, Xiao J Z, Cao H B, Liu P A, Jiang X G, Jiang Y Y, Wang J P, Zheng H, Zhang H, Bennett P H, Howard B V: Effects of diet and exercise in preventing NIDDM in people with impaired glucose tolerance: The Da Qing IGT and Diabetes Study. Diabetes Care 20:537-544, 1997; Chiasson J L, Josse R G, Gomis R, Hanefeld M, Karasik A, Laakso M; STOP-NIDDM Trail Research Group: Acarbose for prevention of type 2 diabetes mellitus: the STOP-NIDDM randomized trial. Lancet 359: 2072-2077, 2002. In patients with diagnosed diabetes, other studies have shown that glucose control can lower the incidence of complications. See, e.g., The Diabetes Control and Complications Trial Research Group: The effect of intensive treatment of diabetes on the development and progression of long-term complications in insulin-dependent diabetes mellitus. N Engl J Med 329:977-986, 1993; UK Prospective Diabetes Study (UKPDS) Group: Intensive blood-glucose control with sulphonylureas or insulin compared with conventional treatment and risk of complications in patients with type 2 diabetes (UKPDS 33). Lancet 352:837-853, 1998.

Diagnosis is typically initiated during a physical exam with a primary care physician. However, current screening methods for type 2 diabetes and pre-diabetes are inadequate due to their inconvenience and inaccuracy. Specifically, the most widely applied screening test in the U.S., the fasting plasma glucose (FPG), has convenience barriers in the form of an overnight fast and a blood draw. FPG also suffers from poor sensitivity (40-60%) contributing to late diagnoses. See, e.g., Engelgau M M, Narayan K M, Herman W H: Screening for Type 2 diabetes. Diabetes Care 23:1563-1580, 2000. In fact, about one-half of diabetes patients present with one or more irreversible complications at the time of diagnosis. See, e.g., Harris M I, Eastman R C: Early detection of undiagnosed diabetes mellitus: a US perspective. Diabetes Metab Res Rev 16:230-236, 2001; Manley S M, Meyer L C, Neil H A W, Ross I S, Turner R C, Holman R R: UKPDS 6—Complications in newly diagnosed type 2 diabetic patients and their association with different clinical and biologic risk factors. Diabetes Res 13:1-11, 1990. A more accurate and convenient screening method could dramatically improve early detection of type 2 diabetes and its precursors, facilitating interventions that can prevent or at least delay the development of type 2 diabetes and its related micro and macrovascular complications.

Several studies including DCCT and EDIC have demonstrated that elevated skin advanced glycation endproducts (AGEs) are biomarkers of diabetes, highly correlated with the complications of diabetes and are predictive of future diabetic retinopathy and nephropathy. See, e.g., Monnier V M, Bautista O, Kenny D, Sell D R, Fogarty J, Dahms W, Cleary P A, Lachin J, Genut; DCCT Skin Collagen Ancillary Study Group: Skin collagen glycation, glycoxidation, and crosslinking are lower in subjects with long-term intensive versus conventional therapy of type 1 diabetes: relevance of glycated collagen products versus HbA1c as markers of diabetic complications. Diabetes 48:870-880, 1999; Genuth S, Sun W, Cleary P, Sell D R, Dahms W, Malone J, Sivitz W, Monnier V M; DCCT Skin Collagen Ancillary Study Group: Glycation and carboxymethyllysine levels in skin collagen predict the risk of future 10-year progression of diabetic retinopathy and nephropathy in the diabetes control and complications trial and epidemiology of diabetes interventions and complications participants with type 1 diabetes, Diabetes 54:3103-3111, 2005; Meerwaldt R, Links T P, Graaff R, Hoogenberg K, Lefrandt J D, Baynes J W, Gans R O, Smit A J: Increased accumulation of skin advanced glycation endproducts precedes and correlates with clinical manifestation of diabetic neuropathy. Diabetologia 48:1637-44, 2005. A person with diabetes will accumulate skin AGEs faster than individuals with normal glucose regulation. See, e.g., Monnier V M, Vishwanath V, Frank K E, Elmets C A, Dauchot P, Kohn R R: Relation between complications of type 1 diabetes mellitus and collagen-linked fluorescence. N Engl J Med 314:403-8, 1986. Thus, skin AGEs constitute a sensitive, summary metric for the integrated glycemic exposure that the body has endured.

However, until the recent development of novel noninvasive technology to measure advanced glycation endproducts, a punch biopsy was required to quantity skin AGE levels. This method for "Spectroscopic measurement of dermal Advance Glycation Endproducts"—hereafter referred to as SAGE— measures skin fluorescence due to AGEs in vivo and provides a quantitative diabetes risk score based on multivariate algorithms applied to the spectra. See; e.g., Hull E L, Ediger M N, Brown C D, Maynard J D, Johnson R D: Determination of a measure of a glycation end-product or disease state using tissue fluorescence. U.S. Pat. No. 7,139,598, incorporated herein by reference. SAGE does not require fasting and creates no biohazards. It can automatically compensate for subject-specific skin differences caused by melanin, hemoglobin, and light scattering. The measurement time can be approximately one minute and thus can provide an immediate result.

The concept of quantifying dermal AGEs noninvasively was successfully tested in a previous in vitro study. In that work, concentrations of a well-studied fluorescent AGE, pentosidine, were accurately quantified in a porcine dermis model by noninvasive fluorescence spectroscopy. See, e.g., Hull E L, Ediger M N, Unione A H T, Deemer E K, Stroman M L and Baynes J W: Noninvasive, optical detection of diabetes: model studies with porcine skin. Optics Express 12:4496-4510, 2004. Subsequently, an early noninvasive prototype was evaluated in a diabetic vs. normal (case-control) human subject study, demonstrating that SAGE could accurately classify disease in a case-control population. See, e.g., Ediger M N, Fleming C M, Rohrscheib M, Way J F, Nguyen C M and Maynard J D: Noninvasive Fluorescence Spectroscopy for Diabetes Screening: A Clinical Case-Control Study (Abstract). Diabetes Technology Meeting. San Francisco, Calif., 2005, incorporated herein by reference.

A noninvasive method and apparatus for detecting disease in an individual using fluorescence spectroscopy and multivariate analysis has been previously disclosed in U.S. Pat. No. 7,139,598, incorporated herein by reference. Continued development of this method and apparatus has resulted in significant instrument and algorithm improvements that yield increased accuracy for noninvasively detecting disease, especially type 2 diabetes and pre-diabetes. The instrument improvements provide higher overall signal to noise ratio, reduced measurement time, better reliability, lower cost and reduced size compared to instruments disclosed in the art. The algorithmic improvements improve overall accuracy by more effective extraction of the information needed for accurate noninvasive detection of disease using fluorescence spectroscopy. These instrument and algorithm improvements are described herein, and have been tested in a large clinical study also described herein.

SUMMARY OF THE INVENTION

Embodiments of the present invention provide an apparatus suitable for determining properties of in vivo tissue from spectral information collected from the tissue. An illumination system provides light at a plurality of broadband ranges, which are communicated to an optical probe. The optical probe receives light from the illumination system and transmits it to in vivo tissue, and receives light diffusely reflected in response to the broadband light, emitted from the in vivo tissue by fluorescence thereof in response to the broadband light, or a combination thereof. The optical probe communicates the light to a spectrograph which produces a signal representative of the spectral properties of the light. An analysis system determines a property of the in Vivo tissue from the spectral properties. A calibration device mounts such that it is periodically in optical communication with the optical probe.

Embodiments of the present invention provide an apparatus suitable for determining a disease state or state of health, such as the presence of diabetes, pre-diabetes, or both, from spectral information collected from the tissue. An illumination system provides light at a plurality of broadband ranges, which are communicated to an optical probe. The optical probe receives light from the illumination system and transmits it to in vivo tissue, and receives tight diffusely reflected in response to the broadband light, emitted from the in vivo tissue by fluorescence thereof in response to the broadband light, or a combination thereof. The optical probe communicates the light to a spectrograph which produces a signal representative of the spectral properties of the light. An analysis system determines a properly of the in vivo tissue from the spectral properties. A calibration device mounts such that it is periodically in optical communication with the optical probe.

Some embodiments include a plurality of light emitting diodes (LEDs) in the illumination system, and can include at least one filter that substantially rejects light from the LEDs that has the same wavelength of a wavelength of light fluoresced by materials of interest in the tissue. Some embodiments include one or more light pipes that encourage uniform illumination by the illumination system or by the optical probe. Some embodiments include movably mounted LEDs, such as by rotation of a carrier, to allow selective coupling of different LEDs to the optical probe. Some embodiments include specific operator displays. Some embodiments include optical fibers in the optical probe, which fibers are arranged to provide specific relationships between illumination of the tissue and collection of light from the tissue.

The present invention can also provide methods of determining a disease state, such as the presence of diabetes, pre-diabetes, or both, from spectral information collected from in vivo human tissue. The methods can include biologic information concerning the subject with spectral information collected using an apparatus such as that described herein. Some embodiments of the methods determine a group to which a subject belongs, at least in part based on the spectral information acquired. A model relating spectral information to disease state for the determined group can then be used to determine the disease state of the subject. The groups can correspond to skin pigmentation, or gender, as examples.

BRIEF DESCRIPTION OF THE DRAWINGS

FIG. 11a is a front isometric view of an illumination system suitable for use in the present invention.

FIG. 11b is a back isometric view of an illumination system suitable for use in the present invention.

FIG. 12 is an isometric view of a portion of a wheel assembly suitable for use in the example illumination system of FIG. 11 and FIG. 11b.

FIG. 13 is a schematic cross-sectional view of an illumination system having the two illumination channels.

FIG. 14 is an isometric view of an example embodiment of a trifurcated optical probe having two input illumination channels and one detection channel.

FIG. 15 is a schematic depiction of optical fibers in an example optical probe according to the present invention providing two different illumination-collection characteristics.

FIG. 16 is a schematic depiction of an example spectrograph suitable for use in the present invention.

FIG. 17 is an illustration of an example image formed onto a CCD image sensor with multiple wavelengths of 360, 435, 510, 585, and 660 nm, and the corresponding spectrum produced by vertically binning the pixels of the CCD.

DETAILED DESCRIPTION OF THE INVENTION

Clinical Study Research Design and Methods

Figure 1:
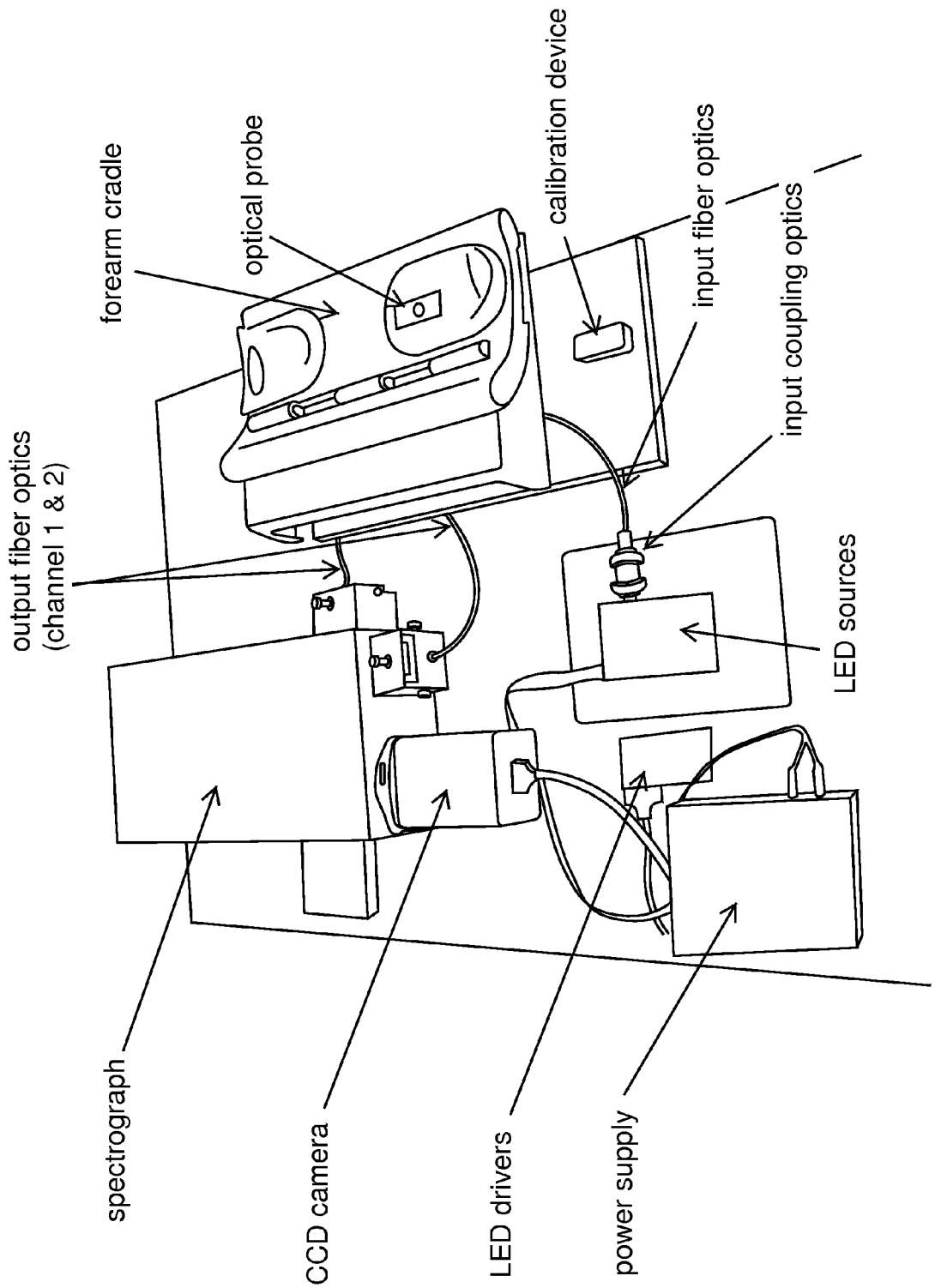
FIG. 1 is an illustration of an example embodiment of the present invention.

Embodiments of the present invention have been tested in a large clinical study, conducted to compare SAGE with the fasting plasma glucose (FPG) and glycosylated hemoglobin (A1c), using the 2-hour oral glucose tolerance test (OGTT) to determine truth (i.e., the "gold standard"). The threshold for impaired glucose tolerance (IGT)—a 2-hour OGTT value of 140 mg/dL or greater—delineated the screening threshold for "abnormal glucose tolerance." A subject was classified as having abnormal glucose tolerance if they screen positive for either IGT (OGTT: 140-199 mg/dL) or type 2 diabetes (OGTT: ≧200 mg/dL). The abnormal glucose tolerance group encompasses all subjects needing follow-up and diagnostic confirmation. The study was conducted in a naïve population—subjects who have not been previously diagnosed with either type 1 or 2 diabetes.

In order to demonstrate superior sensitivity at 80% power with 95% confidence, an abnormality in 80 subjects was required. See, e.g., Schatzkin A, Connor R J, Taylor P R, Bunnag B: Comparing New and Old Screening Tests When a Reference Procedure Cannot Be Performed On All Screenees: Example Of Automated Cytometry For Early Detection Of Cervical Cancer. Am. J. Epidemiol 125:672-678, 1987. At that prevalence and for a projected SAGE sensitivity of 68%, the power calculations yield a 95% confidence interval for test sensitivity of 57.8%-78.2%.

Study subjects were selected from persons who responded to flyers and newspaper advertising. Subjects were recruited until the target prevalence of abnormal glucose tolerance was comfortably achieved. Selection criteria were one or more risk factors for diabetes per the American Diabetes Association (ADA) standard of care guidelines. See, e.g., Standards of Medical Care in Diabetes—2006. Diabetes Care, 29(Supplement 1):S4-S42, 2006. Individuals with a previous diagnosis of type 1 or type 2 diabetes were excluded. Ages in the cohort ranged between 21 and 86 years while the ethnic and racial composition mirrored the demographics of Albuquerque, N. Mex. The cohort demographics are summarized in Table 1. The study protocol was approved by the University of New Mexico School of Medicine Human Research Review Committee. When recruiting concluded, 84 subjects with abnormal glucose tolerance had been identified within a cohort of 351 participants.

Subjects were asked to fast overnight for a minimum of 8 hours prior to participation. All provided their informed consent. Blood was drawn from subjects for clinical chemistry tests. The glucose assays were run on a Vitros 950TM clinical chemistry analyzer while the A1c assay was performed on a Tosoh G7 HPLCTM. The assays adhered to internal standard operating procedures. See, e.g., "CHEM-081: Glucose, Serum or CSF by Vitros Slide Technology" or "HEM-003: Hemoglobin A1C, Tosho G7.".

TABLE 1

Summary of study demographics
Study Demographics (n = 351)

| Age (yrs) | | Gender | | Ethnicity | |
|---|---|---|---|---|---|
| 21-30 | 4.8% | Male | 36.5% | Caucasian | 53.3% |
| 31-40 | 14.8% | Female | 63.5% | Hispanic | 36.5% |
| 41-50 | 28.2% | | | African Am | 3.1% |
| 51-60 | 25.1% | | | Native Am | 4.8% |
| 61-70 | 18.5% | | | Asian | 0.9% |
| 71-80 | 6.3% | | | East Indian | 0.3% |
| 81+ | 2.3% | | | Other | 1.1% |

The prototype SAGE instrument is a table-top apparatus. The subject sits in a chair beside the instrument and rests his/her left forearm in an ergonomically-designed cradle. A custom fiber-optic probe couples output from near-ultraviolet and blue light-emitting diodes to the subject's volar forearm and collects the resulting skin fluorescence and diffuse reflectance. The optical radiation emitted from the skin is dispersed in a modified research-grade spectrometer and detected by a charge-coupled device (CCD) array detector.

The optical exposure from SAGE was compared to the International Electrotechnical Commission (IEC) ultraviolet skin exposure limits. See, e.g., Safety of laser products—Part 9: Compilation of maximum permissible exposure to incoherent optical radiation. International Electrotechnical Commission, 1999 (IEC/TR 60825-9:1999). Skin exposure from the screening device was a factor of 250 times smaller than the exposure limit. Hence, the risk of skin erythema or other damage due to optical radiation from the SAGE is negligible.

Melanin and hemoglobin are optical absorbers at the wavelengths of interest and reduce light amplitude and distort the skin's spectral characteristics. In addition, subject-specific tissue characteristics such as wrinkles, dermal collagen concentration and organization, and hair follicles scatter light in the skin. Previous studies developed techniques that were applied in the prototype instrument to mitigate the impact of skin pigmentation, hemoglobin content and light scattering on the noninvasive measurement. See, e.g., Hull E L, Ediger M N, Unione A H T, Deemer E K, Stroman M L and Baynes J W: Noninvasive, optical detection of diabetes: model studies with porcine skin. Optics Express 12:4496-4510, 2004, incorporated herein by reference. Also, skin AGEs accumulate naturally overtime in all people. An algorithm compensated for patient age to remove this trend. Principal-components analysis (PCA) was applied to the spectra from 267 subjects with normal glucose regulation with ages ranging 22-85 years. PCA reduces the dimensionality of the data set, transforming the fluorescence spectra into eigenvalues and eigenvectors. See, e.g. Kramer R: Chemometric Techniques for Quantitative Analysis. New York, Marcel Dekker, 1998. Linear regression determined the age-related slope of the eigenvalues. The age-dependence is then removed from all spectra to compensate for subject age. The pigmentation and age corrected spectra comprise the 'intrinsic' dermal fluorescence spectra.

Linear-discriminant-analysis (LDA) was applied to the intrinsic spectra to assess noninvasive disease classification performance. See, e.g., McLachlan G L: Discriminant Analysis and Statistical Pattern Recognition. New York, Wiley Interscience, 1992. In this method, the intrinsic dermal fluorescence spectra were first decomposed by PCA. From the resulting spectral scores, multi-dimensional spectral distances were determined. These distances (Mahalanobis distances) represent the effective distance of each spectra with respect to the normal (D0) and abnormal groups (D1). From the difference between the distances (D1-D0), posterior probabilities ranging from 0 to 100 are computed. A posterior probability—the SAGE output value—represents a likelihood metric for that subject belonging to the abnormal class.

Subjects were measured twice by SAGE in order to assess any effect due to subject fasting status. The first SAGE measurement always occurred in a fasting state. Approximately 60% of the study cohort received both FPG and OGTT during a single visit. For the remaining group, the OGTT was administered on a subsequent day. For all subjects, their second SAGE measurement was obtained at least one hour after ingestion of the glucose load—near the anticipated peak of the acute blood glucose level due to the OGTT glucose bolus. Subject convenience dictated whether they participated via one or two visits. In all cases, subjects were in a non-fasting state during their second SAGE measurement. In principle, SAGE should be independent of fasting status since AGE accumulation is not influenced by acute blood glucose levels. SAGE dependence on fasting status was empirically assessed by comparing classification performance stratified by first versus second measurement.

To quantitatively assess the impact of skin coloration on the non invasive classification performance, subject skin pigmentation was objectively quantified from diffuse reflectance measurements and classified into light and dark subgroups. Noninvasive disease classification performance was then evaluated for each subgroup.

The screening performance of FPG, A1c and SAGE were assessed by comparing their respective sensitivities at a relevant clinical threshold. An appropriate comparative threshold for screening is the FPG threshold for impaired fasting glucose (IFG). All three tests were evaluated at the specificity corresponding to this FPG value (100 mg/dL).

Clinical Study Results

Figure 21:
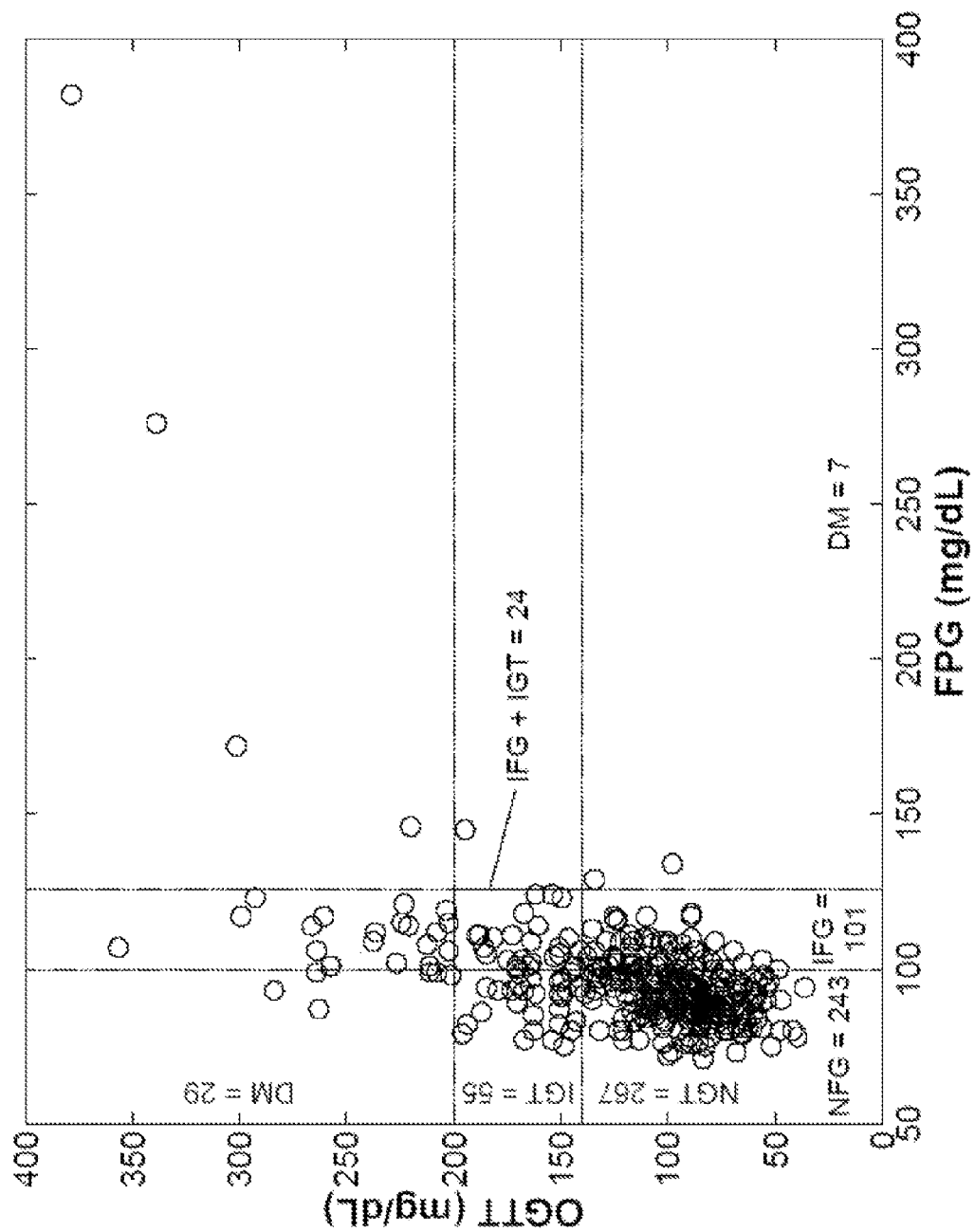
FIG. 21 is an illustration of a comparison of OGTT and FPG screening categorization obtained using the present invention.

The OGTT identified abnormal glucose tolerance in 84 of the 351 subjects (23.9% prevalence). Of the 84 subjects with abnormal glucose tolerance, IGT was found in 55 subjects and frank type 2 diabetes in 29 subjects. A comprehensive comparison of OGTT and FPG screening categorization is presented in FIG. 21.

Figure 22:
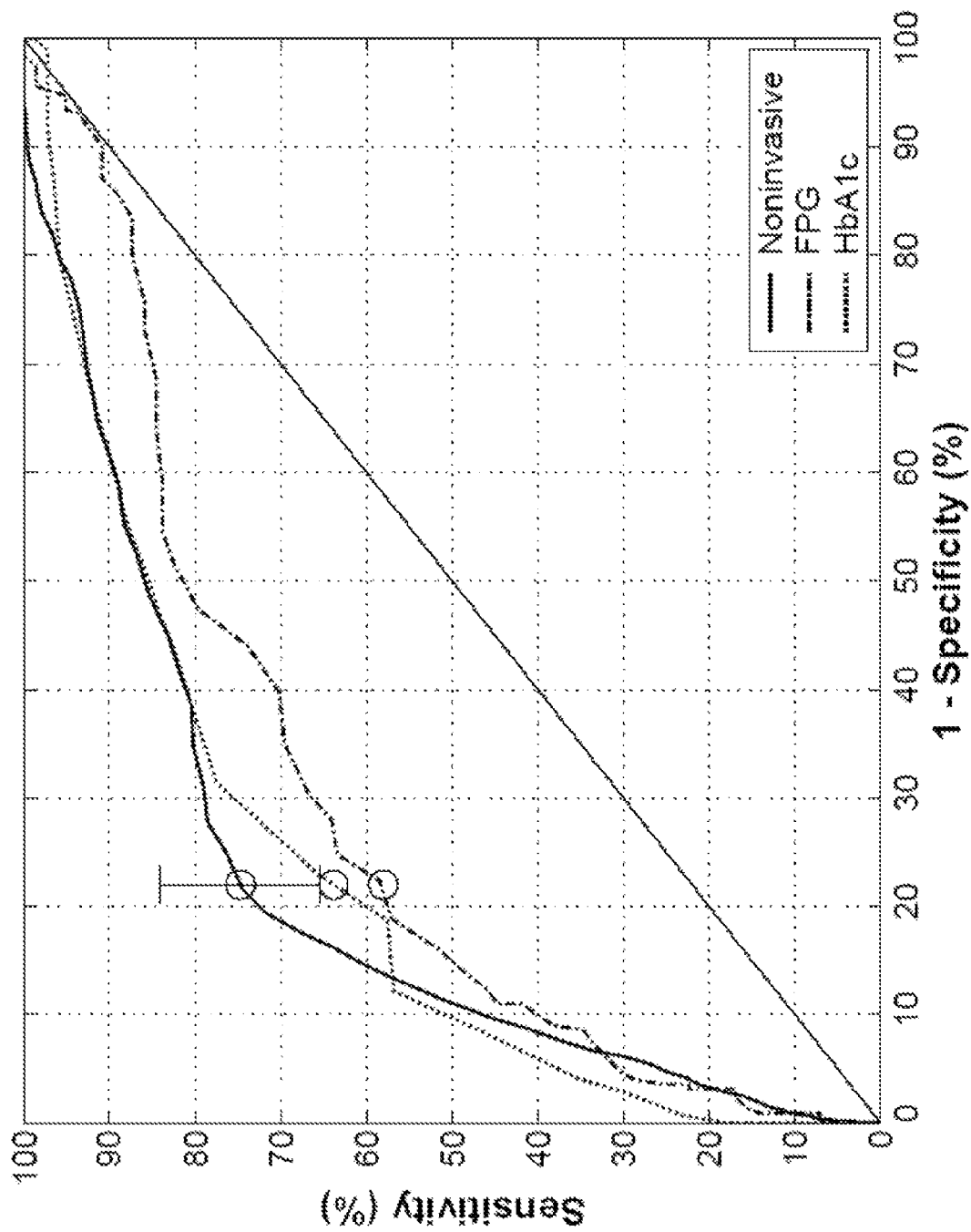
FIG. 22 is an illustration of receiver-operator characteristics obtained using the present invention.

Using the normal vs. abnormal classification determined by OGTT, the receiver-operator characteristics for FPG, A1c and SAGE were computed. The IFG threshold of 100 mg/dL corresponds to a FPG specificity of 77.4%—the critical specificity for comparing the tests. At 77.4% specificity, the FPG sensitivity was 58.0%, the A1c sensitivity was 63.8% and SAGE sensitivity was 74.7%. The test values corresponding to the critical specificity were 100 mg/dL for FPG, 5.8% for A1c and 50 for SAGE. Test performance is summarized in Table 2. The 95% confidence interval for SAGE sensitivity was 65.4%-84%. Thus, the sensitivity differences between SAGE and both FPG and A1c are statistically significant ($p<0.05$). The actual confidence interval differs from that estimated by the power calculations in the methods section, since the study found higher prevalence and increased SAGE sensitivity at the IFG-defined critical specificity. The absolute sensitivity advantage of the noninvasive device compared to FPG and A1c were 16.7 and 10.9 percentage points, respectively. The relative sensitivity advantage for SAGE versus FPG was 28.8%, and for A1c the relative advantage was 17.1%. These values estimate the additional fraction of abnormal glucose tolerance subjects that are detected by SAGE but are missed by the conventional blood tests. The results are plotted as receiver-operator characteristics (ROCs) in FIG. 22.

TABLE 2

Summary of Test Performance

| Test | Sensitivity | Threshold |
|---|---|---|
| SAGE | 74.7% | 50 |
| FPG | 58.0% | 100 mg/dL |
| A1c | 63.8% | 5.8% |

| SAGE Sensitivity Advantage | |
|---|---|
| Absolute | Relative |
| 16.7% | 28.8% |
| 10.9% | 17.1% |

Comparison of sensitivities for SAGE, FPG and A1c for detecting abnormal glucose tolerance. The FPG threshold for IGT (100 mg/dL) set the critical specificity (77.4%) for this comparison. Thresholds for each test at the critical specificity are indicated. The right section notes the performance advantage of SAGE over the two blood-based tests in terms of absolute and relative sensitivity.

The general performance metric of area-under-the-curve (AUC) shows a statistically significant advantage ($p<0.05$) for SAGE (AUC=79.7%) vs. the FPG (72.1%). The AUC values for SAGE (79.7%) vs. A1c (79.2%) were not statistically separable. SAGE performance was assessed for high and low melanin concentration sub-groups that were divided by their measured skin diffuse reflectance. At IFG threshold noted above (critical specificity=77.4%), sensitivity for detecting abnormal glucose tolerance in subjects with tighter skin was 70.1%, while in those with darker skin it was 82.1%. Compared to the results for the entire cohort, the performance for sub-cohorts stratified by skin melanin content are not statistically different. In other words, SAGE sensitivity is not impaired by inter-subject skin melanin variations.

Classification performance was also stratified by subject fasting status. SAGE sensitivity for first session (fasting) was 78.4%, while the sensitivity for second session values (non-fasting) was 72.7%. The session-stratified sensitivities are not significantly different from that of the full cohort. Alternatively, the correlation coefficient between fasting and non-fasting SAGE measurements was $r=0.87$ ($p<0.001$). Consequently, the SAGE performance is independent of the ambient blood glucose level.

Clinical Study Conclusions

SAGE significantly out-performs FPG and A1c for detection of abnormal glucose tolerance. SAGE identified ~29% more individuals with undiagnosed abnormal glucose tolerance than FPG and ~17% more than A1c. In addition, SAGE provides rapid results and does riot require fasting or blood draws—factors that are convenience barriers to opportunistic screening.

The low sensitivity for FPG reported here is in good agreement with previous estimates for its screening sensitivity. See, e.g., Engelgau M M, Narayan K M, Herman W H: Screening for Type 2 diabetes. Diabetes Care 23:1563-1580, 2000. Since negative screening results are not subject to confirmatory testing, the large false-negative rate for FPG is a latent problem and contributes to the growing number of undiagnosed 'silent' cases of type 2 diabetes. Given the increasing worldwide prevalence of type 2 diabetes and pre-diabetes, a move to earlier detection and treatment is necessary to help mitigate the diabetes epidemic. In the United States, if current trends continue the prevalence of diabetes is expected to more than double by 2025 and affect 15% of the population. See, e.g., Barriers to Chronic Disease Care in the United States of America: The Case of Diabetes and its Consequences. Yale University Schools of Public Health and Medicine and the Institute for Alternative Futures, 2005. The recent estimate of $135 billion for annual diabetes-related healthcare costs in the United States means that the costs of the diabetes epidemics threatens to overwhelm the nation's healthcare system. See, e.g., Hogan P, Dall T, Nikolov P: Economic Costs of Diabetes in the U.S. in 2002. Diabetes Care 26:917-932, 2003.

Fortunately, once detected, diabetes is now more treatable than ever before. Large clinical studies such as the DCCT and UKPDS have shown that tight control of glucose levels has significant health benefits to those with established diabetes. See, e.g., The Diabetes Control and Complications Trial Research Group: The effect of intensive treatment of diabetes on the development and progression of long-term complications in insulin-dependent diabetes mellitus. N Engl J Med 329:977-986, 1993; UK Prospective Diabetes Study (UK-PDS) Group: Intensive blood-glucose control with sulphonylureas or insulin compared with conventional treatment and risk of complications in patients with type 2 diabetes (UK-PDS 33). Lancet 352:837-853, 1998.

Moreover, if pre-diabetes is detected and treated, progression to frank type 2 diabetes can be delayed or prevented. The DPP, FDPS and DREAM trials have shown that it is possible to prevent or at least delay the development of type 2 diabetes in patients with pre-diabetes. See, e.g., Knowler W C, Barnett-Connor E, Fowler S E, Hamman R F, Lachin J M, Walker E A, Nathan D M; Diabetes Prevention Program Research Group: Reduction in the incidence of type 2 diabetes with lifestyle intervention or metformin. N Engl J Med 346: 393-403, 2002; Tuomilehto J, Lindstrom J, Eriksson J G, Valle T T, Hamalainen H, Ilanne-Parikka P, Keinanen-Kiukaanniemi S, Laakso M, Louheranta A, Rastas M, Salminen V, Uusitupa M; Finnish Diabetes Prevention Study Group: Prevention of type 2 diabetes mellitus by changes in lifestyle among subjects with impaired glucose tolerance. N Engl J Med 344: 1343-50, 2001; DREAM (Diabetes REduction Assessment with ramipril and rosiglitazone Medication) Trial Investigators; Gerstein H C, Yusuf S, Bosch J, Pogue J, Sheridan P, Dinccag N, Hanefeld M, Hoogwerf B, Laakso M, Mohan V, Shaw J, Zinman B, Holman R R: Effect of rosiglitazone on the frequency of diabetes in patients with impaired glucose tolerance or impaired fasting glucose: a randomized controlled trial. Lancet 368: 1096-1105, 2006. This can be accomplished with aggressive diet and exercise modification and/or therapeutics such as metformin (DPP) and rosiglitazone (DREAM).

The combination of accuracy and convenience of SAGE make it well-suited for opportunistic screening and earlier detection of diabetes and pre-diabetes. This noninvasive technology can facilitate early intervention for preventing or delaying the development of diabetes and its devastating complications.

Improved Instrumentation for Noninvasive Detection of Disease

Figure 2:
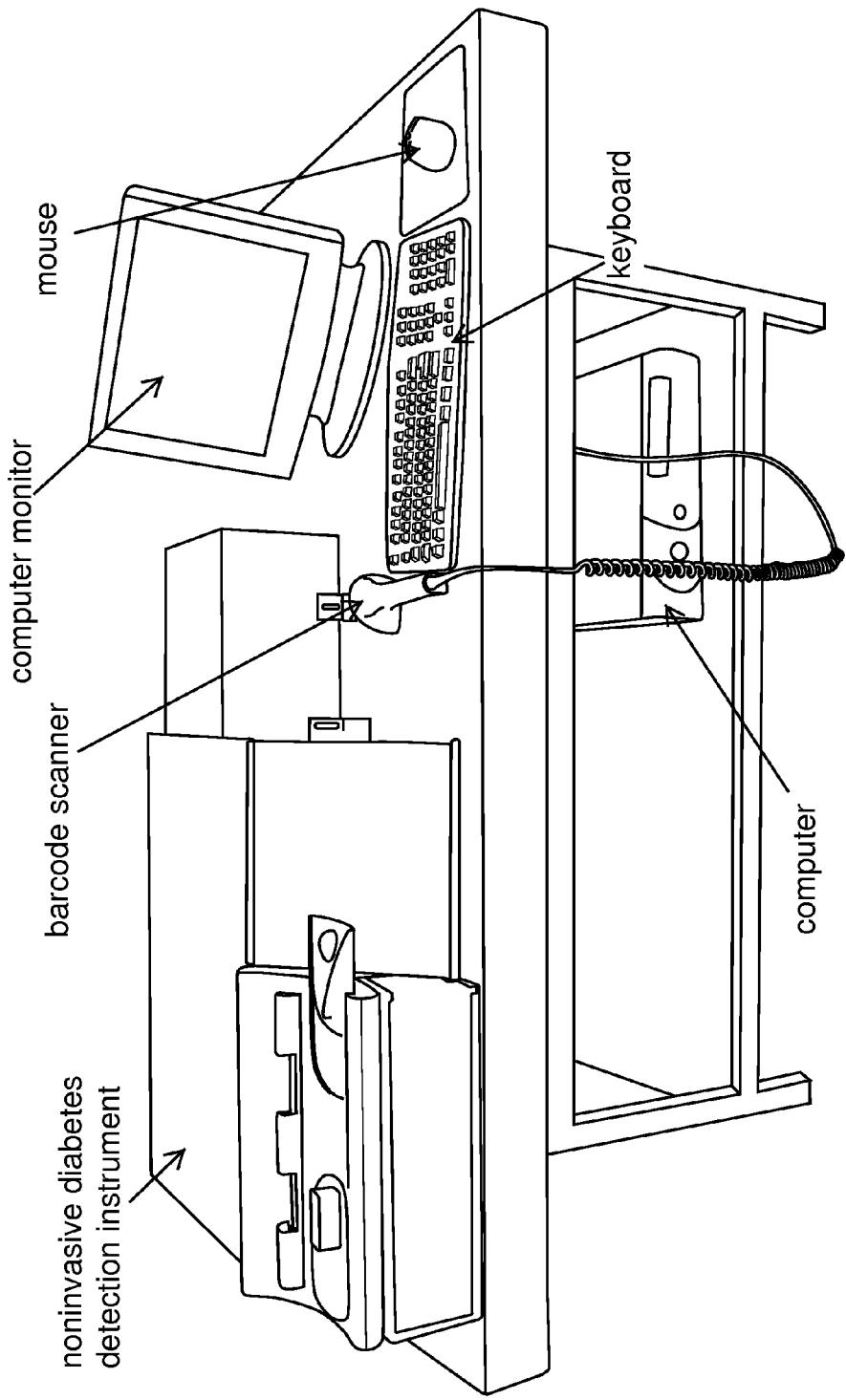
FIG. 2 is an illustration of an example embodiment of the present invention.

An apparatus according to the present invention can comprise an instrument specifically designed to use fluorescence and reflectance spectroscopy to noninvasively detect disease in an individual. FIG. 1 and FIG. 2 depict a representative embodiment of such an instrument and its major subsystems. Generally, the system includes a light source, an optical probe to couple light from the light source to an individual's tissue and to collect reflected and emitted light from the tissue, a forearm cradle to hold a subject's arm still during the optical measurement, a calibration device to place on the optical probe when instrument calibration is required, a spectrograph to disperse the collected light from the optical probe into a range of wavelengths, a CCD camera detection system that measures the dispersed tight from the tissue, a power supply, a computer that stores and processes the CCD camera images plus controls the overall instrument and a user interface that reports on the operation of the instrument and the results of the noninvasive measurement.

Figure 3:
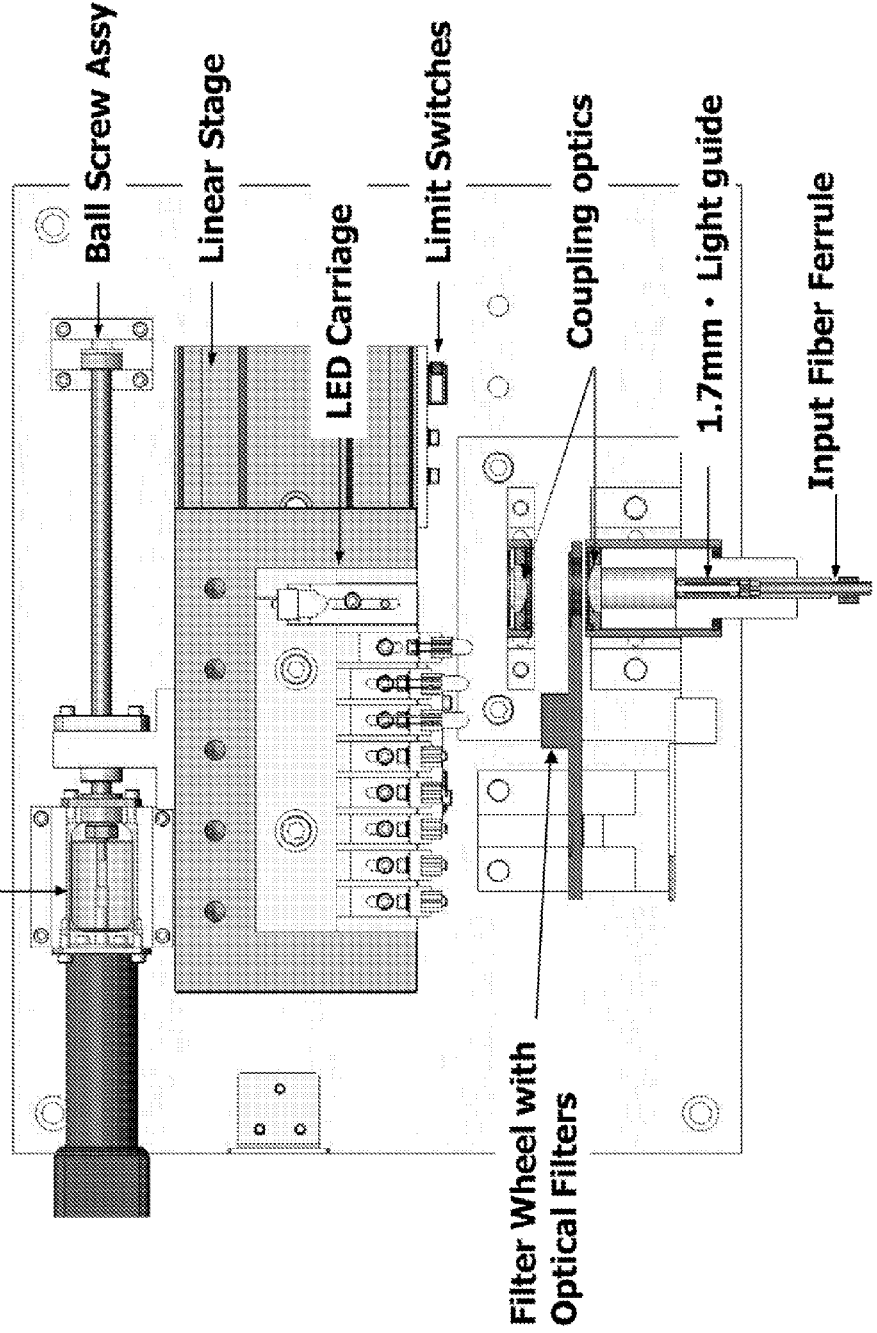
FIG. 3 is a schematic depiction of an illumination system suitable for use in the present invention.
Figure 6:
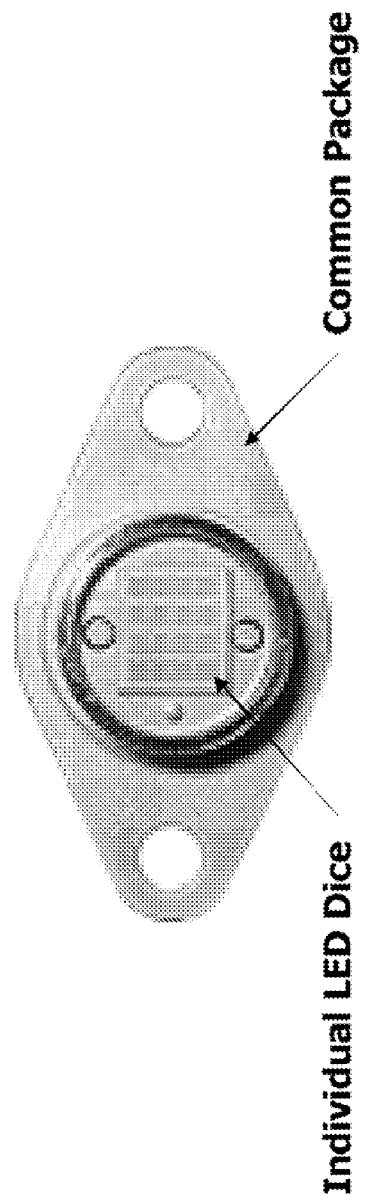
FIG. 6 is an illustration of an array of light emitting diodes suitable for use in an illumination system in the present invention.

The light source subsystem utilizes one or more light emitting diodes (LEDs) to provide the excitation light needed for the fluorescence and reflectance spectral measurements. The LEDs can be discrete devices as depicted in FIG. 3 or combined into a multi-chip module as shown in FIG. 6. Alternately, laser diodes of the appropriate wavelength can be substituted for one or more of the LEDs. The LEDs emit light in the wavelength range of 265 to 850 nm. In a preferred embodiment of the Scout light source subsystem the LEDs have central wavelengths of 375 nm, 405 nm, 420 nm, 435 nm and 460 nm, plus a white light LED is also used to measure skin reflectance.

The use of LEDs to excite fluorescence in the tissue has some unique advantages for noninvasive detection of disease. The relatively broad output spectrum of a given LED may excite multiple fluorophores at once. Mutivariate spectroscopy techniques (i.e. principle components analysis, partial least squares regression, support vector regression, etc.) can extract the information contained in the composite fluorescence spectrum (i.e. a superposition of multiple fluorescence spectra from the excited fluorophores) to achieve better disease detection accuracy. The broad LED output spectrum effectively recreates portions of and excitation-emission map. Other advantages of using LEDs are very low cost, high brightness for improved signal to noise ratio, reduced measurement time, power efficiency and increased reliability due to the long lifetimes of the LED devices.

As shown in FIG. 3, the LEDs are mechanically positioned in front on of the coupling optics by a motor and translation stage. A LED driver circuit turns on/off the appropriate LED when it is positioned in front of the coupling optics. The LED driver circuit is a constant current source that is selectively applied to a given LED under computer control. The output light of the chosen LED is collected by a lens that collimates the light and sends the collimated beam through a filter wheel.

The filter wheel contains one or more filters that spectrally limit the light from a given LED. The fitters can be bandpass or short pass type filters. They can be useful to suppress LED light leakage into the fluorescence emission spectral region. The filter wheel can also have a position without a filter for use with the white light LED or to measure unfiltered LED reflectance. If laser diodes are used instead of LEDs, the filter wheel and filters can be eliminated because of narrow spectral bandwidth of the laser diode does not significantly interfere with the collection of the fluorescence emission spectra.

Figure 4:
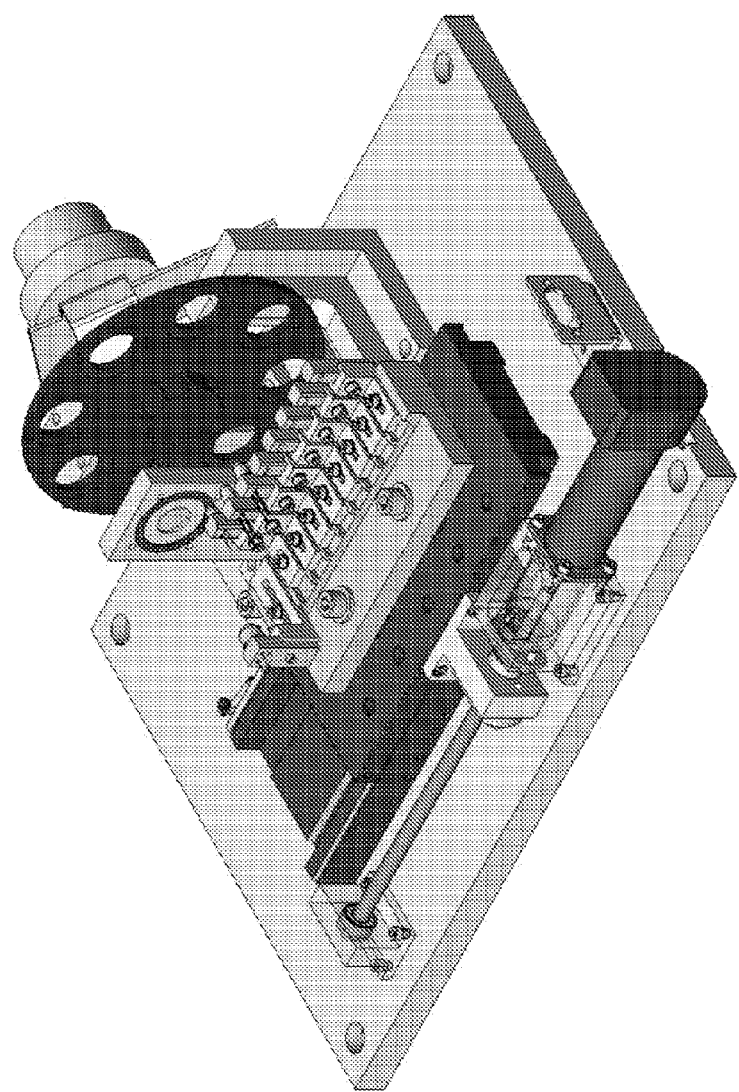
FIG. 4 is a schematic isometric view of an illumination system suitable for use in the present invention.
Figure 5:
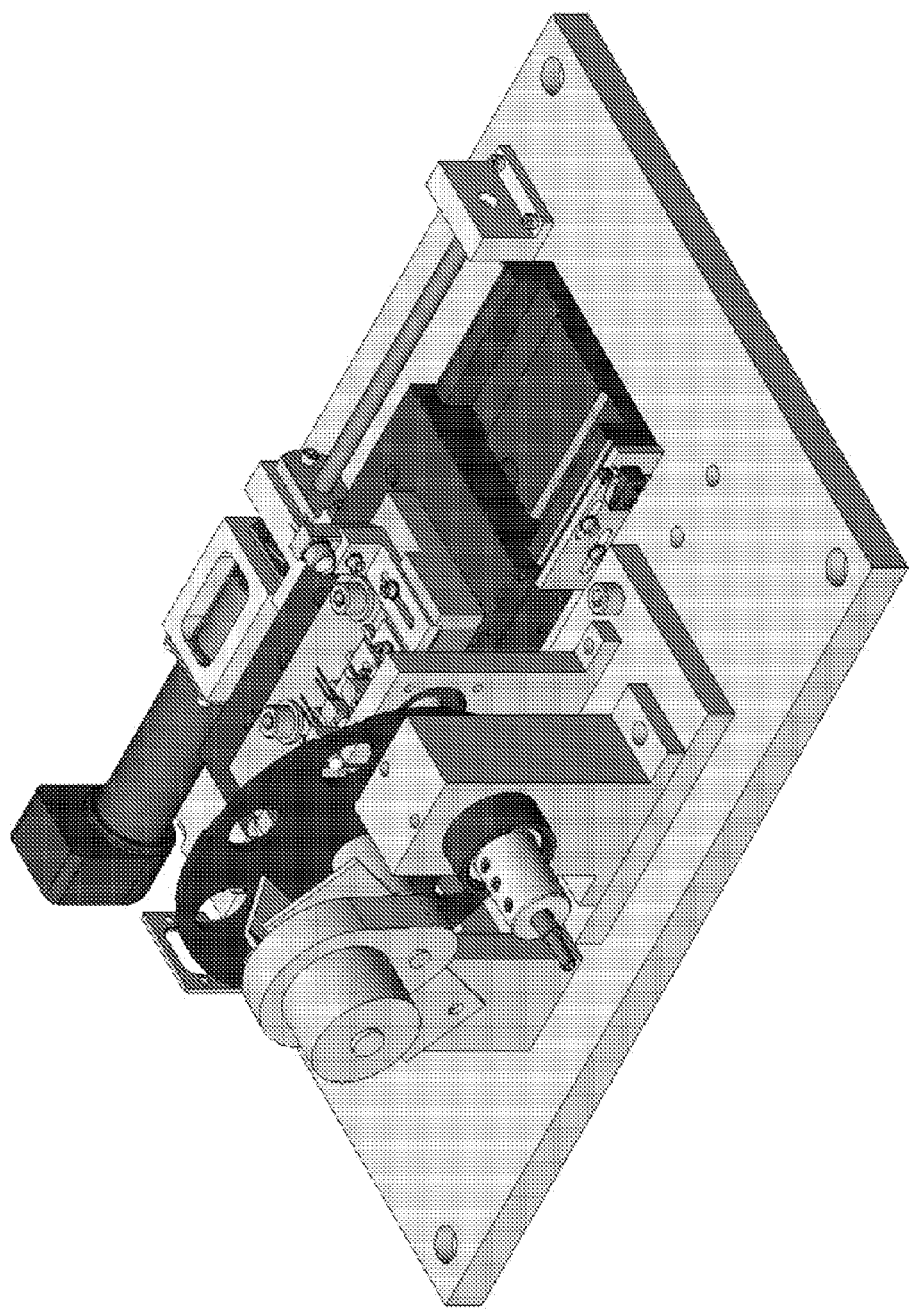
FIG. 5 is a schematic isometric view of an illumination system suitable for use in the present invention.

After light passes through the filter wheel, it is re-imaged by a second lens onto a light guide such as a square or rectangular light guide. The light guide scrambles the image from the LED and provides uniform illumination of the input fiber optic bundle of the optical probe. The optical probe input ferrule and the light guide can have a minimum spacing of 0.5 mm to eliminate optical fringing effects. The light guide can have at least a 5 to 1 length to width/height aspect ratio to provide adequate light scrambling and uniform illumination at the output end of the light guide. FIG. 4 and FIG. 5 show isometric views of an example light source subsystem.

In an alternate embodiment of the light source subsystem, a plurality of illumination channels can be formed in order to accommodate the coupling of light into multiple fiber optic bundles of an optical probe. FIG. 11a and FIG. 11b depict front and back isometric views of an example embodiment having two output illumination channels. A main body provides support about which a wheel assembly, motor, coupling optics, and fiber optic ferrules are attached. The wheel assembly, a portion of which is shown in FIG. 12, is used to capture the LEDs, filters, and other light sources (e.g. a neon lamp for calibration). The wheel assembly attaches to a shaft that allows for the LED and filter assembly to rotate about a central axis. The attachment can be a direct coupling of the drive gear and the wheel gear, or a belt drive/linkage arrangement can be used. The belt drive arrangement requires less precision in the gear alignment and quiet operation (no gear grinding or vibration from misalignment). A motor is used to rotate the wheel assembly to bring the desired light source into alignment with the coupling optics that defines either of the two output illumination channels.

FIG. 13 shows a line drawing of a cross-sectional view of the light source subsystem through the two illumination channels. Considering only the upper most of the two channels, light is emitted by the LED and immediately passes through a filter. The light is then collected by a lens and re-imaged onto a light guide. The light guide homogenizes the spatial distribution of the light at the distal end, at which point it is butt-coupled to a corresponding fiber optic bundle of the optical probe. A second channel, shown below the first channel, is essentially a reproduction of the first, but has a light guide sized differently to accommodate a smaller fiber bundle.

Figure 20:
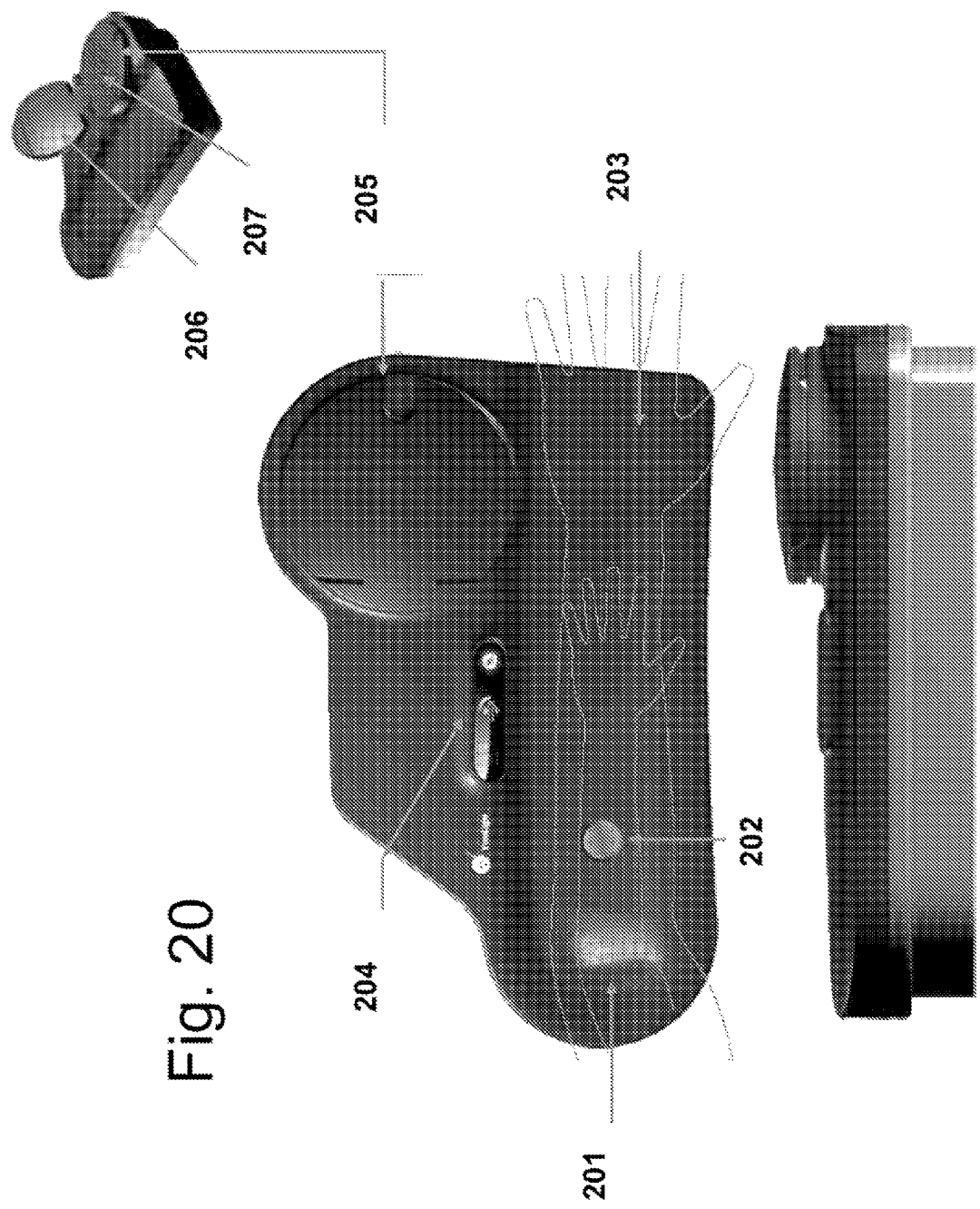
FIG. 20 is an illustration of an example embodiment of an apparatus according to the present invention.

The forearm cradle holds the optical probe and positions a subject's arm properly on the optical probe. The key aspects of the forearm cradle include an ergonomic elbow cup, an armrest and an extendable handgrip. The elbow cup, armrest and handgrip combine to register the forearm properly and comfortably over the optical probe. The handgrip keeps the fingers extended to ensure that forearm is relaxed and reduce muscle tension that might affect the optical measurement. It is also possible to remove the handgrip from the forearm cradle to simplify the instrument without sacrificing overall measurement accuracy. FIG. 20 is a schematic illustration of an example embodiment without a handgrip. In this embodiment, the optical probe is located approximately 3 inches from the elbow to better sample the meaty portion of the volar forearm and provide a good chance of establishing good contact between the volar forearm and the optical probe. This elbow cup/probe geometry allows measurement of a wide range of forearm sizes (2nd percentile female to 98th percentile male). FIG. 20 depicts a commercial embodiment of the instrument and illustrates the volar forearm measurement geometry between the elbow cup, optical probe and cradle. This version of the commercial embodiment does not have an extendable handgrip, but one could be added if desired.

Figure 7:
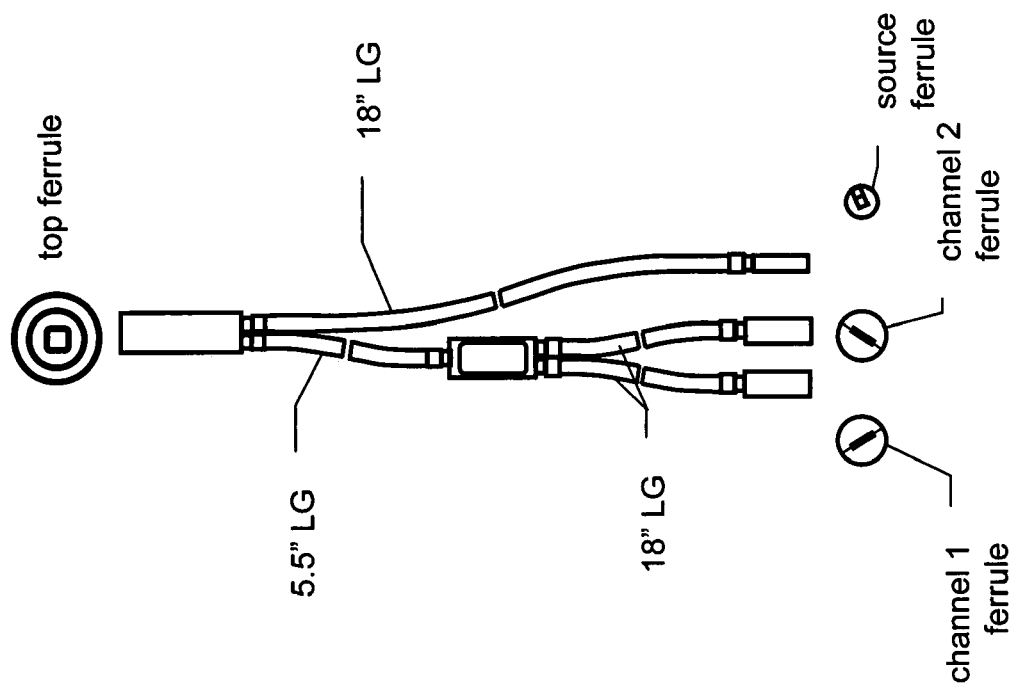
FIG. 7 is a schematic depiction of an optical probe suitable for use in the present invention.
Figure 8:
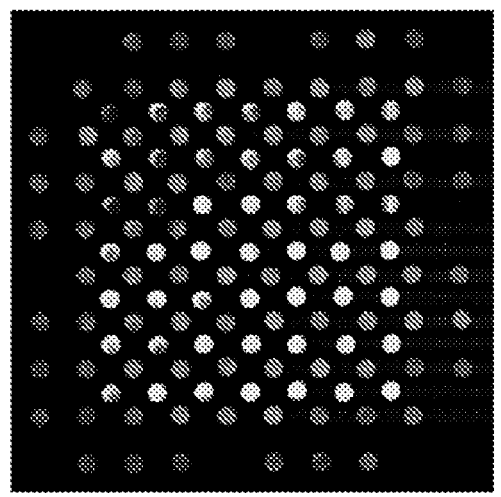
FIG. 8 is a schematic depiction of an optical probe suitable for use in the present invention, seen from the interface with the tissue.
Figure 9:
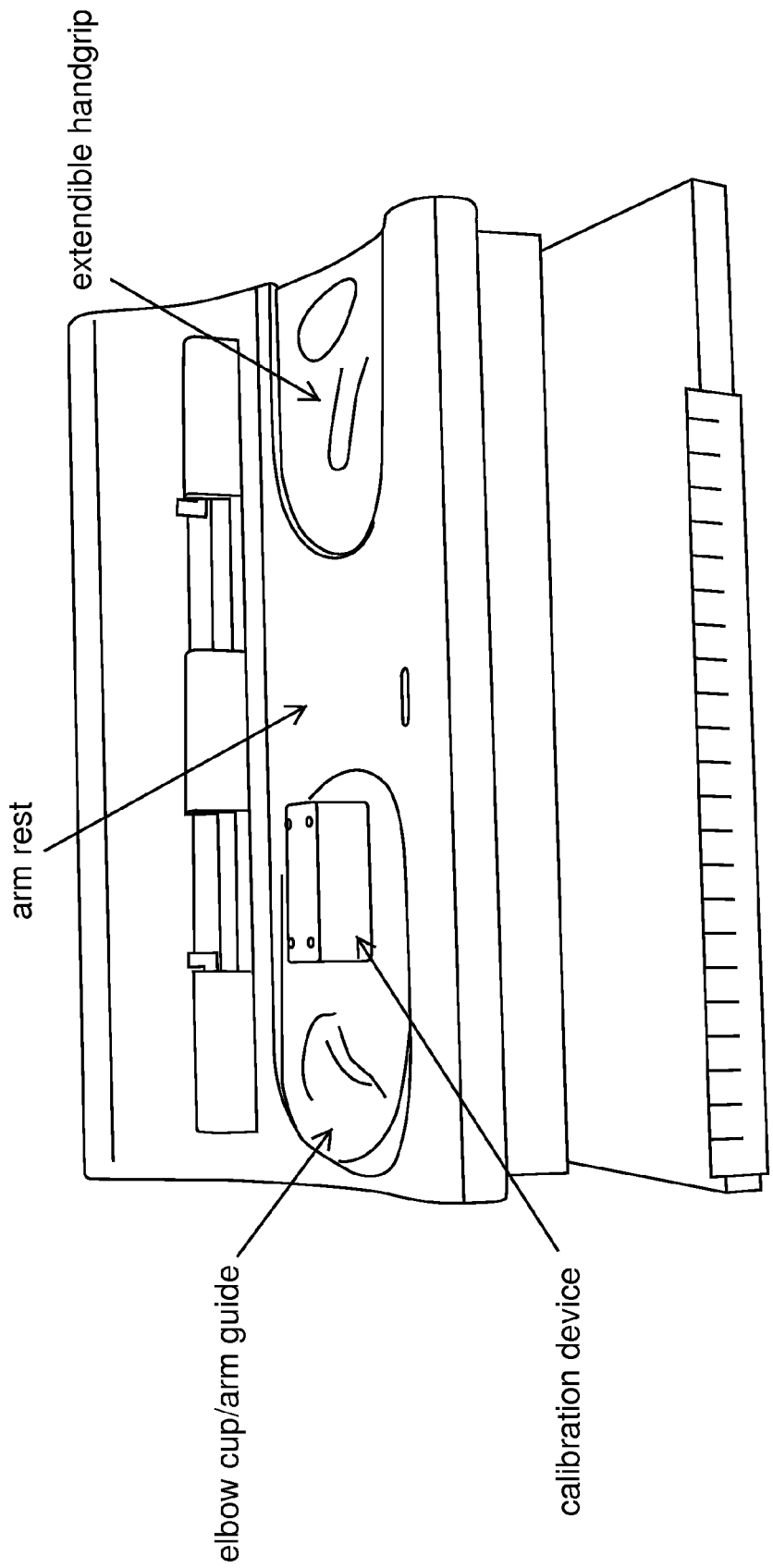
FIG. 9 is an illustration of a cradle and calibration device of an embodiment of the present invention.

The optical probe is a novel, two detection channel device that uses uniform spacing between the source and receiver fibers to reject surface/shallow depth reflections and target light that reflects or is emitted primarily from the dermal layer of the tissue. FIG. 7 is a schematic drawing of an example embodiment of an optical probe. The input ferrule of the probe holds fiber optics in a square pattern to match the shape of the square light guide in the light source. The light is conducted to the probe head where it illuminates the tissue of an individual. FIG. 8 shows arrangement of the source and detection channels at the probe head. The source fibers are separated from the detection fibers by a minimum of 80 microns (edge to edge) in order to reject light reflected from the tissue surface. Reflected and emitted light from the beneath the skin surface is collected by the detection channels and conducted to separate inputs of a spectrograph. The two detection channels have different but consistent spacing from the source fibers in order to interrogate different depths to the tissue and provide additional spectral information used to detect disease in or assess the health of an individual. The output ferrule of each detection channel arranges the individual fibers in to a long and narrow geometry to match the input slit height and width of the spectrograph. Other shapes are possible and will be driven by the imaging requirements of the spectrograph and the size of the CCD camera used for detection.

It is also possible to run the optical probe in reverse. What were the illumination fibers can become the detection fibers and the two channels of detection fibers become two channels of illumination fibers. This configuration requires two light sources or an optical configuration that can sequentially illuminate the two fiber bundles. It reduces the optical performance requirements of the spectrograph and allows use of a smaller area CCD camera. It also eliminates the need for a mechanical flip mirror in the spectrograph.

FIG. 14 shows an isometric view of an example embodiment of a trifurcated optical probe having two input illumination channels and one detection channel. The fibers making up each of the illumination channels are bundled together, in this case into a square packed geometry, and Snatch the geometric extent of the light guides of the light source subsystem. Channel 1 utilizes 81 illumination fibers; channel 2 uses 50 illumination fibers. The 50 fibers of the detection channel are bundled together in a 2×25 vertical array, and will form the entrance slit of the spectrograph. In the present examples 200/220/240 micron core/cladding/buffer silica-silica fibers with a 0.22 numerical aperture are used.

The illumination and detection fibers are assembled together at a common plane at the tissue interface. FIG. 15 depicts the relative spatial locations between illumination and detection fibers, where the average center-to-center fiber spacing, (a), from the channel 1 illumination fibers to detection fibers is 0.350 mm, and where the average center-to-center fiber spacing, (b), from the channel 2 illumination fibers to detection fibers is 0.500 mm. The overall extent of fiber pattern is roughly 4.7×4.7 mm. It should be noted that other geometries may be used, having greater or fewer illumination and/or detection fibers, and having a different spatial geometry at the tissue interface.

Figure 33:
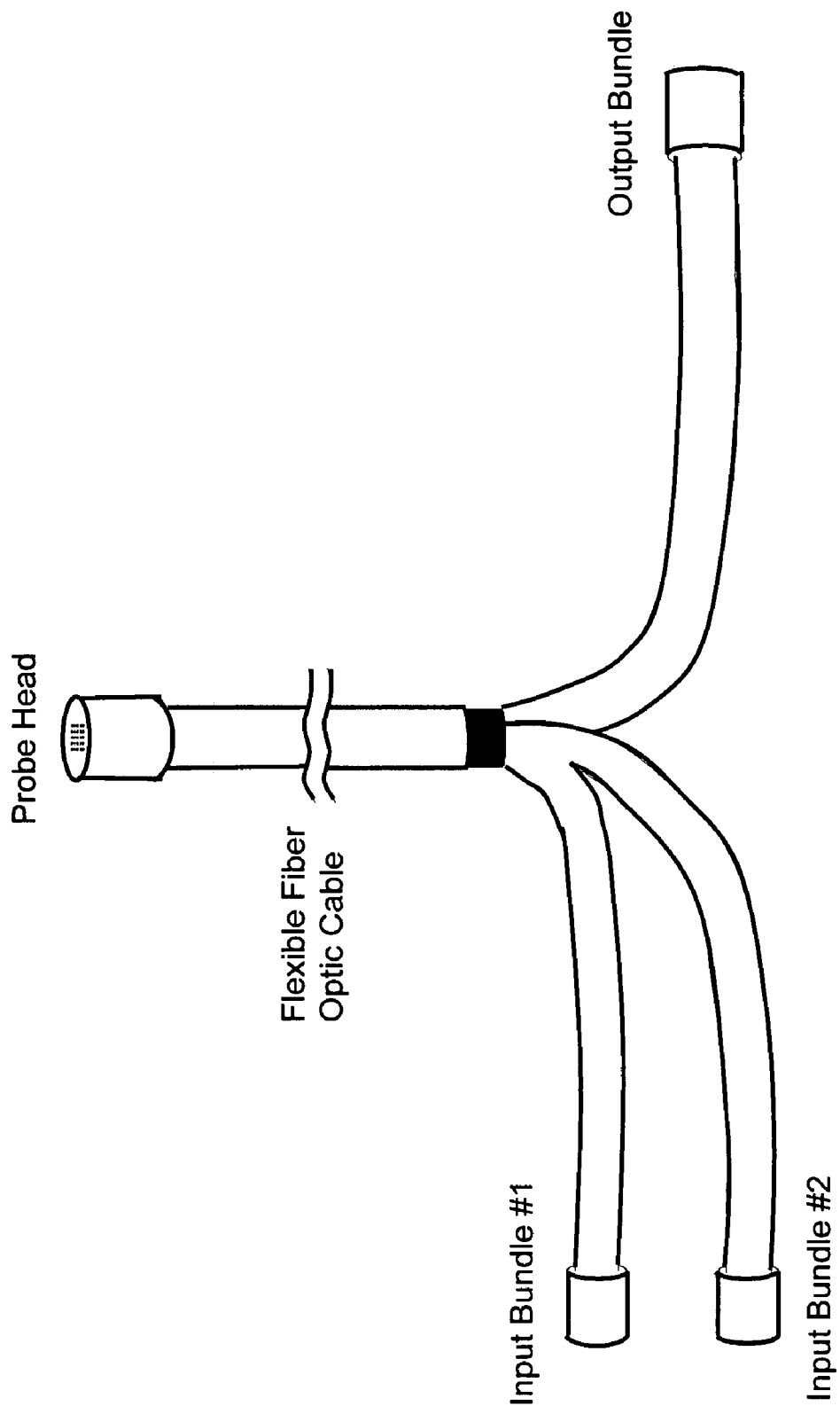
FIG. 33 is a schematic illustration of a tissue sampling system suitable for use in the present invention.
Figure 34:
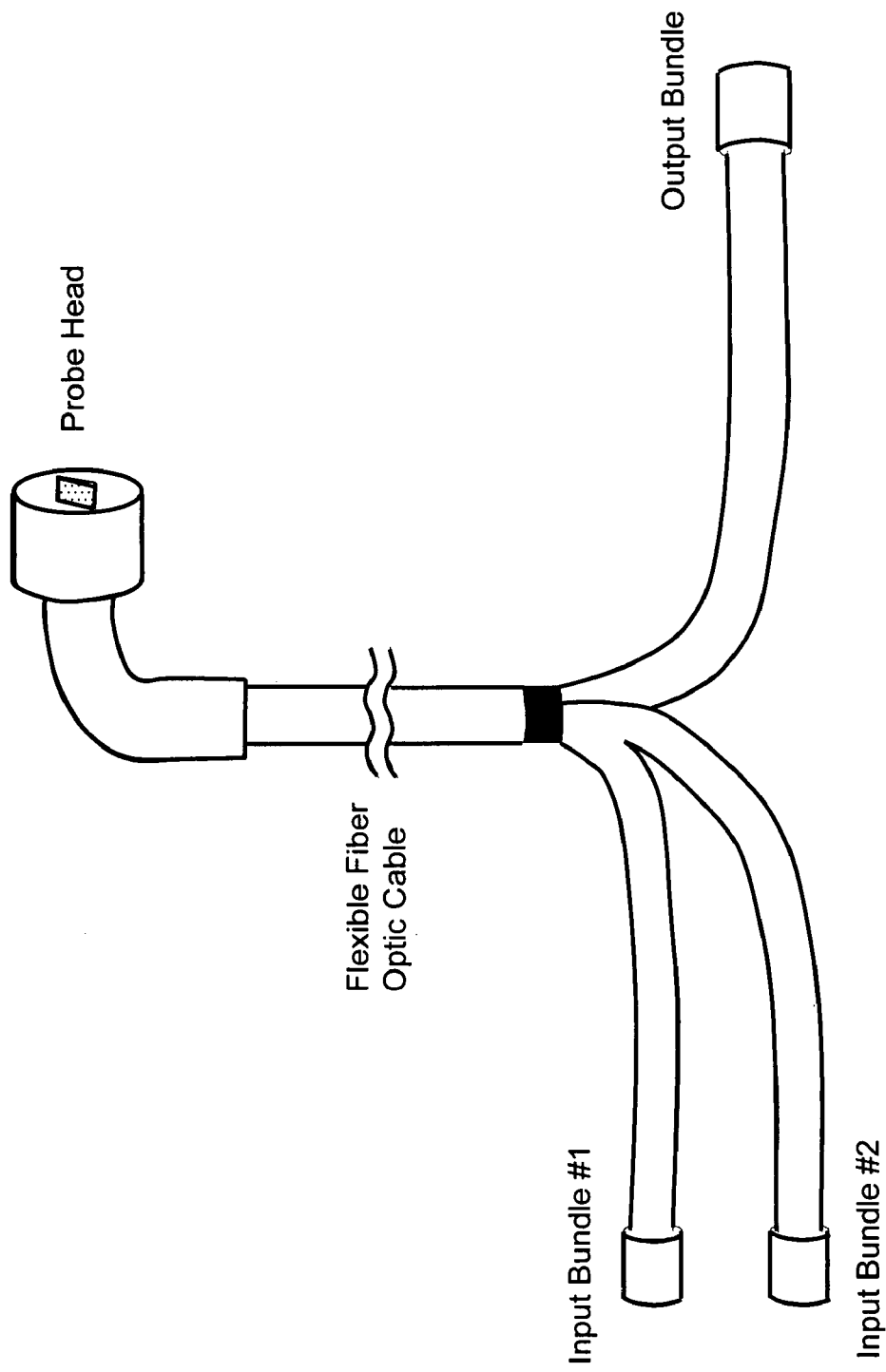
FIG. 34 is a schematic illustration of a tissue sampling system suitable for use in the present invention.

In addition to the fixed position optical probe disclosed above, some embodiments of the present invention include a flexible optical probe to measure the skin of the forearm, as well as skin located on other parts of the body (e.g. inside of upper arm, back, buttocks, hand, cheek, earlobe, forehead, neck, upper/lower leg, foot, etc.), the oral mucosa, and the sclera of the eye. The oral mucosa and sclera contain AGEs, collagen and elastin have adequate blood flow and no stratum corneum or hair, making them attractive measurement sites in addition for some embodiments of the present invention. The flexible probe can comprise a bundle of input and output fiber optic cables that are arranged in a pattern at the sample contact point designed to preferentially target the information bearing layers of the skin, oral mucosa or sclera. FIGS. 33 and 34 are schematic illustrations of example embodiments of a flexible probe with a notable difference being a straight versus angled probe head. The probe can vary in length from approximately 1 foot to 10 feet, with the practical limits defined more by probe cost (longer probes cost more) and human factors considerations. The optical probe geometry disclosed previously is an example of a suitable arrangement of input and output fibers at the probe head designed to target the dermal layer of the skin, reject surface and shallow depth lays that do not contain useful information, reduce probe contact variance and provide adequate overall signal-to-noise ratio for the measurement. The contact surface of the probe can be polished flat or curved to make the desired contact sampling sites with natural curvature, such as, for example, the sclera of the eye.

Movement of a flexible probe (e.g., a fiber optic probe) can cause artifacts in the measurement. As a specific example, bending of the fibers due to repositioning of the probe head can cause disturbances to the light propagating down the length of the fibers resulting in measured signal distortions. This can be especially true for large diameter, multimode fibers where light can follow multiple paths, or modes, as it travels down the fiber. When light is launched into a fiber, the modes are excited to varying degrees depending on the conditions of the launch, such as the distribution of input angles, the fill size and spatial distribution of the light on the fiber end, the spectral content of the light, and the like. The distribution of the light among the modes can change and evolve with distance as light is exchanged between them, and can be further influenced by movement of the fiber. As a result, these disturbances can manifest themselves as spectral, spatial, and/or angular distortions to the original content of light launched into the fiber, and can consequently impart an effect on the detected signal. In the present invention, a change to the detected signal can result in a change to a recorded spectrum, and can complicate the ensuing analysis.

Conditioning of the light can aid in mitigating the effect of these disturbances on the detected signal, thereby reducing the sensitivity of a fiber optic probe to movement. The conditioning of the light can be performed prior to launch into the fiber, upon exiting the fiber, or both, and can be additionally performed prior to interrogation of a sample, after interrogation of a sample, or both. In addition, conditioning can be performed to the light while it travels down the length of the fiber. Here the term "fiber" can refer to a single fiber optic or a plurality of fibers constituting a bundle and/or a fiber optic probe assembly.

Since the response of the detected signal to movement of the fiber bundle can be dependent upon the launch conditions of the light and the distribution and change of distribution of light among the various modes of the fiber, treatment of the light prior to entering the fiber can help to reduce its sensitivity to such effects. This can be achieved through homogenization, or creating uniformity to the spectral, spatial, and/or angular content of the light. Various methods to condition (homogenize) the light are possible and may include the use of integrating spheres or chambers, light pipes, diffusers, and mode scramblers.

Figure 35:
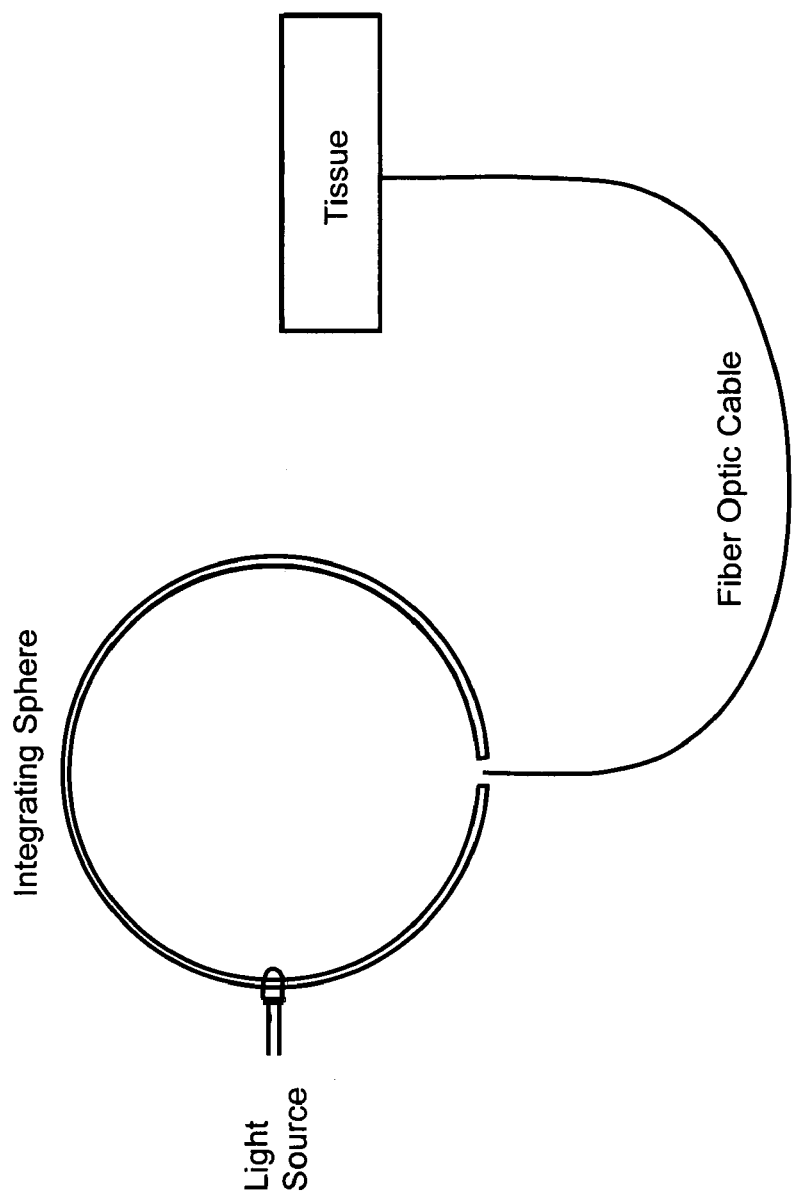
FIG. 35 is a schematic illustration of an illumination system suitable for use in the present invention.
Figure 36:
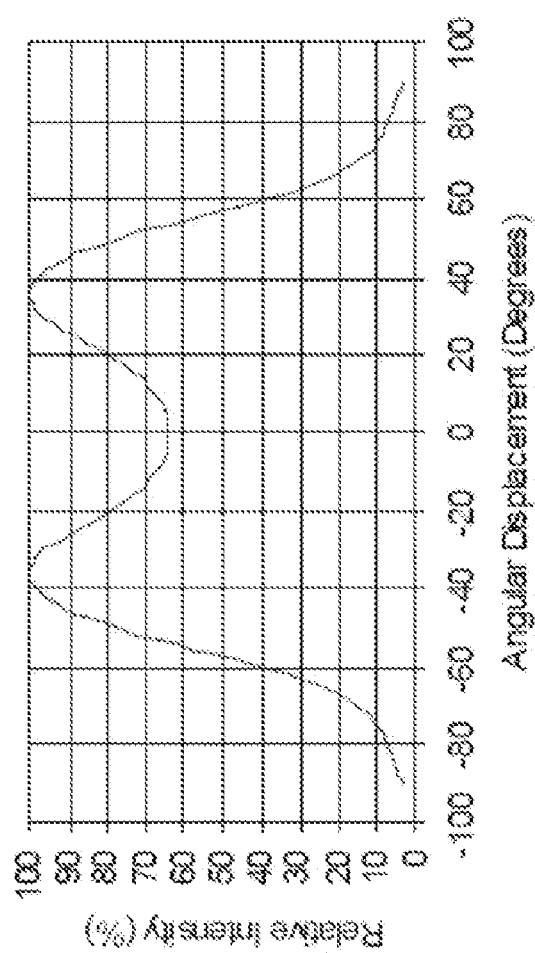
FIG. 36 is a graph of relative intensity and angular displacement of light obtained from an LED.

FIG. 35 shows an example of an integrating sphere used to homogenize the spectral, spatial, and angular properties of light to be launched into a fiber. The design and properties of integrating spheres are well known to those skilled in the art. Light is received from a source, for example a light emitting diode (LED), and is collected by the integrating sphere. LED's are known to have non-uniform angular distributions of radiation emitted from their package, an example of which is commonly referred to as a 'batwing' profile seen in FIG. 36; the integrating sphere works to destroy this structure to bring about a more uniform distribution. The light undergoes multiple bounces and eventually strikes the surface of the fiber input end. At this point the angular, spatial, and spectral properties of the light have been sufficiency mixed, or homogenized, before launching into the fiber and coupled to a sample of interest (i.e. tissue).

Figure 37:
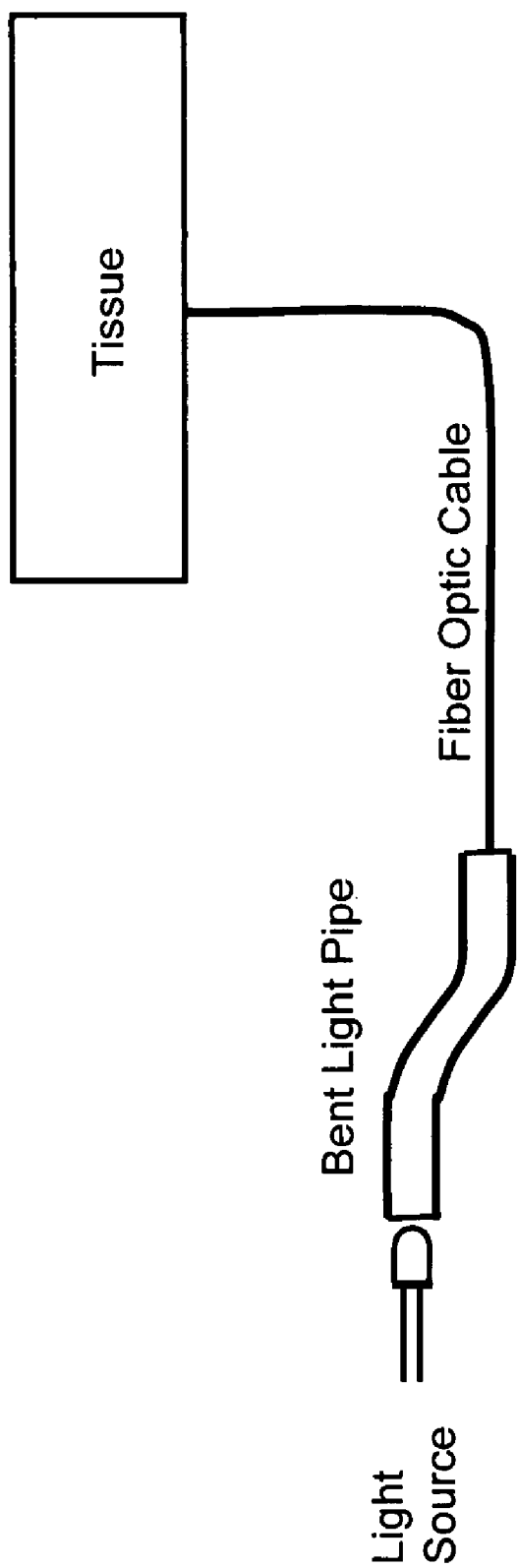
FIG. 37 is a schematic illustration of a light homogenizer in use with the present invention.

FIG. 37 shows an example of a light pipe used to homogenize the spectral, spatial, and angular properties of light. Additional discussion of such structures can be found in U.S. Pat. No. 6,684,099, incorporated herein by reference Properties that make light pipes useful in homogenizing light include cross-sectional geometry, shape, and texture of the walls. In the example shown in FIG. 37, light enters at the input end of a bent light pipe and propagates down its length, undergoing multiple bounces along the way. These bounces provide a degree of mixing of the light, and the design of the light pipe is set to achieve the desired amount of homogeneity of the light upon exiting at the output end. The fiber is brought coincident with the output end of the light pipe, either via butt-coupling or imaging, and the now homogenized light is launched into the fiber. The light pipe can have a polygonal cross section to further encourage homogenization in some embodiments.

Figure 38:
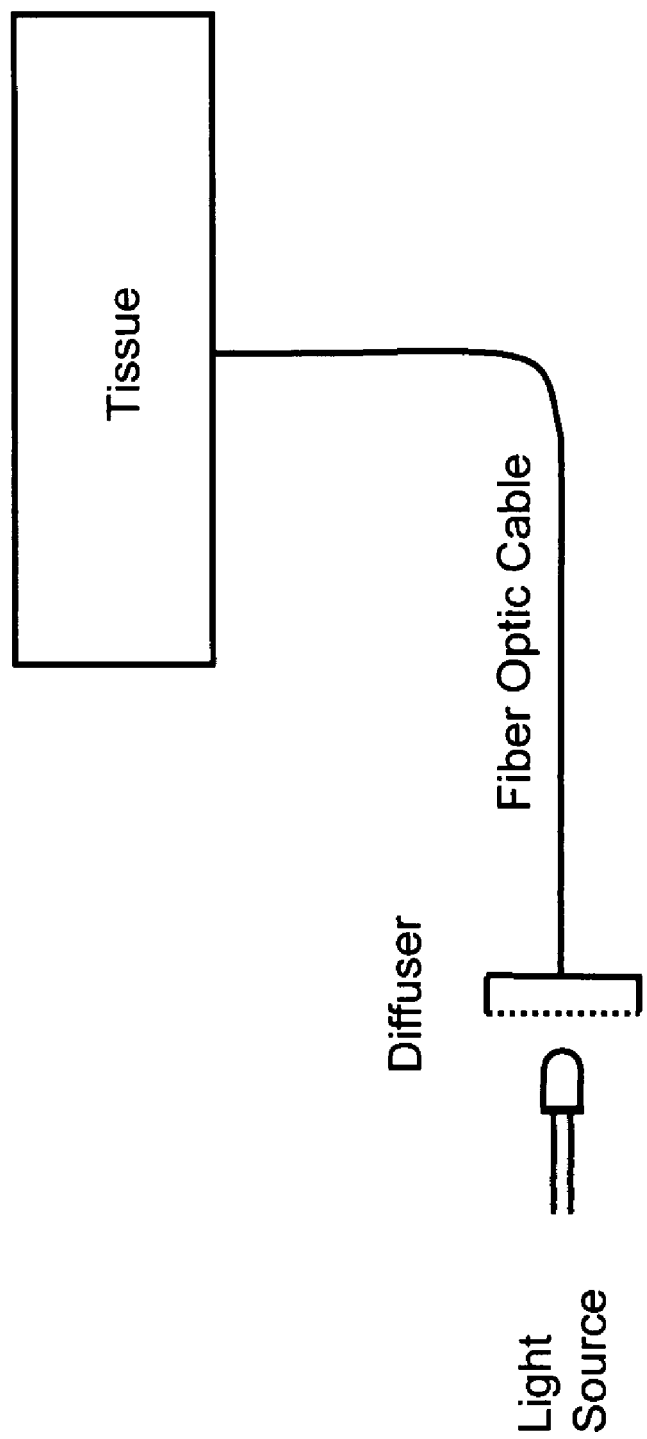
FIG. 38 is a schematic illustration of a light diffuser in use with the present invention.

Diffusers can take on many forms, for example ground glass diffusers, such as that fabricated by roughening one, or both, side(s) of a plane parallel plate of glass, opal glass diffusers, or holographically produced surface topologies on the surface of a suitable substrate. Other forms of suitable diffusers may exist, and this list is not to be considered exhaustive. FIG. 38 shows an example of a ground glass diffuser used to homogenize the spectral, spatial, and angular properties of light. Light from a source strikes a first roughened surface of the diffuser and is scattered or refracted. This scattering destroys the original spatial and angular properties of the light, bringing about a more uniform distribution to then be coupled and launched into a fiber.

While the aforementioned embodiments of light homogenizers can be used to condition the light prior to interrogation of a sample, it can also prove beneficial to incorporate similar means to homogenize the light collected from the sample before it is detected (e.g., prior to the input of a spectrometer). In this manner, the light collected from the sample is first launched into the desired light homogenizer, such as an integrating sphere, light pipe, or diffuser, for conditioning before it is launched into the fiber connected to the detection device. Alternately, the output fibers can collect the diffusely reflected and emitted light from the tissue (skin, oral mucosa or sclera) and transmit that light to the input of light homogenizers. The output of the light homogenizer is then transmitted to the spectrograph via butt coupling, imaging optics or other appropriate optical conveyances from measurement.

Figure 39:
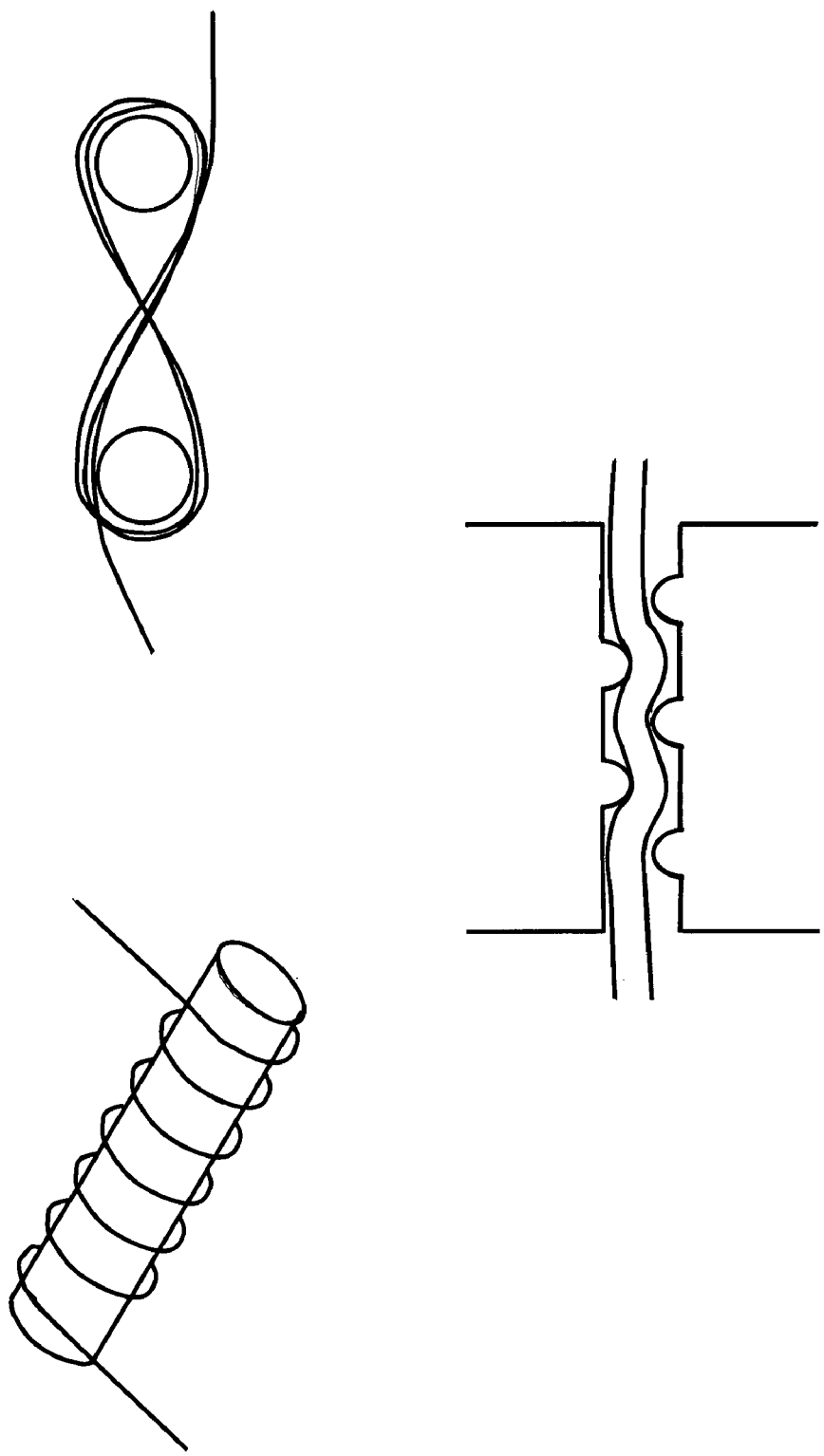
FIG. 39 is a schematic illustration of several mode scramblers suitable for use with the present invention.
Figure 40:
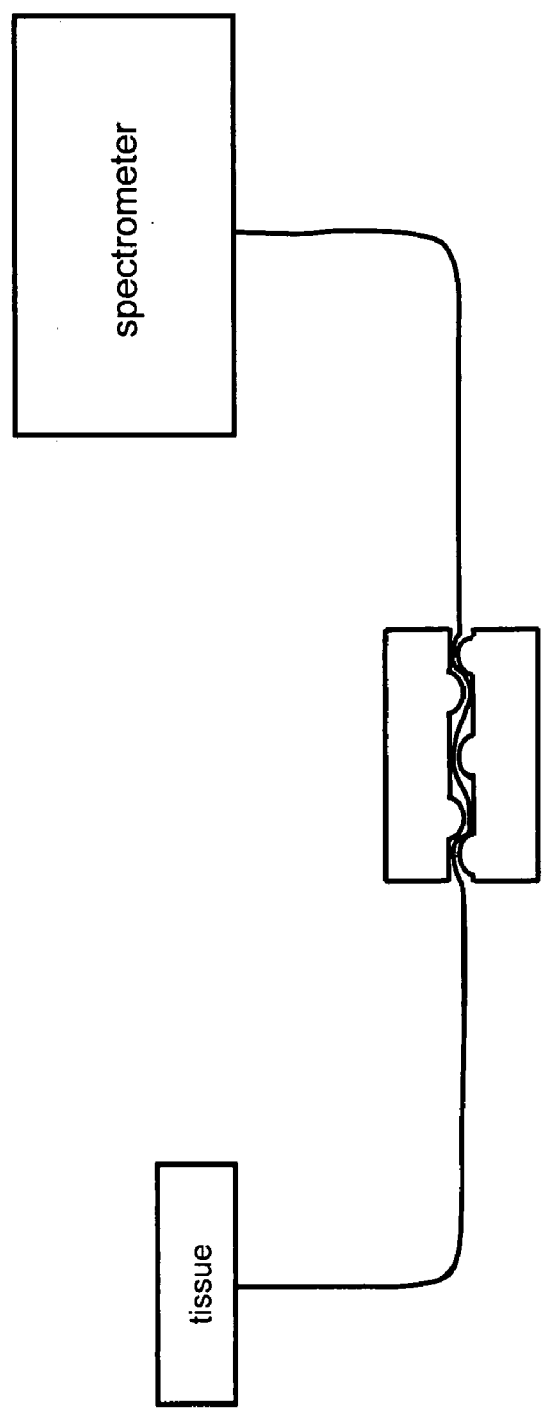
FIG. 40 is a schematic illustration of a mode scrambler in use with the present invention.

Another method to reduce sensitivity of the detected signal to movement of the fiber optic probe is through the use of what are commonly known as mode scramblers. Examples of mode scramblers include wrapping fibers around a drum or mandrel. FIG. 8 windings, and creation of microbends such as those resulting from sandwiching the fiber between corrugated plates, among others. Examples of mode scramblers are depicted in FIG. 39. Mode scramblers encourage a stable mode distribution by redistributing the light into all of the available modes. In doing so, the distribution of light among the modes is substantially independent of launch conditions. In addition, it is this uniformity in modal distribution of light that reduces the detected signal's sensitivity to movement of the fiber optic probe as any losses of light incurred through bending of the fiber are now more uniform across the spectral, spatial, and angular properties of the light. FIG. 40 depicts the implementation of a mode scrambler for use with a fiber optic probe. Light from a sample is collected by an optical fiber or fibers to be sent to a spectrometer. Between the sample and spectrometer a mode scrambler is placed to impart a higher degree of uniformity to the spectral, spatial, and angular properties of the light propagating down the fiber.

Figure 42:
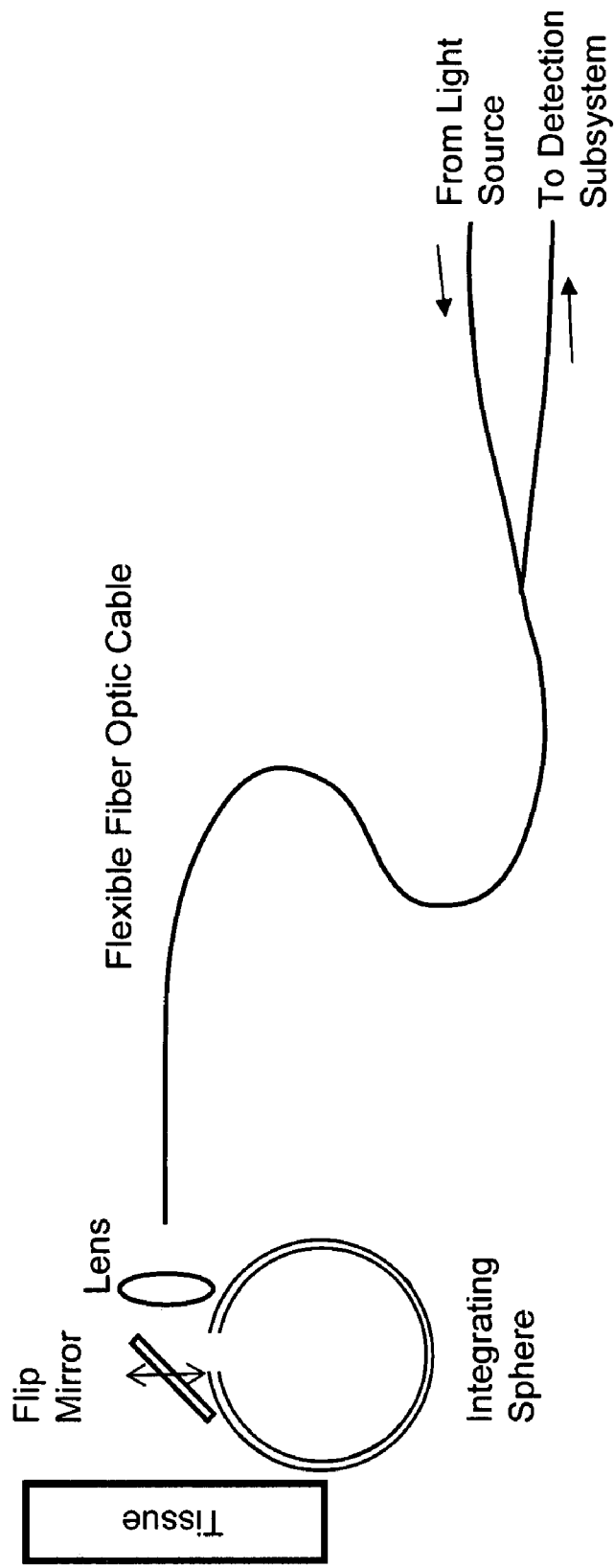
FIG. 42 is a schematic illustration of an example embodiment of the present invention.

Another method to counteract spectral distortions induced by movement or fixture of a fiber-optic bundle is to measure the alterations to the spectra and compensate for them mathematically (e.g., ratio, subtraction, transformation, etc.). An example of this technique is illustrated schematically in FIG. 42. In this instance, a non-contact probe is depicted but variations of the technique can be employed with probes in which the fibers are in direct contact with the tissue surface. The example probe in the figure includes an integrating sphere and a movable mirror. Other embodiments can include other reflectance and deflection devices that allow occasional or continuous sampling of light transmitted to the tissue via a flexible probe (e.g., via a bundle of optical fibers). In conjunction with measurements of tissue optical phenomena (e.g., elastic scattering such as reflectance or inelastic processes such as fluorescence, Raman scattering or Brillouin scattering), the light exiting the probe can be deflected into the integrating sphere. Diversion of the probe optical output into the integrating sphere can occur periodically, interspersed with the illumination of the tissue, or by continuously sampling a fraction of the light emanating from the bundle. The detection fibers of the bundle collect the light returned by the integrating sphere and couple the light to the detection subsystem. The measured spectrum represents the round-trip spectral lineshape of the bundle. That spectrum can be compared to the nominal lineshape of the bundle to mathematically compensate or remove any spectral distortion induced by the position, orientation or flexure of the bundle and probe during a particular tissue measurement.

Figure 41:
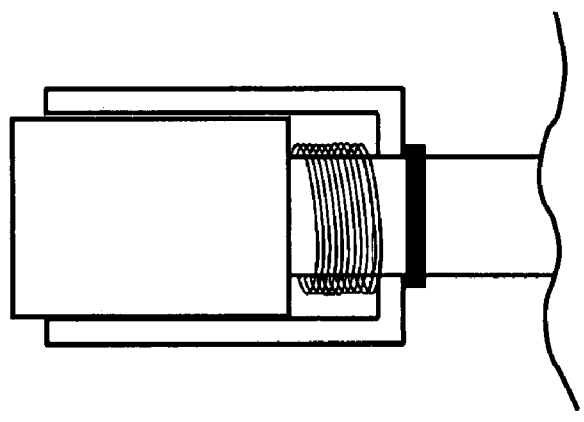
FIG. 41 is a schematic illustration of a spring-loaded probe head suitable for use with the present invention.

An embodiment of the flexible optical probe can incorporate one or more mechanisms to ensure proper contact between the surface of the optical probe and the target tissue. The contact mechanisms are not required but can provide an advantage in measurement accuracy and/or reliability in some applications. Example mechanisms include a spring loaded optical probe head that can be depressed to a certain degree before acceptable contact is established with the skin. FIG. 41 illustrates such a mechanism. Switches such as mechanical, optical and/or magnetic switches, can be incorporated into the probe head to indicate that proper contact has been established with the tissue. In addition, the tissue contact quality can be assessed by measuring the spectrum of light returned from the optical probe and comparing the measured spectrum to known good spectra using various metrics like spectral F ratio, Mahalanobis distance, peak ratios, signal-to-noise ratio, relative shape, relative amplitude or other similarity and/or difference metrics.

In addition to contact sampling with a rigid or flexible optical probe, some embodiments of the present invention measure the skin, oral mucosa or sclera with a non-contact approach based on polarized light and imaging optics, such as the system described in U.S. application Ser. No. 11/350,916, filed Feb. 9, 2006, incorporated by reference. A non-contact embodiment can provide for elimination of tissue contact issues, patient comfort when measuring the sclera, reduced risk of cross-contamination between uses, control over optical penetration into the tissue and the ability to optically sample a large area of the tissue to mitigate the effects of tissue heterogeneity.

Figure 43:
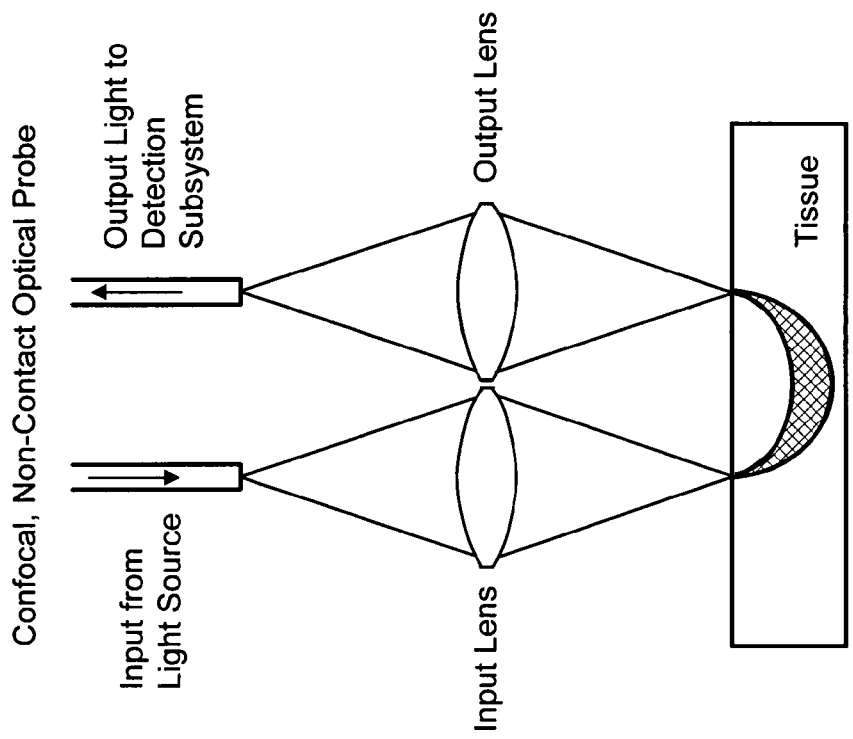
FIG. 43 is a schematic illustration of a tissue sampling system suitable for use in the present invention.

Another embodiment of a non-contact probe is illustrated in FIG. 43. The example probe can preserve the spatial and depth selectivity of in-contact fiber probes but avoid the tissue interface and coupling issues. In the example embodiment concept the light is coupled between the probe and tissue surface in a confocal configuration. The fibers define the confocal apertures that are relayed to the tissue surface by lenses. This design launches light into the same spatial location as with a contacting fiber and with similar angular and intensity distribution. The banana-shaped region depicted underneath the tissue surface represents the distribution of tissue volume that photons transit between the entry and exit points defined by the inter-fiber separation. The detection-side relay lens couples light exiting the tissue to the detection fiber. The geometry of the lens and fiber dictate the numerical aperture of the detector portion of the probe. This embodiment rejects light that exits tissue outside the designed spatial and angular acceptance criteria.

The calibration device provides a reflectance standard (diffuse or otherwise) that is periodically placed on the optical probe to allow measurement of the overall instrument line shape. The measurement of the instrument line shape is important for calibration maintenance and can be used to compensate for changes/drifts in the instrument line shape due to environmental changes (e.g. temperature, pressure, humidity), component aging (e.g. LEDs, optical probe surface, CCD responsivity, etc.) or changes in optical alignment of the system. Calibration device measurements can also be used to detect if the instrument line shape has been distorted to the point that tissue measurements made with the system would be inaccurate. Examples of appropriate calibration devices include a mirror, a spectralon puck, a hollow integrating sphere made of spectralon, a hollow integrating sphere made of roughened aluminum or an integrating sphere made of solid glass (coated or uncoated). Other geometries besides spherical are also effective for providing an integrated reflectance signal to the detection channel(s) of the optical probe. The common characteristic of all these calibration device examples is that they provide a reflectance signal that is within an order of magnitude of the tissue reflectance signal for a given LED and optical probe channel and that reflectance signal is sensed by the detection portions of the optical probe.

The calibration device can be used to measure the instrument line shape for each LED and the neon lamp of the illumination subsystem for each input channel of the optical probe. The measured neon lamp line shape is especially useful for detecting and correcting for alignment changes that have shifted or otherwise distorted the x-axis calibration of the instrument because the wavelengths of the emission lines of the neon gas are well known and do not vary significantly with temperature. The measurement of each LED for each optical probe channel can be used to determine if the instrument line shape is within the limits of distortion permitted for accurate tissue measurements and, optionally, can be used to remove this line shape distortion from the measured tissue spectra to maintain calibration accuracy. Line shape removal can be accomplished by simple subtraction or ratios, with optional normalization for exposure time and dark noise.

The spectrograph disperses the light from the detection channels into a range of wavelengths. In the example of FIG. 1, the spectrograph has a front and side input that utilizes a flipper mirror and shutter to select which input to use. The input selection and shutter control is done by computer. The spectrograph uses a grating (i.e. a concave, holographic grating or a traditional flat grating) with blaze and number of grooves per inch optimized for the spectral resolution and spectral region needed for the noninvasive detection of disease. In the current example, a resolution of 5 nm is sufficient, though higher resolutions work just fine and resolution as coarse as 2520 nm will also work. The dispersed light is imaged onto a camera (CCD or otherwise) for measurement.

FIG. 16 depicts an example embodiment of the spectrograph. It is composed of a single concave diffraction grating having two conjugate planes defining entrance slit and image locations. The concave diffraction grating collects light from the entrance slit, disperses it into its spectral components, and reimages the dispersed spectrum at an image plane. The grating can be produced via interferometric (often call holographic) or ruled means, and be of classical or aberration corrected varieties.

The detection fibers of the optical probe are bundled into a 2×25 array and can define the geometry of the entrance slit. The fiber array is positioned such that the width of the slit defined by the 2 detection fibers in the array lies in the tangential plane (in the plane of the page), and the height of the slit defined by the 25 fibers of the array lie in the sagittal plane (out of the plane of the page).

In addition to allowing the array of detection fibers to define the entrance slit, an auxiliary aperture, such as two knife edges or an opaque member with appropriate sized opening, can be used. In this configuration, the fiber array would be brought into close proximity with the aperture so as to allow efficient transmission of light through the aperture. The size of the aperture can be set to define the spectrometer resolution.

The detection fiber array can also be coupled to the entrance slit of the spectrometer with a light guide. An appropriately sized light guide matching the geometric extend of the 2×25 detection fiber array, e.g. 0.5×6 mm, and having a length of at least 20 mm can be used, having an input side coupled to the fiber array and an output side that can either define the entrance slit of the spectrometer or coupled to an aperture as described previously. The light guide can take the form of a solid structure, such as a fused silica plate, or of a hollow structure with reflective walls. The light guide can be particularly useful when considering calibration transfer from one instrument to another because it reduces the tolerance and alignment requirements on the detection fiber array by providing a uniform input to the spectrograph slit.

In the current example the diffraction grating is capable of dispersing light from 360 to 660 nm over a linear distance of 6.9 mm, matching the dimension of a CCD image sensor. FIG. 17 shows an example of an image formed onto the CCD image sensor with multiple wavelengths of 360, 435, 510, 585, and 660 nm, and the corresponding spectrum produced by vertically binning the pixels of the CCD shown below. Gratings with other groove densities can be used depending on the desired spectral range and size of the image sensor.

Figure 18:
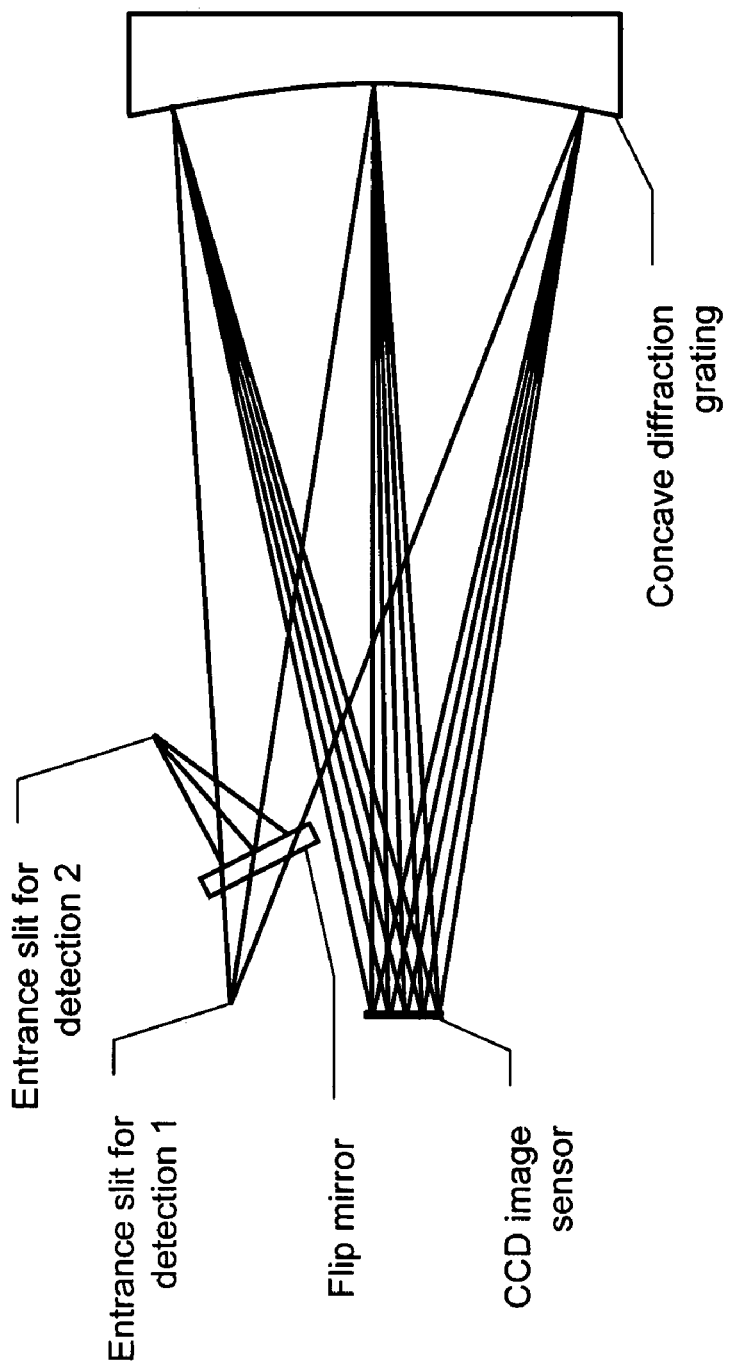
FIG. 18 is a schematic depiction of an example spectrograph suitable for use in the present invention.

A previously disclosed optical probe described having two detection channels. While the aforementioned spectrometer identifies a single entrance slit to interface with a single detection channel of an optical probe, it is possible to design the spectrometer to accept multiple inputs. FIG. 18 depicts another embodiment in which a flip mirror is used to change between one of two entrance slits. The location of each entrance slit is chosen so that they have a common conjugate at the image plane. In this manner, one can chose between either of the two inputs to form a spectral image of the corresponding detection channel.

Figure 19:
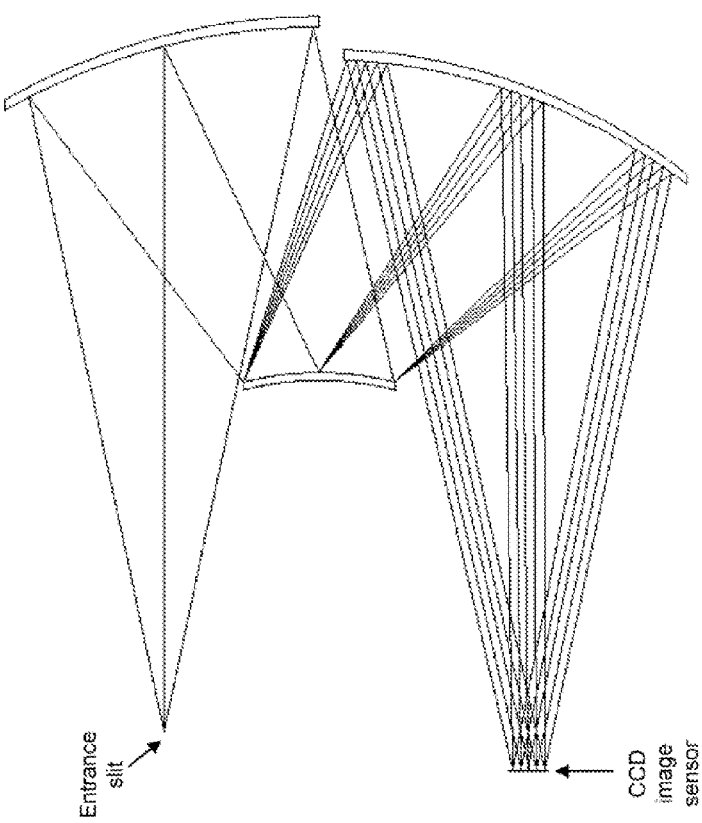
FIG. 19 is a schematic depiction of an example spectrograph suitable for use in the present invention.

One skilled in the art will realize that other mounts, gratings, and layout designs may be used with similar intent. FIG. 19 shows just one example, that of an Offner spectrograph having primary and tertiary concave mirrors, and a secondary convex diffraction grating. The Offner spectrometer is known to produce extremely good image quality as there are sufficient variables in the design to correct for image aberrations, and therefore has the potential of achieving high spectral and spatial resolution. Other examples of suitable spectrograph designs may include, but are not necessarily limited to, Czerny-Turner, Littrow, transmission gratings, and dispersive prisms.

The CCD camera subsystem measures the dispersed light from the spectrograph. All wavelengths in the spectral region of interest are measured simultaneously. This provides a multiplex advantage relative to instruments that measure one wavelength at a time and eliminates the need to scan/move the grating or detector. The exposure time of the camera can be varied to account for the intensity of the light being measured. A mechanical and/or electrical shutter can be used to control the exposure time. The computer subsystem instructs the camera as to how long an exposure should be (10's of milliseconds to 10's of seconds) and stores the resulting image for later processing. The camera subsystem can collect multiple images per sample to allow signal averaging, detection of movement or compensation for movement/bad scans. The CCD camera should have good quantum efficiency in the spectral region of interest. In the current example, the CCD camera is responsive to light in the 250 to 1100 nm spectral range.

The computer subsystem controls the operation of the light source, spectrograph and CCD camera. It also collects, stores and processes the images from the camera subsystem to produce an indication of an individual's disease status based on the fluorescence and reflectance spectroscopic measurements performed on the individual using the instrument. As shown in FIG. 20, an LCD display and keyboard and mouse can serve as the operator interface. There can be additional indicators on the instrument to guide the patient during a measurement. In addition, audio output can be used to improve the usability of the instrument for patient and operator.

Compensation for Competitive Signal

Figure 28:
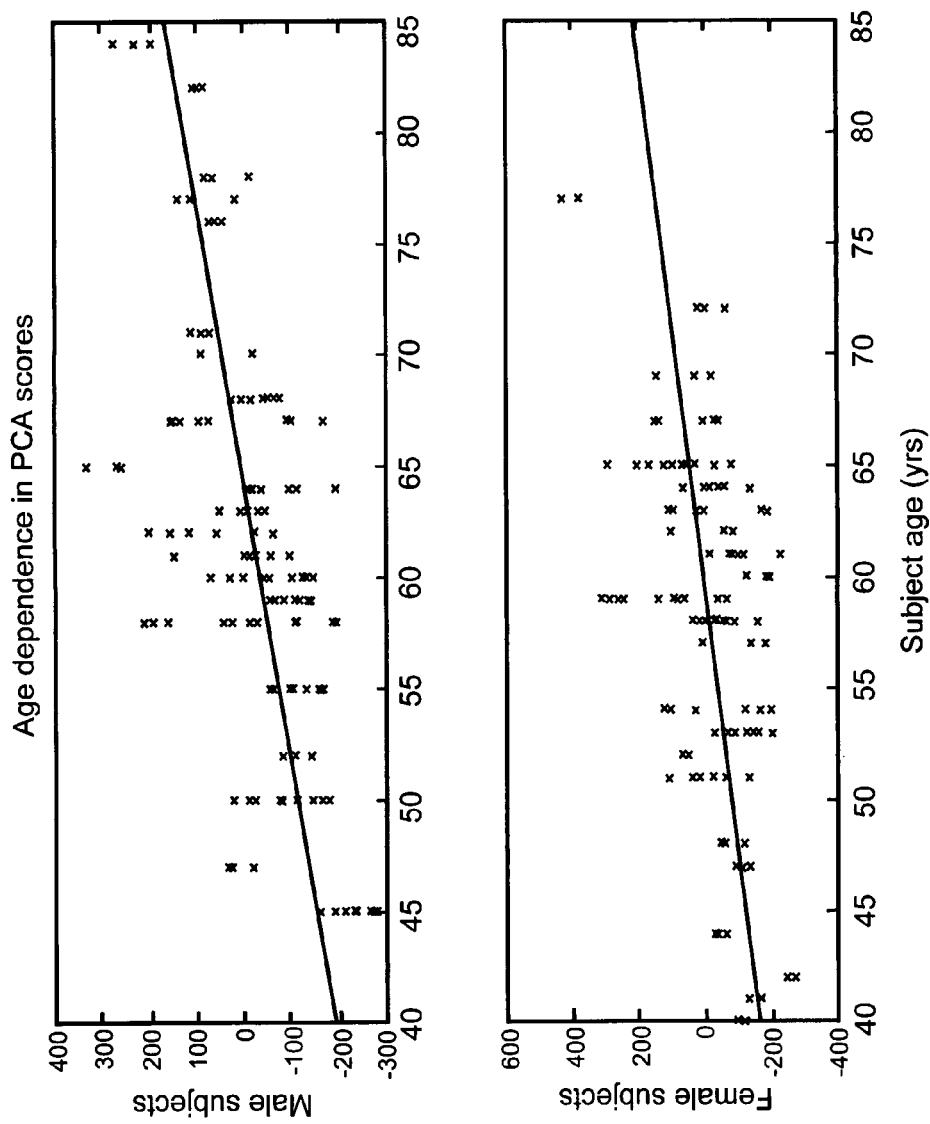
FIG. 28 is an illustration of the age dependence of skin fluorescence.

This method refers to techniques for removing or mitigating the impact of predictable signal sources that are unrelated to and/or confound measurement of the signal of interest. As compared to multivariate techniques that attempt to "model through" signal variances this approach characterizes signal behavior that varies with a quantifiable subject parameter and then removes that artifact. One example of such a signal artifact is the age-dependent variation of skin fluorescence. Because of signal overlap between skin fluorescence due to age and similar fluorescence signals related to disease state, uncompensated signals can confuse older subjects without disease with younger subjects with early stage disease (or vice versa). FIG. 28 illustrates the dependence of skin fluorescence with the age of an individual.

Similar competitive effects may be related to other subject parameters (e.g., skin color, skin conditions subject weight or body-mass-index, etc.). Numerous techniques exist for modeling and compensation. Typically, a mathematical algorithm is established between signal and the parameter based upon measurements in a controlled set of subjects without disease or health condition. The algorithm can then be applied to new subjects to remove the signal components relating to the parameter. One example relates to compensation for age-dependent skin fluorescence prior to discriminant analysis to detect disease or assess health. In this approach the spectra from subjects without disease are reduced to eigen-vectors and scores through techniques such as singular-value decomposition. Polynomial fits between scores and subject ages are computed. Scores of subsequent test subject spectra are adjusted by these polynomial fits to remove the non-disease signal component and thus enhance classification and disease detection performance.

Combining Classification Techniques

The technique described here improves classification performance by combining classifications based upon different disease thresholds and/or applying a range of classification values rather than simply binary (one or zero) choices. Typical disease state classification models are built by establishing multivariate relationships in a calibration data set between spectra or other signals and a class value. For example, a calibration subject with the disease or condition can be assigned a class value of one while a control subject has a class value of zero. An example of the combined classification methods is to create multiple class vectors based upon different disease stages. Separate discriminant models can then be constructed from the data set and each vector. The resulting multiple probability vectors (one from each separate model) can then be bundled or input to secondary classification models to yield a single disease probability value for each sample. Bundling refers to a technique of combining risk or probability values from multiple sources or models for a single sample. For instance, individual probability values for a sample can be weighted and summed to create a single probability value. An alternative approach to enhance classification performance is to create a multi-value classification vector where class values correspond to disease stages rather than the binary value (one/zero). Discriminant algorithms can be calibrated to compute probability into each nom-control class for optimal screening or diagnostic performance.

Sub-modeling

Sub-modeling is a technique for enhancing classification or quantification model performance. Many data sets contain high signal variance that can be related to specific non-disease sample parameters. For example, optical spectra of human subjects can encompass significant signal amplitude variations and even spectral shape variations due primarily to skin color and morphology. Subdividing the signal space into subspaces defined by subject parameters can enhance disease classification performance. This performance improvement comes since subspace models do not have to contend with the full range of spectral variance in the entire data set.

One approach to sub-modeling is to identify factors that primarily impact signal amplitude and then develop algorithms or multivariate models that sort new, test signals into two or more signal range categories. Further grouping can be performed to gain finer sub-groupings of the data. One example of amplitude sub-modeling is for skin fluorescence where signal amplitude and optical pathlength in the skin is impacted by skin melanin content. Disease classification performance can be enhanced if spectral disease models do not have to contend with the full signal dynamic range. Instead, more accurate models can be calibrated to work specifically on subjects with a particular range of skin color. One technique for skin color categorization is to perform singular-value decomposition (SVD) of the reflectance spectra. Early SVD factors are typically highly correlated to signal amplitude and subject skin color. Thus, soiling scores from early SVD factors can be an effective method for spectrally categorizing spectra into signal amplitude sub-spaces. Test spectra are then categorized by the scores and classified by the corresponding sub-model.

Figure 29:
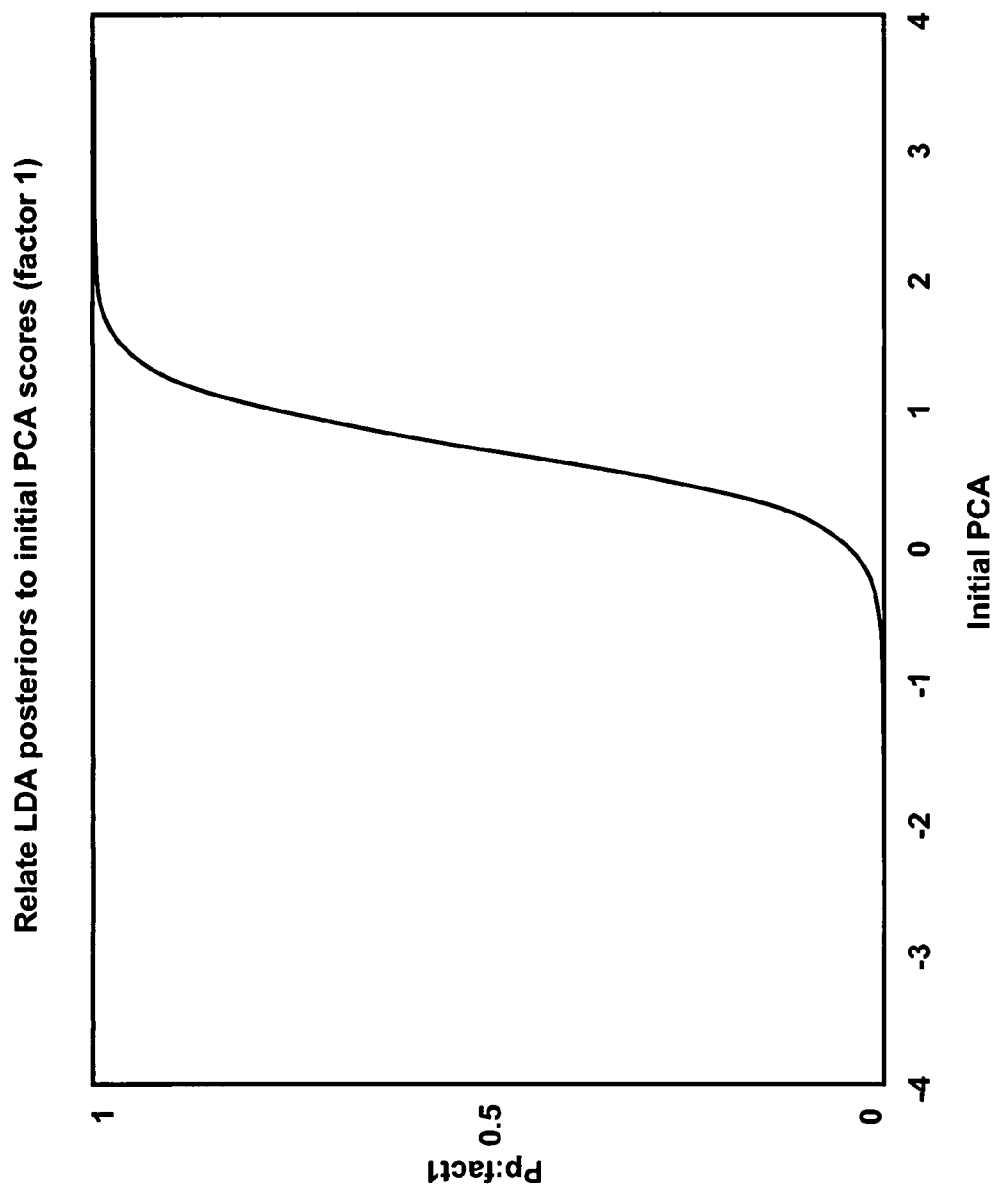
FIG. 29 is an illustration of skin color monitoring.

Another sub-modeling method groups spectra by shape differences that correspond to skin color or skin morphology. FIG. 29 illustrates one method of classifying an individual's skin color to help determine which sub-model to employ. Various techniques exist to spectrally subdivide and then sub-model. Clusters analysis of SVD scores can identify natural groups in the calibration set that are not necessarily related to subject parameters. The cluster model then categorizes subsequent test spectra.

Figure 30:
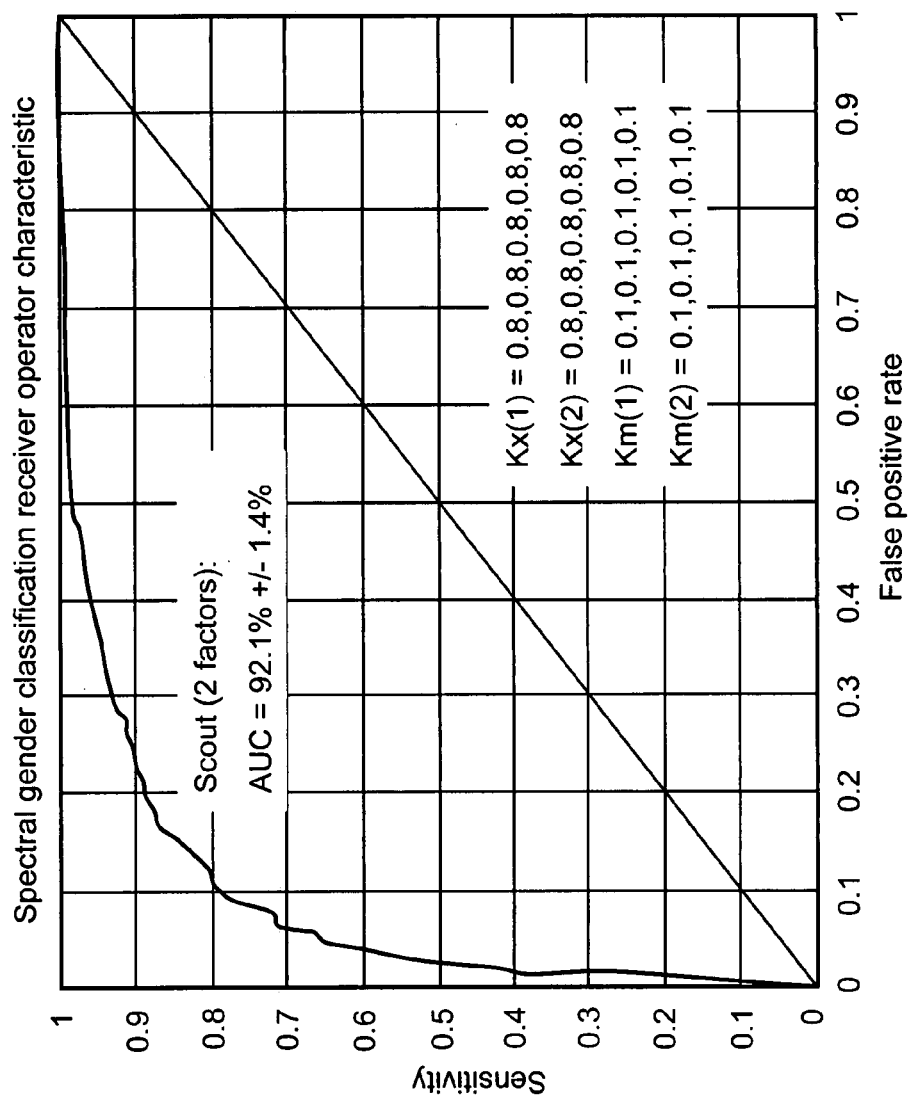
FIG. 30 is an illustration of a receiver operator characteristic relating to optical separation of genders.

Alternatively, spectral variance can form clusters relating subject parameters such as gender, smoking status, ethnicity, skin condition or other factors like body-mass-index. FIG. 30 shows a receiver operator characteristic of how well genders can be optically separated, with an equal error rate at 85% sensitivity and an area under the curve of 92%. In these instances, multivariate models are calibrated on the subject parameter and subsequent test spectra are spectrally sub-grouped by a skin parameters model and then disease classified by the appropriate disease classification sub-model.

In addition to spectral sub-grouping, categorization prior to sub-modeling can be accomplished by input from the instrument operator or by information provided by the test subject. For example, the operator could qualitatively assess a subject's skin color and manually input this information. Similarly, the subject's gender could be provided by operator input for sub-modeling purposes.

Figure 10:
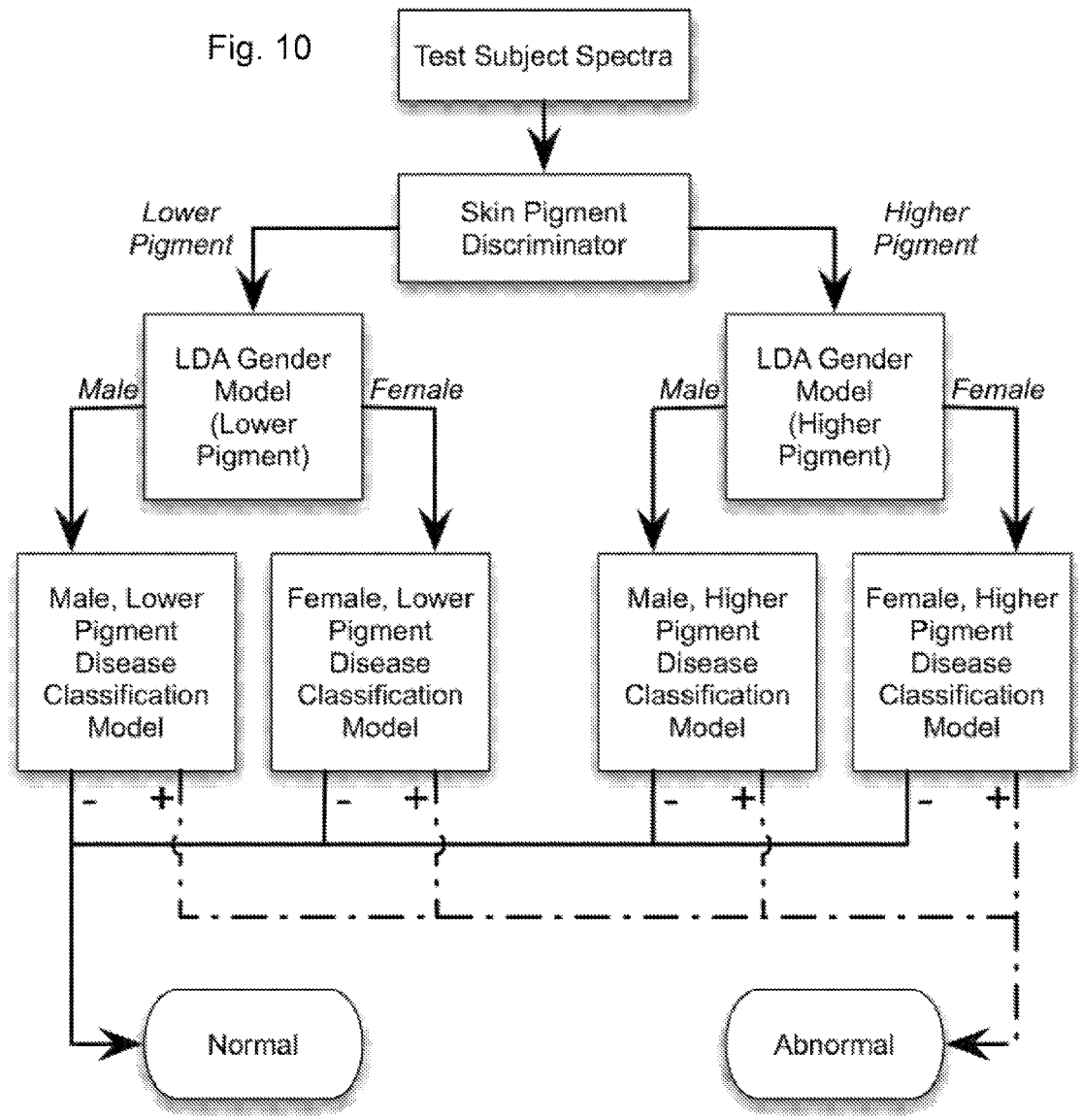
FIG. 10 is a flow diagram of a method of determining disease classification according to the present invention.

A diagram of a two stage sub-modeling scheme is shown in FIG. 10. In this approach, the test subject's spectra are initially categorized by SVD score (signal amplitude; skin color). Within each of the two skin color ranges, spectra are further sorted by gender discriminant models. The appropriate disease classification sub-model for that sub-group is then applied to assess the subject's disease risk score.

The illustration represents one embodiment but does not restrict the order or diversity of possible sub-modeling options. The example describes an initial amplitude parsing followed by sub-division following gender-based data-clustering. Effective sub-modeling could be obtained by reversing the order to of these operations or by performing them in parallel. Sub-groups can also be categorized by techniques or algorithms that combine simultaneous sorting by amplitude, shape or other signal characteristics.

Spectral Bundling

The present invention can provide an instrument that produces multiple fluorescence and reflectance spectra that are useful for detecting disease. As an example, a 375 nm LED can be used for both the first and second detection channels of the optical probe, resulting two reflectance spectra that span the 330 nm-650 nm region and two fluorescence emission spectra that span the 415-650 nm region. There are corresponding reflectance and fluorescence emission spectra for the other LED/detection channel combinations. In addition, a white light LED can produce a reflectance spectrum for each detection channel. In an example embodiment there are 22 spectra available for detection of disease.

Figure 31:
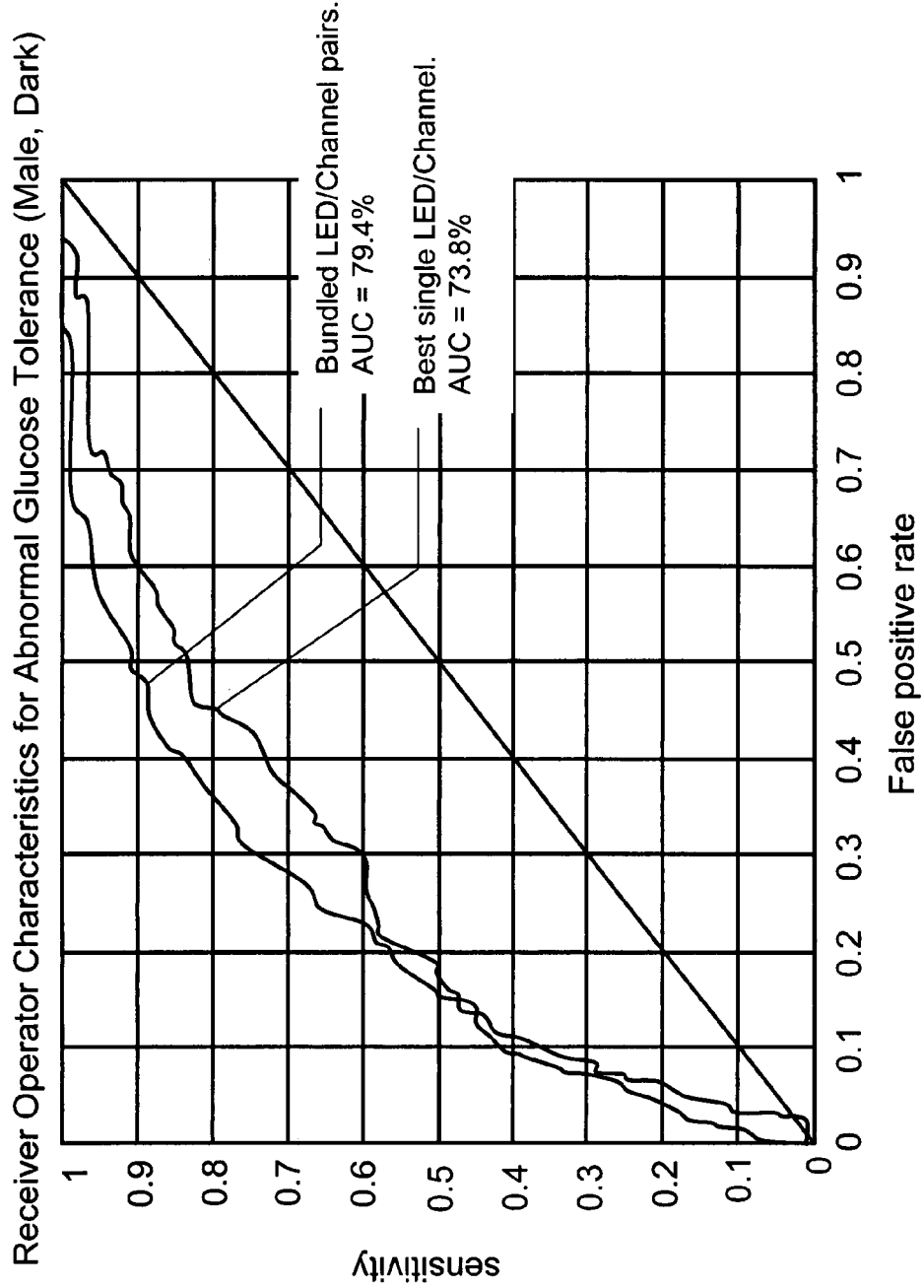
FIG. 31 is an illustration of a receiver operator characteristic relating to detection of impaired glucose tolerance.

As shown in the receiver operator characteristic of FIG. 31, it is possible to predict disease from a single spectrum for a given LED/detection channel pair, but a single region will not necessarily produce the best overall accuracy. There are several methods of combining the information from each of the LED/detection channel spectral predictions to produce the most accurate overall detection of disease. These techniques include simple prediction bundling, applying a secondary model to the individual LED/detection channel predictions, or combining some or all of the spectra together before performing the analysis.

In a simple bundling technique, disease detection calibrations are developed for each of the relevant LED/detection channel spectra. When a new set of spectra are acquired from an individual, the individual LED/detection channel calibrations are applied to their corresponding spectra and the resulting predictions, PPi (risk scores, posterior probabilities, quantitative disease indicators, etc.), are added together to form the final prediction. The adding of the individual LED/detection channel pairs can be equally (Equation 1) or unequally weighted by a LED/detection channel specific coefficient, ai, (Equation 2) to give the best accuracy.

Equation 1:
$$PP_{bundled} = \left(\sum_{i=1}^{i=n} PP_i\right)/n$$

Equation 2:
$$PP_{bundled} = \left(\sum_{i=1}^{i=n} \alpha_i * PP_i\right)/n$$

The more independent the predictions of the individual LED/detection channel spectra are relative to each other, the more effective the simple bundling technique will be. FIG. 31 is a receiver operator characteristic demonstrating the performance of the simple bundling technique with equal weighting to the individual LED/detection channel predictions.

The secondary modeling technique uses the predictions from the individual LED/detection channel calibrations to form a secondary pseudo spectrum that is input into a calibration model developed on these predictions to form the final prediction. In addition to the LED/detection channel predictions, other variables (scaled appropriately) such as subject age, body mass index, waist-to-hip ratio, etc. can to be added to the secondary pseudo spectrum. As an example, if there are 10 distinct LED/detection channel predictions, noted at PP1, PP2 through PP10 and other variables such as subject age, waist to hip ratio (WHR) and body mass index (BMI), a secondary spectrum ran comprise the following entries: Secondary spectrum=[PP1, PP2, PP3, PP4, PP5, PP6, PP7, PP8, PP9, age, WHR, BMI]

Figure 32:
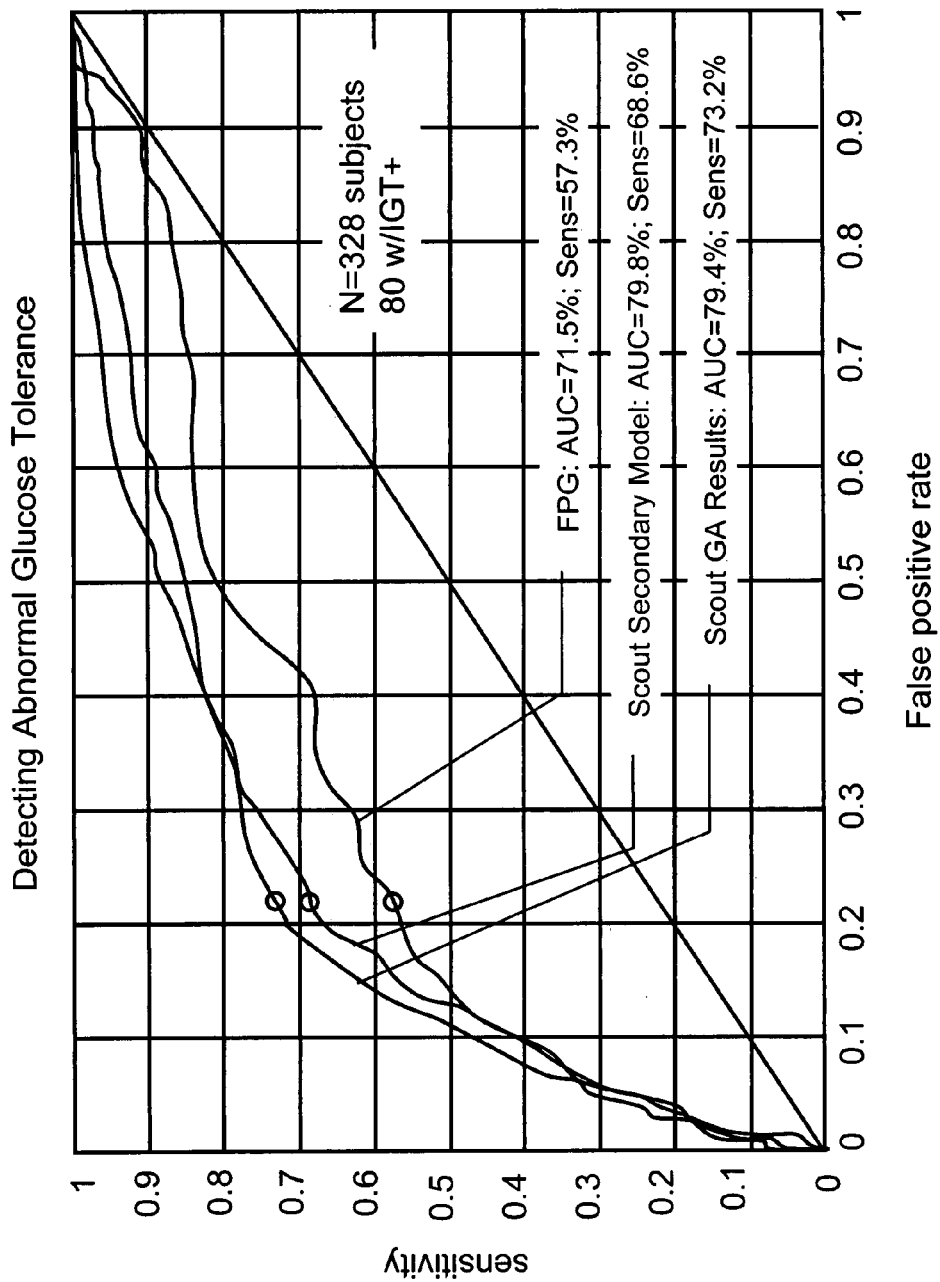
FIG. 32 is an illustration of a receiver operator characteristic relating to detection of impaired glucose tolerance.

A set of secondary spectra can be created from corresponding fluorescence, reflectance and patient history data collected in a calibration clinical study. Classification techniques such as linear discriminant analysis, quadratic discriminant analysis, logistic regression, neural networks, K nearest neighbors or other like methods are applied to the secondary pseudo spectrum to create the final prediction (risk score) of disease state. FIG. 32 illustrates the performance improvements possible with a secondary model versus simple bundling or a single LED/channel model.

The inclusion of specific LED/detection channel predictions can span a large space (many variations) and it can be difficult to do an exhaustive search of the space to find the best combination of LED/detection channel pairs. In this case, it is possible to use a genetic algorithm to efficiently search the space. See Goldberg, Genetic Algorithms in Search, Optimization and Machine Learning, Addison-Wesley, Copyright 1989 for more details on genetic algorithms. Also, Differential Evolution, ridge regression or other search techniques can be employed to find the optimal combination.

For purposes of the genetic algorithm or differential evolution, the LED/detection channels were mapped to 10 regions (i.e. 375 nm LED/channel 1=region 1; 375 nm LED/channel 2=region 6; 460 nm LED/channel 2=region 10) and the Kx, Km exponents for the intrinsic correction applied to each region we broken into 0.1 increments from 0 to 1.0, yielding 11 possible values for Kx and 11 possible values for Km. The following Matlab function illustrates the encoding of regions and their respective Kx, Km pairs into the chromosome used by the genetic algorithm:

```
function[region, km, kx]=decode(chromosome)

region(1)=str2num(chromosome(1));

region(2)=str2num(chromosome(2));

region(3)=str2num(chromosome(3));

region(4)=str2num(chromosome(4));

region(5)=str2num(chromosome(5));

region(6)=str2num(chromosome(6));

region(7)=str2num(chromosome(7));

region(8)=str2num(chromosome(8));

region(9)=str2num(chromosome(9));

region(10)=str2num(chromosome(10));

km(1)=min([bin2dec(chromosome(11:14))10])+1;

km(2)=min([bin2dec(chromosome(15:18))10])+1;

km(3)=min([bin2dec(chromosome(19:22))10])+1;

km(4)=min([bin2dec(chromosome(23:26))10])+1;

km(5)=min([bin2dec(chromosome(27:30))10])+1;

km(6)=min([bin2dec(chromosome(31:34))10])+1;

km(7)=min([bin2dec(chromosome(35:38))10])+1;

km(8)=min([bin2dec(chromosome(39:42))10])+1;

km(9)=min([bin2dec(chromosome(43:46))10])+1;

km(10)=min([bin2dec(chromosome(47:50))10])+1;

kx(1)=min([bin2dec(chromosome(51:54))10])+1;

kx(2)=min([bin2dec(chromosome(55:58))10])+1;

kx(3)=min([bin2dec(chromosome(59:62))10])+1;

kx(4)=min([bin2dec(chromosome(63:66))10])+1;

kx(5)=min([bin2dec(chromosome(67:70))10])+1;

kx(6)=min([bin2dec(chromosome(71:74))10])+1;

kx(7)=min([bin2dec(chromosome(75:78))10])+1;

kx(8)=min([bin2dec(chromosome(79:82))10])+1;

kx(9)=min([bin2dec(chromosome(83:8))10])+1;

kx(10)=min([bin2dec(chromosome(87:90))10])+1;
```

In the example implementation of the genetic algorithm, a mutation rate of 2% and a cross-over rate of 50% were used. Other mutation and cross-over rates are acceptable and can be arrived at either empirically or by expert knowledge. Higher mutation rates allow the algorithm to get unstuck from local maxima at the price of stability.

The population consisted of 2000 individuals and 1000 generations of the genetic algorithm were produced to search the region/Kx/Km space for the optimal combination of regions/Kx/Km. In this particular example the fitness of a given individual was assessed by unweighted bundling of selected region/Kx/Km posterior probabilities (generated previously and stored in a data file which is read in by the genetic algorithm routine for each region and Kx/Km pair per region using methods described in U.S. Pat. No. 7,139,598. "Determination of a measure of a glycation end-product or disease state using tissue fluorescence", incorporated herein by reference) to produce a single set of posterior probabilities and then calculating a receiver operator characteristic for those posterior probabilities against known disease status. The fitness of a given chromosome/individual was evaluated by calculating classification sensitivity at a 20% false positive rate from the receiver operator characteristic.

The sensitivity at a 20% false positive rate is but one example of an appropriate fitness metric for the genetic algorithm. Other examples would be fitness functions based on total area under the receiver operator characteristic, sensitivity at 10% false positive rate, sensitivity at 30% false positive rate, a weighting of sensitivities at 10, 20 and 30% false positive rates, sensitivity at a given false positive rate plus a penalty for % of outlier spectra, etc. The following Matlab functions are an example implementation of the genetic algorithm:

```
******************************************************************
function [X, F, x, f] = genetic(chromosomeLength, population Size, N,
mutation Probability,
crossoverProbability)
% -------------------------------------------------------------------------- %
% INPUTS:
%       chromosomeLength   (1x1 int) - Number of genes per chromosome.
%       populationSize    (1x1 int) - Number of chromosomes.
%       N          (1x1 int) - Number of generations.
%       mutationProbability (1x1 int) - Gene mutation probability (optional).
%       crossoverProbability (1x1 int) - Crossover probability (optional).
% OUTPUTS:
%       X (1xn char) - Best chromosome over all generations.
%       F (1x1 int) - Fitness corrosponding to X.
%       x (nxm char) - Chromosomes in the final generation.
%       f (1xn int) - Fitnesses associated with x.
% COMMENTS:
%       populationSize is the initial population size and not the size of the
%       population used in the evolution phase. The evolution phase of this
%       algorithm uses popuiationSize/ 10 chromosomes. It is thus required that
%       populationSize be evenly divisible by 10. In addition, because chromosomes
%       crossover in pairs, populationSize must also be evenly divisible by 2.
% -------------------------------------------------------------------------- %
if ~exist('mutationProbability', 'var')
      mutation Probability = 0.02;
end
if ~exist('crossoverProbabity', 'var')
      crossoverProbability = 0.50;
end
% Create the initial population of populationSize chromosomes. Gene values for
% each chromosome in the initial population are assigned randomly.
rand('state', sum(100 * clock));
rand('state')
for i = 1:populationSize
      x(i, :) = num2str(rand(1, chromosomeLength) > 0.5, '%1d');
end
% Trim the initial population by a factor of 10 based on fitness. The resulting
% population, which will contain populationSize / 10 chromosomes, will be used
% for the rest of this implementation.
f = fitness(x);
 [Y, l] = sort(f);
nkeep = popuiationSize / 10;
nstart = populationSize;
nend = populationSize + 1 – nkeep;
keep_ind = [nstart:–1:nend];
x = x(l(keep_ind),:);
f = f(l(keep_ind));
F = 0;
for i = 1:N
      x = select(x, f);
      x = crossover(x, crossoverProbability);
      x = mutate(x, mutationProbability);
      f = fitness(x);
      if max(f) > F
            F = max(f);
            l = find(f == F);
            X = x(l, :);
      end
end
******************************************************************
function y = select(x, f)
p = (f – min(f)) / (max(f – min(f)));
n = floor(p * length(f));
n = ceil(n / (sum(n) / length(f)));
l = [ ];
for i = 1:length(n)
      l = [l repmat(i, 1, n(i)) ];
end
l = l(randperm(length(l)));
y = x(l(1:length(f)), :);
******************************************************************
function f = fitness(chromosome)
for i = 1:size(chromosome, 1)
      [ region, km, kx ] = decode(chromosome(i, :));
      g = gaFitness(getappdata(0, 'GADATA'), region, km, kx);
      f(i) = g.bsens(2);
end
******************************************************************
function y = crossover(x, crossoverProbability)
if ~exist('crossoverProbability', 'var')
```

```
        crossoverProbability =1.0;
end
x = x(randperm(size(x, 1)), :);
y = x;
for i = 1:size(x, 1) / 2
    if (rand <= crossoverProbability)
        l = floor(rand * size(x, 2)) + 1;
        y((2 * i - 1), 1:l) = x((2 * i - 0), 1:l);
        y((2 * i - 0), 1:l) = x((2 * i - 1), 1:l);
    end
end
*************************************************************
function y = mutate(x, mutationProbability)
if ~exist('mutationPrabability', 'var')
    mutationProbability = 0.02;
end
y = x;
for i = 1:size(x, 1)
    l = find(rand(1, size(x, 2)) <= mutationProbability);
    for j = 1:length(l)
        if y(i, l(j)) == '0'
            y(i, l(j)) = '1';
        else
            y(i, l(j)) = '0';
        end
    end
end
*************************************************************
```

FIG. 32 illustrates the performance improvements possible with a genetic algorithm to search the Kx, Km space for each LED/channel pair and selecting regions to bundle.

Another method mentioned above involves taking the spectra from some or all of the LED/detection channel pairs and combining them before generating a calibration model to predict disease. Methods of combination include concatenating the spectra together, adding the spectra together, subtracting the spectra from each other, dividing the spectra by each or adding the to log10 of the spectra to each other. The combined spectra are then fed to a classifier or quantitative model to product the ultimate indication of disease state.

Data Regularization

Before applying any classification technique on a data set, various regularization approaches can be employed, as pre-processing steps, to a derived vector space representation of the spectral data in order to augment signal relative to noise. This normally entails removing or diminishing representative principal directional components of the data based on their respective variances in the assumption that disease class separation is more likely in directions of larger variance, which is not necessarily the case. These directional components can be defined in many ways: via Singular Value Decomposition, Partial Least Squares, QR factorization, and so on. As a better way to separate signal from noise, one can instead use other information from the data itself or other related data which is germane to disease class separation. One metric is the Fisher distance or similar measure, $$\left\{ d \equiv \frac{|u^+ - u^-|}{s^2(u^+) + s^2(u^-)} \right\}_m,$$

where u is a data directional component such as a left singular vector, or factor, from SVD. The metric d reveals the degree to which two labeled groups of points are spatially separated from each other in each component of the primary data set studied, which in our case is the spectral data set. In general, however, one can use information from sources outside the spectral data itself as well, such as separate empirical information concerning the relevance of the data components to the underlying phenomena (e.g., similarity of data components to real spectra), their degree of correlation to the data that drives the labeling scheme itself (such as that used for a threshold criterion of disease class inclusion), and so on.

Thus, for each data component, we can use, e.g., Fisher distance to weigh that component relative to the others or eliminate it altogether. In so doing, data components are treated differently from one another; those which demonstrate greatest separation between disease classes, or otherwise show greatest relevance to disease definition, are treated most favorably, thereby increasing the ability of a subsequently applied classification technique to determine a good boundary between disease and non-disease points in the data space. To each directional SVD component we multiply a severity-tunable filter factor such as $$F_j = \frac{d_j}{d_j + \gamma}$$

where dj is the Fisher distance, or any metric or other information of interest, for the jth directional component/factor, and γ is a tuning parameter which determines the degree to which the data components are treated differently. A search algorithm can be employed to find γ such that the performance of any given classifier is optimal.

Such a regularization approach can produce notable improvement in the performance of a classifier, as can be seen from the change in the ROC (Receiver Operating Characteristic) curve in Support Vector Regression (SVR), or Kernel Ridge Regression (KRR) based classification for skin fluorescence spectra shown below. See, e.g., The Nature of Statistical Learning Theory, Vladimir N. Vapnik, Springer-Verlag 1998; T. Hastie, R. Tibshirani, and J. H. Friedman, The Elements of Statistical Learning, Springer 2003; Richard O. Duda, Peter E. Hart and David G. Stork, Pattern Classification (2nd Edition), Wiley-interscience 2000 The details of the SVR/KRR based approach are examined below.

Regularization Results for SVR Classification

The results of disease detection sensitivity for the two cases of regularization, as defined by Fj above, and no-regularization are shown in FIG. 23-27 for the DE(SVR) wrapper classification technique in the form of ROC curves. The SVR results are based on spectral data which was age-compensated (see Compensation for Competitive Signal) inside a cross validation protocol. All other preprocessing in SVR, including regularization, was also done to each fold of a cross validation protocol for model stability and robustness. Previous results of regularized Linear Discriminant Analysis [GA (LDA)] are included as a reference. Regularization for GA(LDA) involved removal of SVD components ranked low in Fisher distance, as opposed to being weighted by Fj. The overall classification model was produced by the combined sub-model approach outlined in the Submodeling section.

Figure 23A:
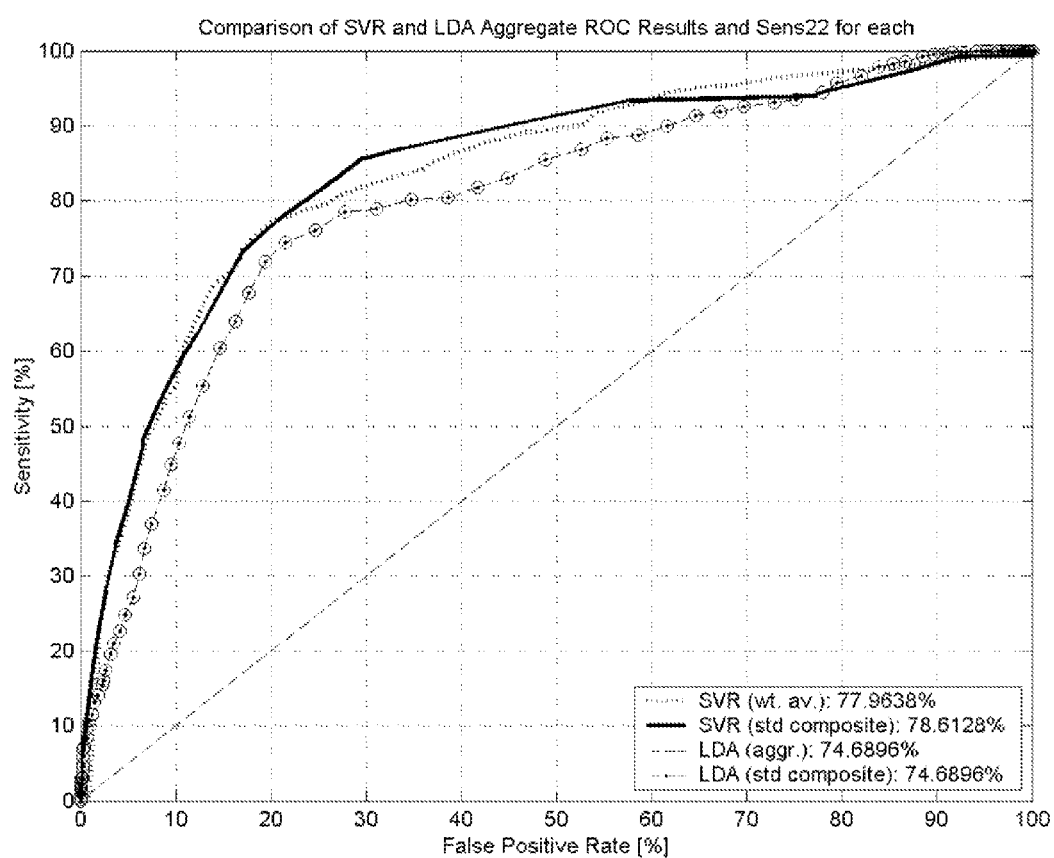
FIG. 23 illustrates aggregate results of the effect of data regularization according to the present invention on the skin fluorescence spectra in terms of sensitivity to disease with respect to SVR classification.
Figure 23B:
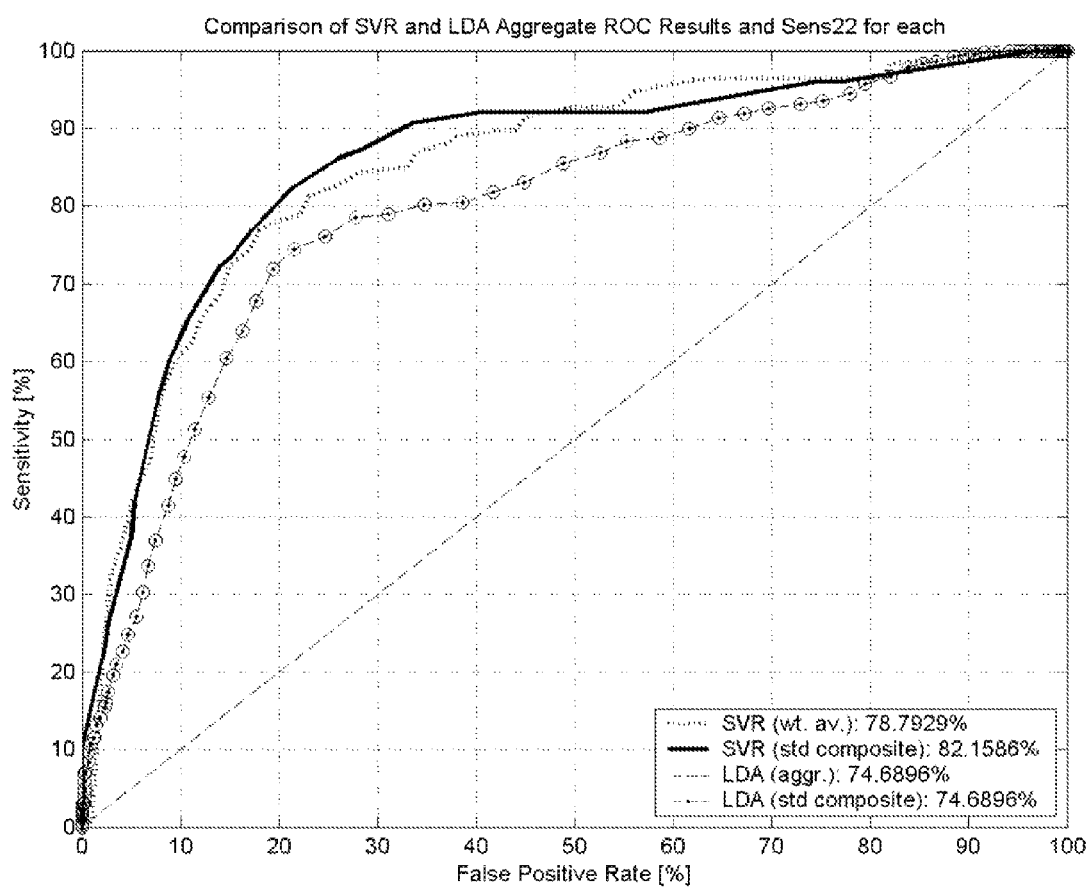
Figure 24A:
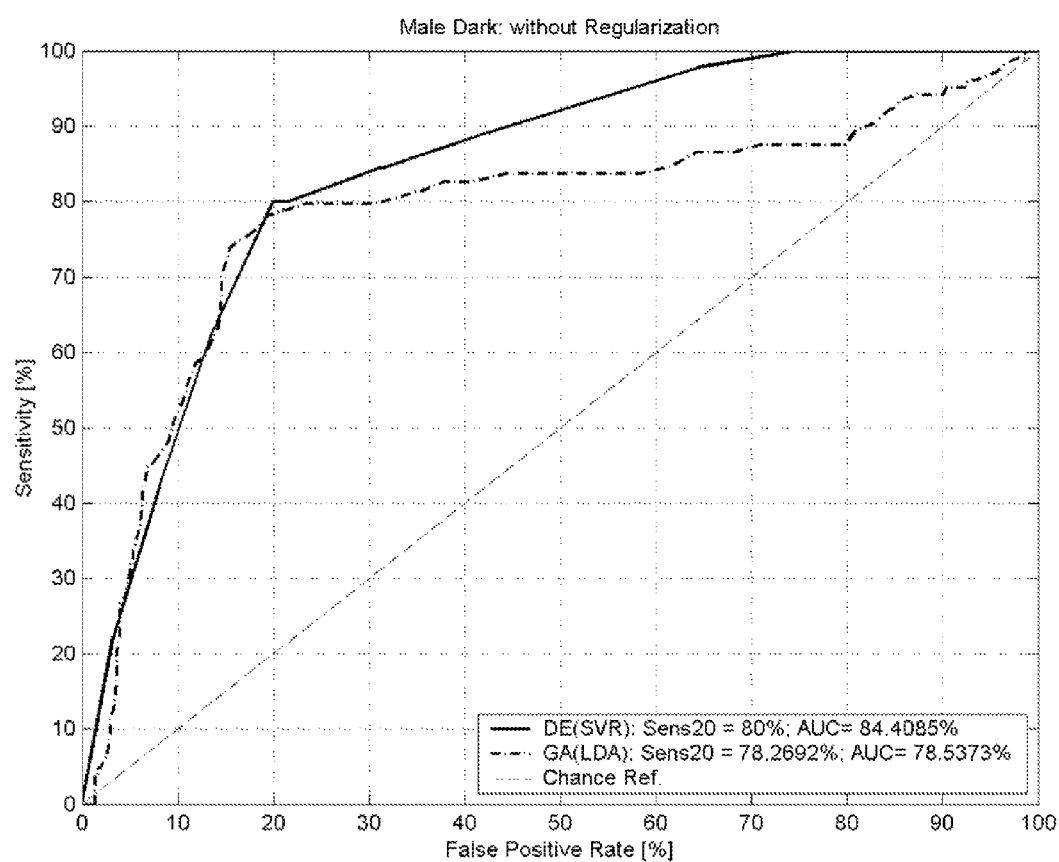
FIG. 24 illustrates results of the effect of data regularization for an individual sub-model for male/dark skin.
Figure 24B:
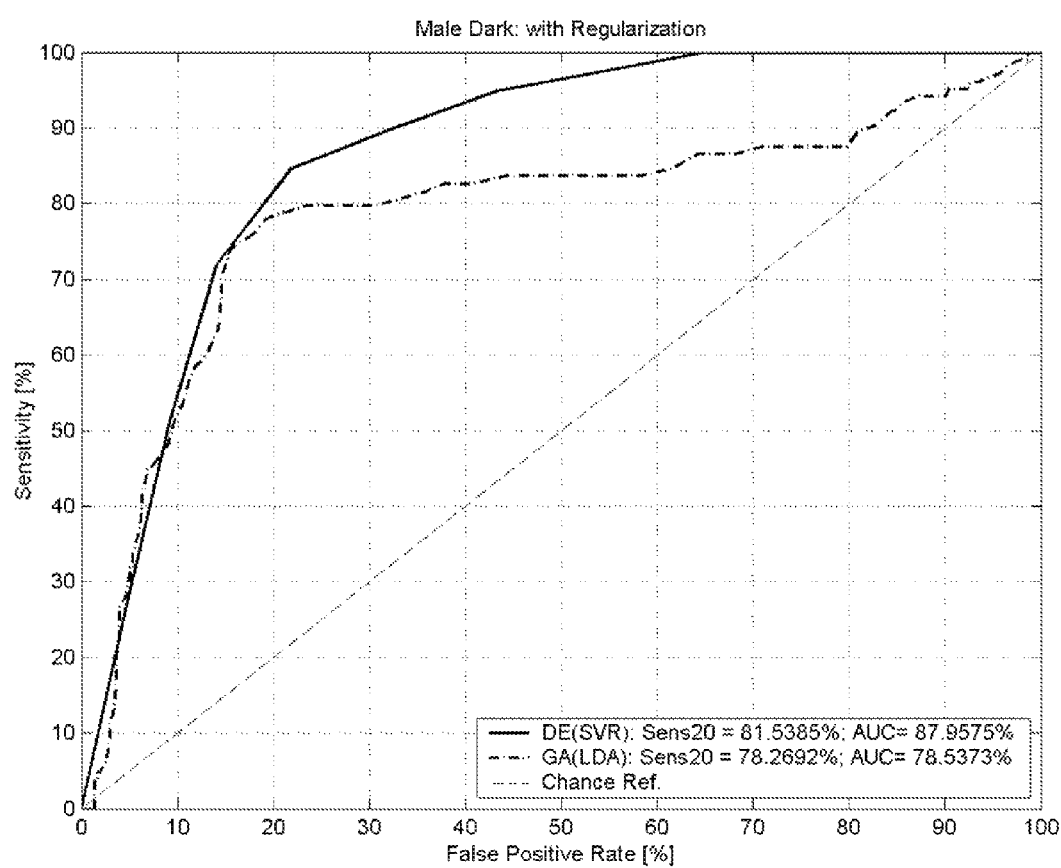
Figure 25A:
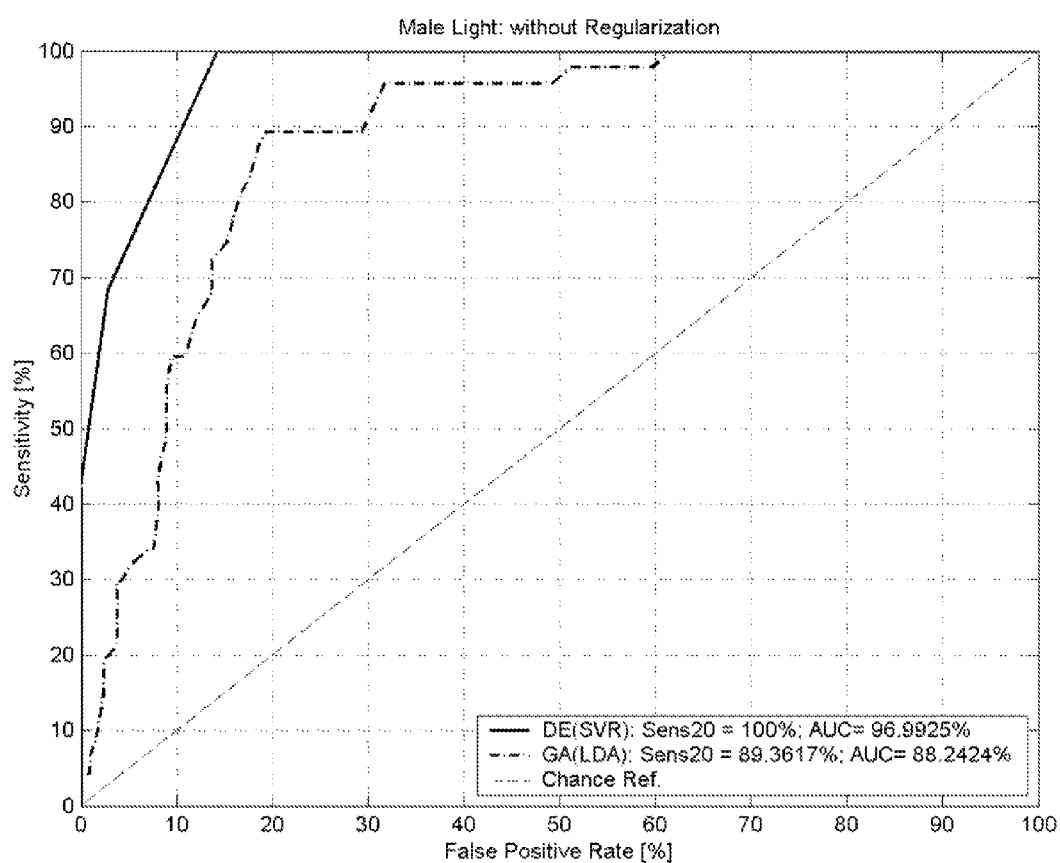
FIG. 25 illustrates results of the effect of data regularization for an individual sub-model for male/light skin.
Figure 25B:
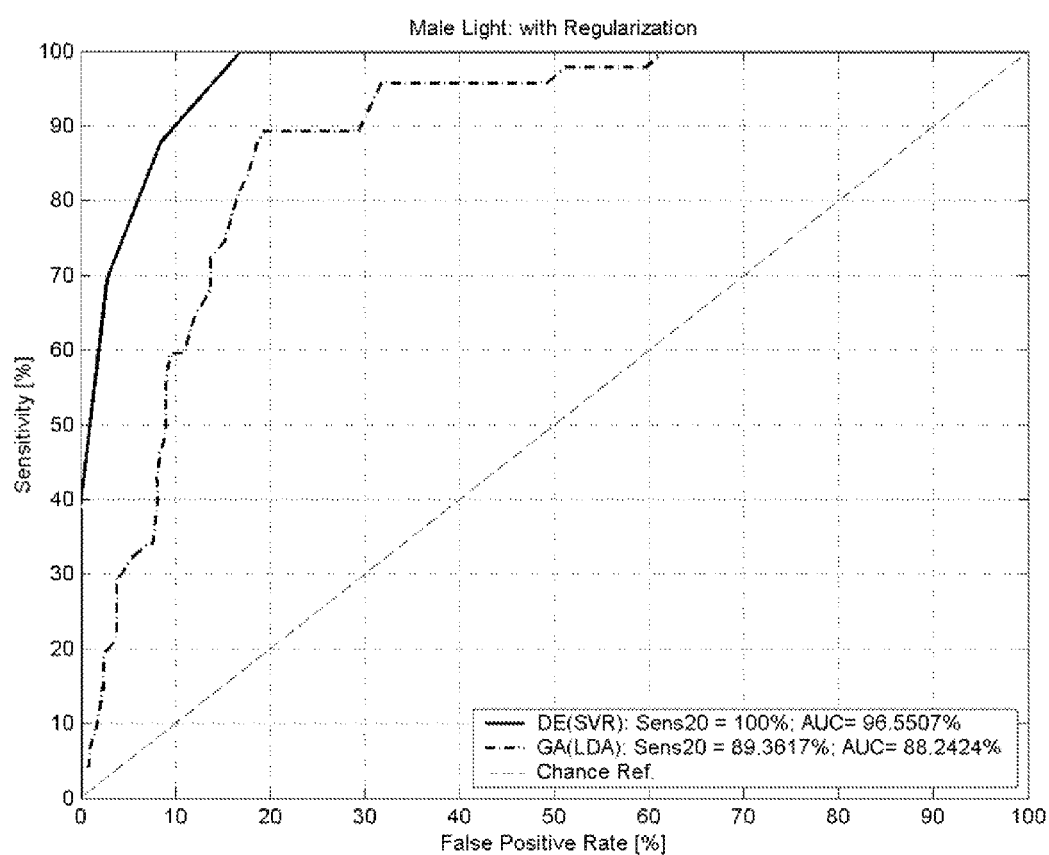
Figure 26A:
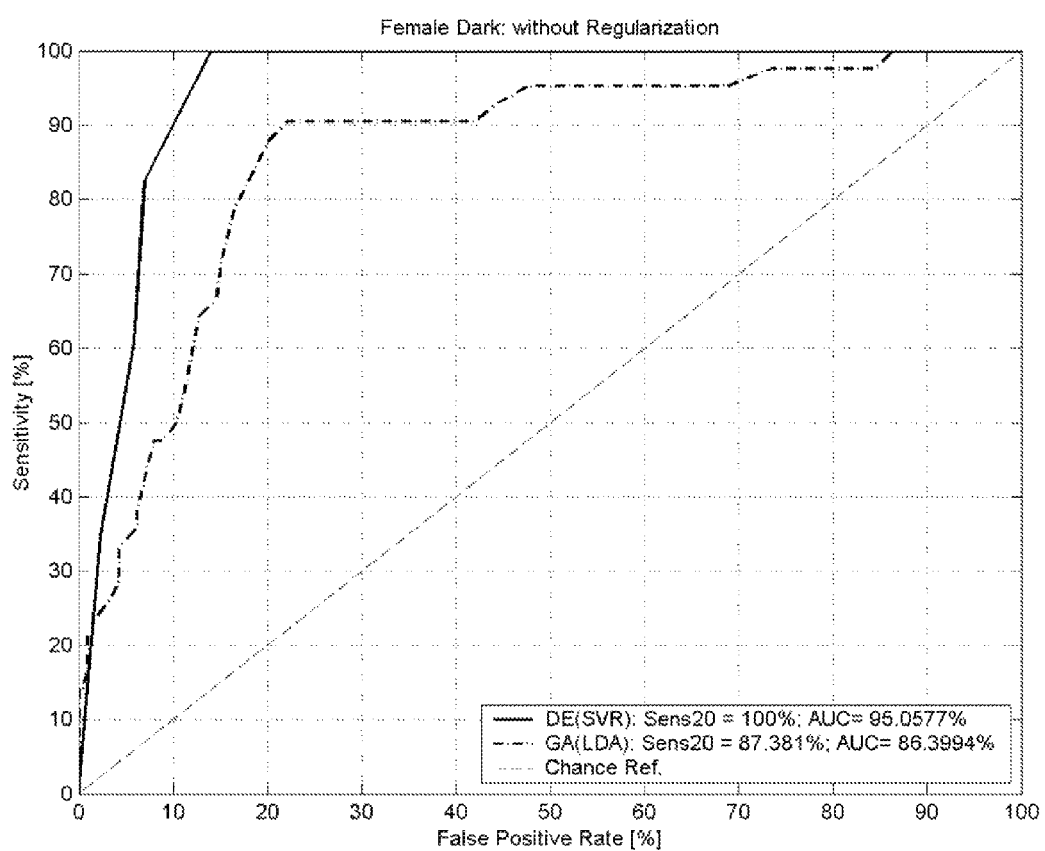
FIG. 26 illustrates results of the effect of data regularization for an individual sub-model for female/dark skin.
Figure 26B:
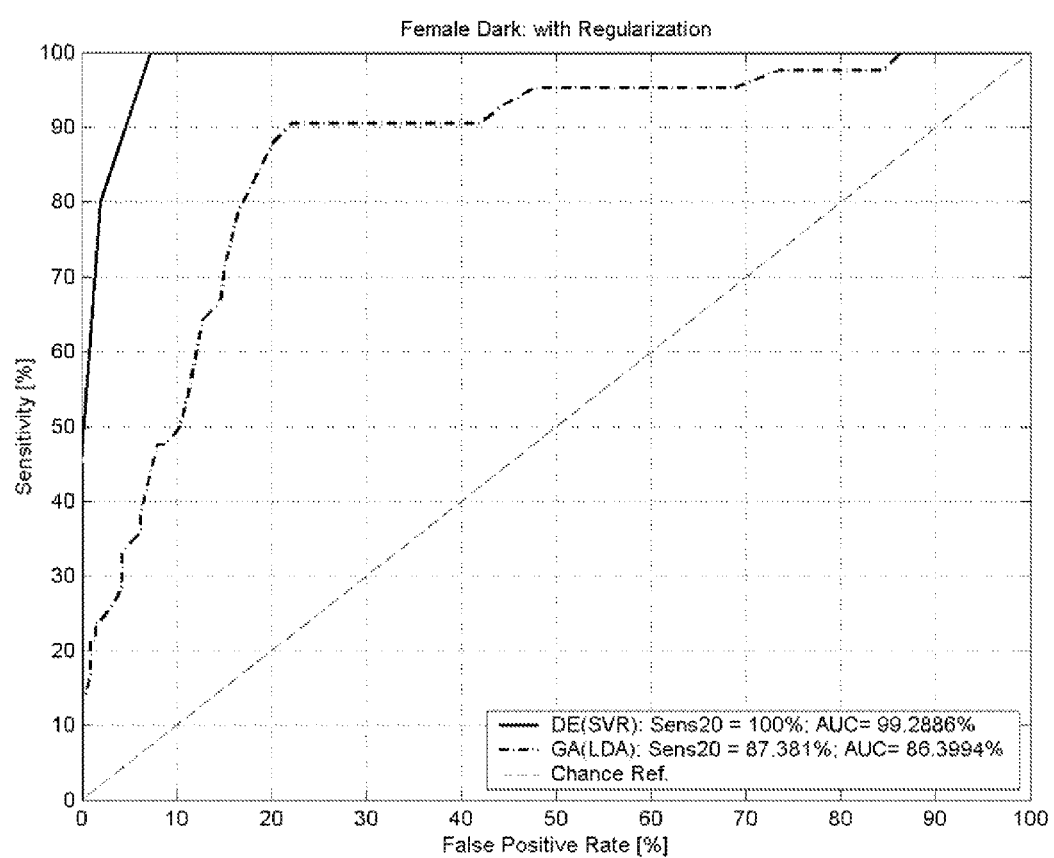
Figure 27A:
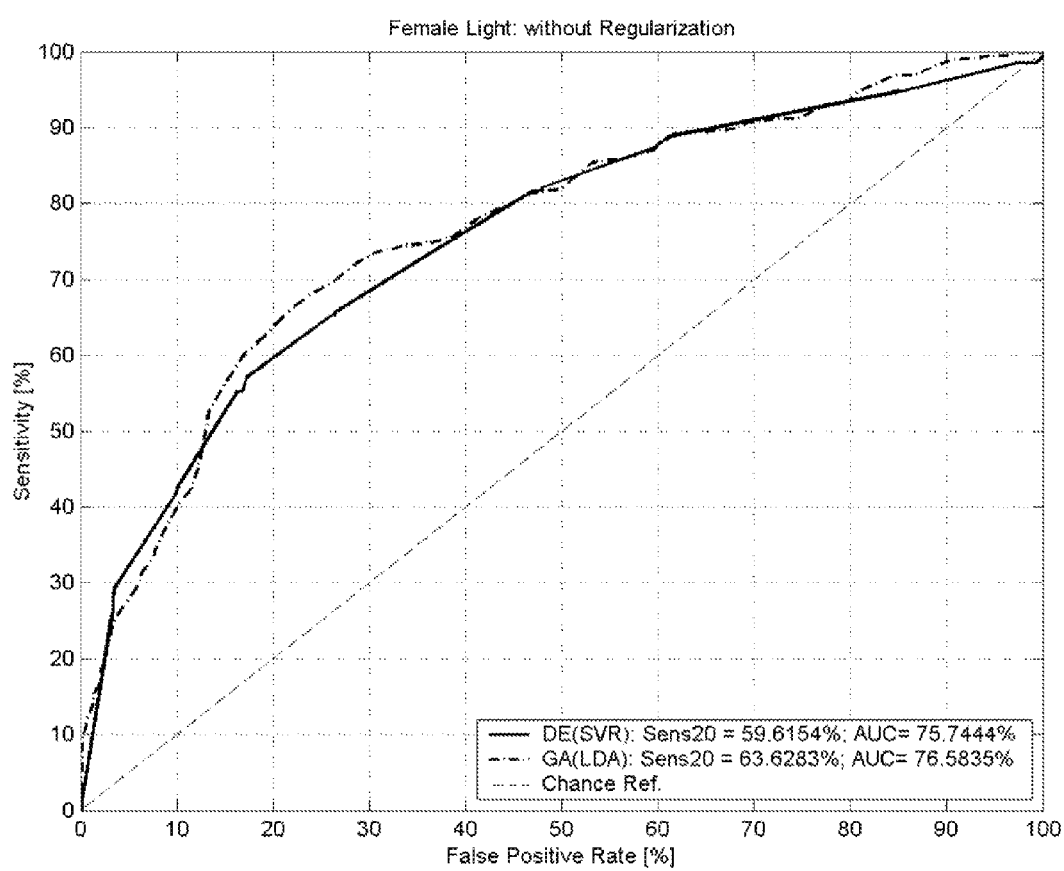
FIG. 27 illustrates results of the effect of data regularization for an individual sub-model for female/light skin.
Figure 27B:
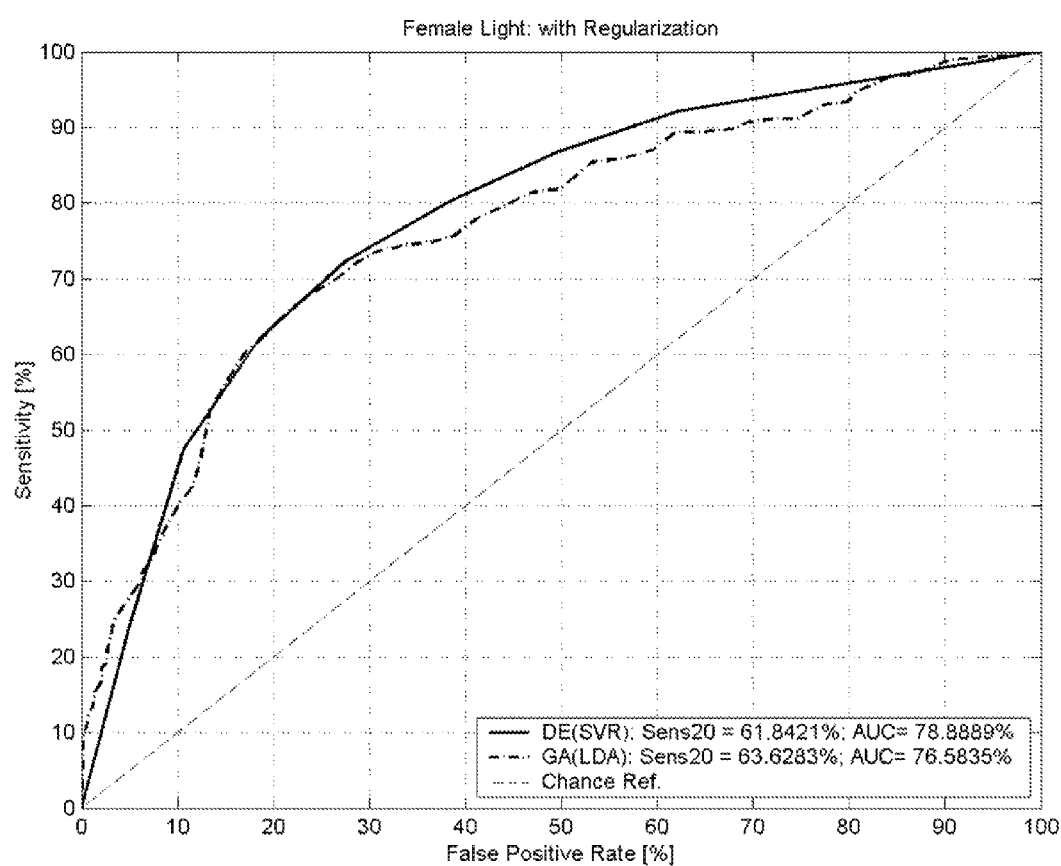

The results shown in FIG. 23-27 illustrate the effect of data regularization of the type described on the skin fluorescence spectra in terms of sensitivity to disease with respect to SVR classification. FIG. 23 illustrates aggregate results. FIG. 24 illustrates results for an individual sub-mode for male/dark skin. FIG. 25 illustrates results for an individual sub-model for male/light skin. FIG. 26 illustrates results for an individual sub-model for female/dark skin. FIG. 27 illustrates results for an individual sub-model for female/light skin. Both the LDA and SVR methodologies involved tuning parameters (for the data normalization as well as the classification algorithm itself and were found via the use of a Genetic Algorithm for the case of LDA and via the use of a technique known as Differential Evolution for the case of SVR. See, e.g., Differential Evolution. A Practical Approach to Global Optimization, Price et al, Springer 2005. These are respectively referred to as GA(LDA) and DE(SVR) wrapper approaches. The DE(SVR) results were generated by combining together the standardized scores of all the SVR sub-models. The results for GA(LDA) were similarly produced from the sub-models. Also shown is the weighted average of the sensitivities for all the sub-models for SVR (weighted by the number of points in each submodel), which is expected to be similar to the DE(SVR) curve and is shown as a reasonable check on the results.

Details of DE(SVR) Based Classification Methodology

The following describes a methodology for producing an empirically stable nonlinear disease classifier for spectral response measurements in general (e.g., fluorescence of the skin, etc.) but can also be used with non-spectral data. Let $x_i$ denote one of a set $X_m \in X$ of N spectral measurement row vectors such that $$X_m = \{x_1, x_2, x_3, \ldots, x_i, \ldots x_N\}_m \in \Re^{N \times D},$$

where $X_m$ denotes a given cross validation fold (subset) of the original data set X and each column (i.e., each of the D response dimensions) is standartized to unit variance and zero mean; and let $y_i$ be one of N corresponding binary class labels $$y_m = \{y_1, y_2, y_3, \ldots, y_i, \ldots, y_N\}_m \in \Re^N$$

for each $x_i$, such that $y_i = +1 \leftarrow$ Disease Positive $y_i = -1 \leftarrow$ Disease Negative defines the two disease state classes for the data.

For each $X_m$ one computes the Singular Value Decomposition such that $$\left\{ \begin{aligned} X &= USV^T \\ XV &= US \end{aligned} \right\}_m$$

Then, imposing a filter factor regularization matrix $F_m$, we have $$\left\{ \begin{aligned} X(VF) &= U(SF) \\ X\tilde{V} &= U\tilde{S} \end{aligned} \right\}_m$$

with $F_m$ defined as $$F_m = diag\left[\frac{d_j}{d_j + \gamma}\right]_m$$

which is a K×K diagonal matrix with K=rank(U): j denotes the $j^{th}$ of the K total left singular (column) vectors $\{u_j \in U\}_m$ [$u_j$ is also referred to as an SVD factor];

$$\left\{ d_j \equiv \frac{|u_j^+ - u_j^-|}{s^2(u_j^+) + s^2(u_j^-)} \right\}_m$$

is the Fisher distance between the disease-positive labeled points $\{u_j^+\}_m$ and the disease-negative labeled points $\{u_j^-\}_m$ for each SVD factor; and $s^2$ denotes the variance.

In this way the SVD factors are weighted relative to each other according to disease separation. Those factors with highest disease separation are treated preferentially. The tuning parameter $\gamma$ determines the degree to which the SVD factors are treated differently.

At this point a classification procedure known variously as Kernel Ridge Regression (KRR) or Support Vector Regression (SVR) is employed as follows. Letting $x_i \leftarrow x_i^m$, the problem is to minimize $$H = \sum_{j=1}^{N} V(y_i - f(x_i)) + \frac{\lambda}{2}\|f\|^2$$

with respect to the set of coefficients $\{f_p\}$ given that $$f(x_i) = \sum_{p=1}^{M} f_p h_p(x_i)$$

is the Hilbert space expansion of a solution function f in the basis set $\{h_m\}$, and $$\|f\|^2 = \sum_{p=1}^{M} f_p^2$$

is the norm of f.

V is an error function, which was chosen to be $$V(r) = \begin{cases} 0, & \text{if } |r| < \varepsilon \\ |r| - \varepsilon, & \text{otherwise} \end{cases}$$

and λ is another tuning parameter.

Given the form of V above, the solution of equation (1) can be written as $$f(x) = \sum_{m=1}^{M} f_p h_p(x_i)$$

$$= \sum_{i=1}^{N} a_i K(x, x_i)$$

The kernel function K was chosen to be $$K(x, x_i) = \exp\left[-\frac{\|x - x_i\|^2}{2\sigma^2}\right]$$

which is known as the radial basis function.

In general, only a number of the coefficients $\{\alpha_i\}$ in the solution f(x) will not be zero. The corresponding data vectors $x_i$ are known as support vectors and represent the data points which together are sufficient to represent the entire data set. Depending on the relative fraction of the support vectors that make up the data set, the solution of SVR can be less dependant on outliers and less dependant on the covariance structure of the entire data set. In this sense, the SVR method tries to find the maximum amount of data-characterizing information in the least number of data points. This is in contrast to, for example, Linear Discriminant techniques which are dependant on the covariance of the data set, which involves all the points used in the calibration.

General Health Monitor

Initial experiments with the present invention related to diabetes screening and diagnosis. The skin of individuals with abnormal glucose levels accumulates fluorescent collagen cross-links and other advanced glycation endproducts (AGEs) at accelerated rates compared to those in health. Like skin, collagen in other organs and the vasculature develop crosslinks that compromise their functionality and lead to higher incidence of disease and complications such as nephropathy, retinopathy, neuropathy, hypertension, cardiovascular events or Alzheimer's disease. Skin fluorescence is related to weakened and/or damaged collagen in internal organs. Consequently, skin fluorescence can be used as a general health monitor and/or to assess the risk of diseases other than diabetes. Similar instrument calibration techniques can be utilized to develop multivariate spectroscopy models to assess general health, provide a risk indicator for development of micro and/or macrovascular disease or provide a risk indicator for Alzheimer's disease. The regression variable (i.e. degree of a particular disease like retinopathy, nephropathy, neuropathy, etc.) is appropriately chosen to represent the disease or health condition of interest and then fluorescence and reflectance tissue spectra (skin, oral mucosa, etc.) are collected from individuals with varying levels of the disease or condition of interest (including controls without disease). The regression variable and spectra can be input to multivariate calibration techniques described in herein to generate the model used on a prospective basis going forward to detect disease or give a indication of an individual's health.

Those skilled in the art will recognize that the present invention can be manifested in a variety of forms other than the specific embodiments described and contemplated herein. Accordingly, departures in form and detail can be made without departing from the scope and spirit of the present invention as described in the appended claims.

What we claim is:

1. A method of determining a state of health of an individual, where "state of health" is any of (i) a disease state based on long-term changes (greater than one month duration) in tissue, (ii) a measure of chemical change based on long-term (greater than one month duration) glycemic control, (iii) a measure of glycation end-products in tissue, and (iv) a combination of the above, comprising:
   (a) illuminating a portion of a tissue of the individual with excitation light;
   (b) detecting light emitted from the tissue by fluorescence of a chemical within the tissue, where the tissue is not the lens of the eye;
   (c) acquiring biologic information relating to the individual, wherein the biologic information comprises one or more of: gender of the individual, height of the individual, weight of the individual, waist circumference of the individual, history of disease in the individual's family, ethnicity, skin melanin content, and smoking history of the individual;
   (d) determining the state of health from the detected light and a model relating tissue fluorescence and biologic information to a state of health.

2. A method as in claim 1, wherein the tissue comprises the tissue on an extremity of the individual.

3. A method as in claim 2, wherein the tissue comprises the tissue on a leg of the individual.

4. A method as in claim 3, wherein the tissue comprises skin on the foot of the individual.

5. A method as in claim 3, wherein the tissue comprises skin on the upper leg of the individual.

6. A method as in claim 3, wherein the tissue comprises skin on the lower leg of the individual.

7. A method as in claim 2, wherein the tissue comprises the tissue on an arm of the individual.

8. A method as in claim 7, wherein the tissue comprises skin on the hand of the individual.

9. A method as in claim 7, wherein the tissue comprises skin on the upper arm of the individual.

10. A method as in claim 1, wherein the tissue comprises the tissue on the torso of the individual.

11. A method as in claim 10, wherein the tissue comprises skin on the neck of the individual.

12. A method as in claim 10, wherein the tissue comprises skin on the buttocks of the individual.

13. A method as in claim 1, wherein the tissue comprises the tissue on the head of the individual.

14. A method as in claim 13, wherein the tissue comprises the sclera of the eye of the individual.

15. A method as in claim 13, wherein the tissue comprises the oral mucosa of the individual.

16. A method as in claim 13, wherein the tissue comprises the earlobe of the individual.

17. A method as in claim 13, wherein the tissue comprises skin on the cheek of the individual.

18. A method as in claim 13, wherein the tissue comprises skin on the forehead of the individual.

19. A method as in claim 1, wherein the step of detecting light emitted from the tissue comprises placing a flexible probe in contact with the tissue.

20. A method as in claim 19, wherein the flexible probe comprises a bundle of input and output fiber optic cables that are arranged in a pattern at a surface of the probe that is placed in contact with the tissue.

21. A method as in claim 1, further comprising determining a tissue reflectance characteristic, and wherein the tissue fluorescence detected in step (b) is adjusted according to the tissue reflectance characteristic prior to use in step (d).

22. A method as in claim 1, wherein determining the state of health from the detected light and a model relating fluorescence and a state of health comprises determining the state of health in part from a measure of intrinsic fluorescence of the tissue.

23. A method as in claim 1, wherein the step of detecting light emitted from the tissue comprises detecting light with a sampler that does not contact the tissue.

24. An apparatus for the determination of a state of health in an individual, where "state of health" is any of (i) a disease state based on long-term changes (greater than one month duration) in tissue, (ii) a measure of chemical change based on long-term (greater than one month duration) glycemic control, (iii) a measure of glycation end-products in tissue, and (iv) a combination of the above, comprising:

(a) an illumination subsystem adapted to illuminate a portion of the tissue of the individual with excitation light, where the tissue is one or more of tissue on an extremity of the individual, tissue on the torso of the individual, or tissue on the head of the individual, and where the tissue is not the lens of the eye;

(b) a detection subsystem adapted to detect light emitted from the tissue by fluorescence of a chemical within the tissue;

(c) a data collection subsystem configured to acquire biologic information relating to the individual, wherein the biologic information comprises one or more of: gender of the individual, height of the individual, weight of the individual, waist circumference of the individual, history of disease in the individual's family, ethnicity, skin melanin content, and smoking history of the individual;

(d) an analysis subsystem, comprising a model relating fluorescence property of the skin of an individual and biologic information to a state of health.

25. An apparatus as in claim 24, wherein the detection subsystem comprises a flexible probe adapted to be placed in contact with the tissue.

* * * * *